(12) United States Patent
Sampson et al.

US008795647B2

(10) Patent No.: US 8,795,647 B2
(45) Date of Patent: Aug. 5, 2014

(54) ALTERNATING RING-OPENING METATHESIS POLYMERIZATION

(75) Inventors: Nicole Sampson, Setauket, NY (US); Kathlyn Parker, Setauket, NY (US); Airong Song, San Diego, CA (US)

(73) Assignee: The Research Foundation for The State University of New York, Albany, NY (US)

( * ) Notice: Subject to any disclaimer, the term of this patent is extended or adjusted under 35 U.S.C. 154(b) by 488 days.

(21) Appl. No.: 13/059,707

(22) PCT Filed: Aug. 20, 2009

(86) PCT No.: PCT/US2009/054538
§ 371 (c)(1),
(2), (4) Date: May 20, 2011

(87) PCT Pub. No.: WO2010/022284
PCT Pub. Date: Feb. 25, 2010

(65) Prior Publication Data
US 2011/0212046 A1      Sep. 1, 2011

Related U.S. Application Data

(60) Provisional application No. 61/189,684, filed on Aug. 20, 2008.

(51) Int. Cl.
*A61K 31/74* (2006.01)
*C08F 232/04* (2006.01)
*C08F 299/02* (2006.01)
*C08F 4/78* (2006.01)
*C08F 4/80* (2006.01)
*A61K 47/48* (2006.01)
*C08G 61/08* (2006.01)

(52) U.S. Cl.
CPC .......... *C08G 61/08* (2013.01); *A61K 47/48176* (2013.01)
USPC .................. 424/78.08; 424/78.31; 424/78.32; 424/78.35; 424/405; 525/268; 525/269; 525/276; 525/278; 525/279; 525/289; 525/291; 525/298; 526/135; 526/171

(58) Field of Classification Search
CPC ... A61K 47/48176; A61K 47/32; C08G 61/08
USPC ........................... 526/135, 171; 525/268–298; 424/78.08–78.35, 405
See application file for complete search history.

(56) References Cited

U.S. PATENT DOCUMENTS

| 4,590,174 | A | 5/1986 | Kukes et al. |
| 6,433,113 | B1 | 8/2002 | Mukerjee et al. |
| 6,946,533 | B2 | 9/2005 | Grubbs et al. |
| 6,987,154 | B2 | 1/2006 | Choi et al. |
| 2002/0166629 | A1 | 11/2002 | Caster et al. |

OTHER PUBLICATIONS

Pillai (Textbook of Organic Chemistry, p. 174, Published by Universities Press (India) Private Ltd 2009).*
Bornand, M. et al., "Mechanistically Designed Dual-Site Catalysts for the Alternating ROMP of Norbornes and Cyclooecteene", Organometallics (2007), vol. 26, pp. 3585-3596.
Kumar, R. et al., "Supramolecular assemblies based on copolymers of PEG600 and functionalized aromatic diesters for druge delivery applications", JACS (2004), vol. 126, pp. 10640-10643.
Astruc, D. "The metathesis reactions: from a historical perspective torecent developments", New J. Chem. (2005), vol. 29, pp. 42-56.
Campbell, A. et al., "The Synthesis of Caryophyllenic Acid", J. Chem. Soc. (1953), pp. 3002-3008.
Choi, T. L. et al., "Olefin Metathesis Involving Ruthenium Enoic Carbene Complexes", Journal of the American Chemical Society (2001), vol. 123, pp. 10417-10418.
Choi, T. L. et al., "Synthesis of A,B-Alternating Copolymers by Ring-Opening-Isertion-Metathesis Polymerization", Angewandte Chemie-Intl. Ed. (2002) vol. 41:20, pp. 3839-3841.
Fomine, S. et al., "Ring-Opening of Cyclohexene via Metathesis by Ruthenium Carbene Complexes. A Computational Study", Organometallics (2007), vol. 26, pp. 4491-4497.
Griffin, R. J. et al., "Resistance-Modifying Agents. 8.1 Inhibition of O6-Alkylguanine-DNA Alkyltransferase by O6-Alkenyl-, O6-Cycloalkenyl-, and O6-(2-Oxoalkyl)guanines and Potentiation of Temozolomide Cytotoxicity in Vitro by O6-(1-Cyclopentenylmethyl)guanine", J. Med. Chem. (2000), vol. 43, pp. 4071-4083.
Hashiyama, T. et al., "a-Hydroxy Ketones in High Enantiomeric Purity from Asymmetric Dihydroxylation of Enol Ethers", J. Org. Chem. (1992), vol. 57, pp. 5067-5068.
Ilker, M. F. et al., "Alternating Copolymerizations of Polar and Nonpolar Cyclic Olefins by Ring-Opening Metathesis Polymerization", Macromolecules (2002), vol. 35, pp. 54-58.
Lee, J. C. et al., "Amino Acid-Bearing ROMP Polymers with a Stereoregular Backbone", J. Am. Chem. Soc. (2006), vol. 128, pp. 4578-4579.
Love, J. A. et al., "A Practical and Highly Active Ruthenium-Based Catalyst that Effects the Cross Metathesis of Acrylonitrile", Angew Chem Int Edit (2002), vol. 41, pp. 4035-4037.
Marcune, B. F. et al., "Asymmetric Synthesis of Cyclic Hydroxy Ketones Derived from Enol Ethers via Sharpless Asymmetric Dihydroxylation. A Study in the Correlation of the Enol Ether Chain Length and Enantioselectivity", J. Org. Chem. (2003), vol. 68, pp. 8088-8091.
Mathias, L. J., "Esterification and Alkylation Reactions Employing Isoureas", Synthesis-Stuttgart (1979), pp. 561-576.
Wohl, R. A., "A Convenient One-Step Procedure for the Synthesis of Cyclic Enol Ethers. The Preparation of 1-Methoxy-1-cycloalkenes", Synthesis (1974), pp. 38-40.

* cited by examiner

*Primary Examiner* — Richard Schnizer
*Assistant Examiner* — Alma Pipic
(74) *Attorney, Agent, or Firm* — Kenyon & Kenyon LLP

(57) ABSTRACT

The invention relates to the field of polymers and olefin polymerization, and more specifically olefin metathesis polymerization. The invention provides regioregular alternating polymers and methods of synthesizing such polymers.

15 Claims, 42 Drawing Sheets

A. Substructure in alternating AB copolymer

AB repeat

B. Substructures in AB block copolymer

AA repeat

BB repeat

A: ring-opened cyclobutene subunit
B: ring-opened cyclohexene subunit

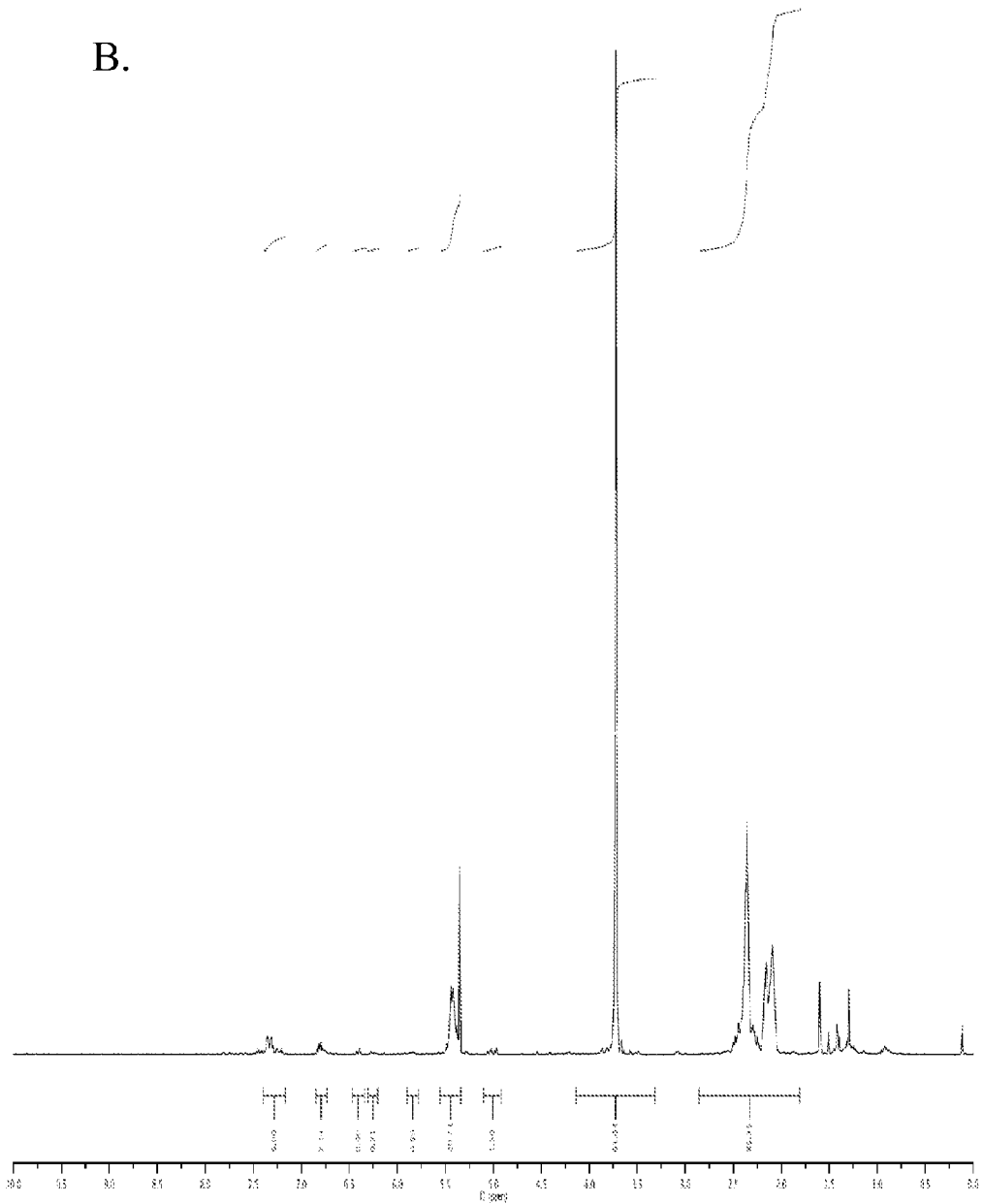
Fig. 36 (con't.)

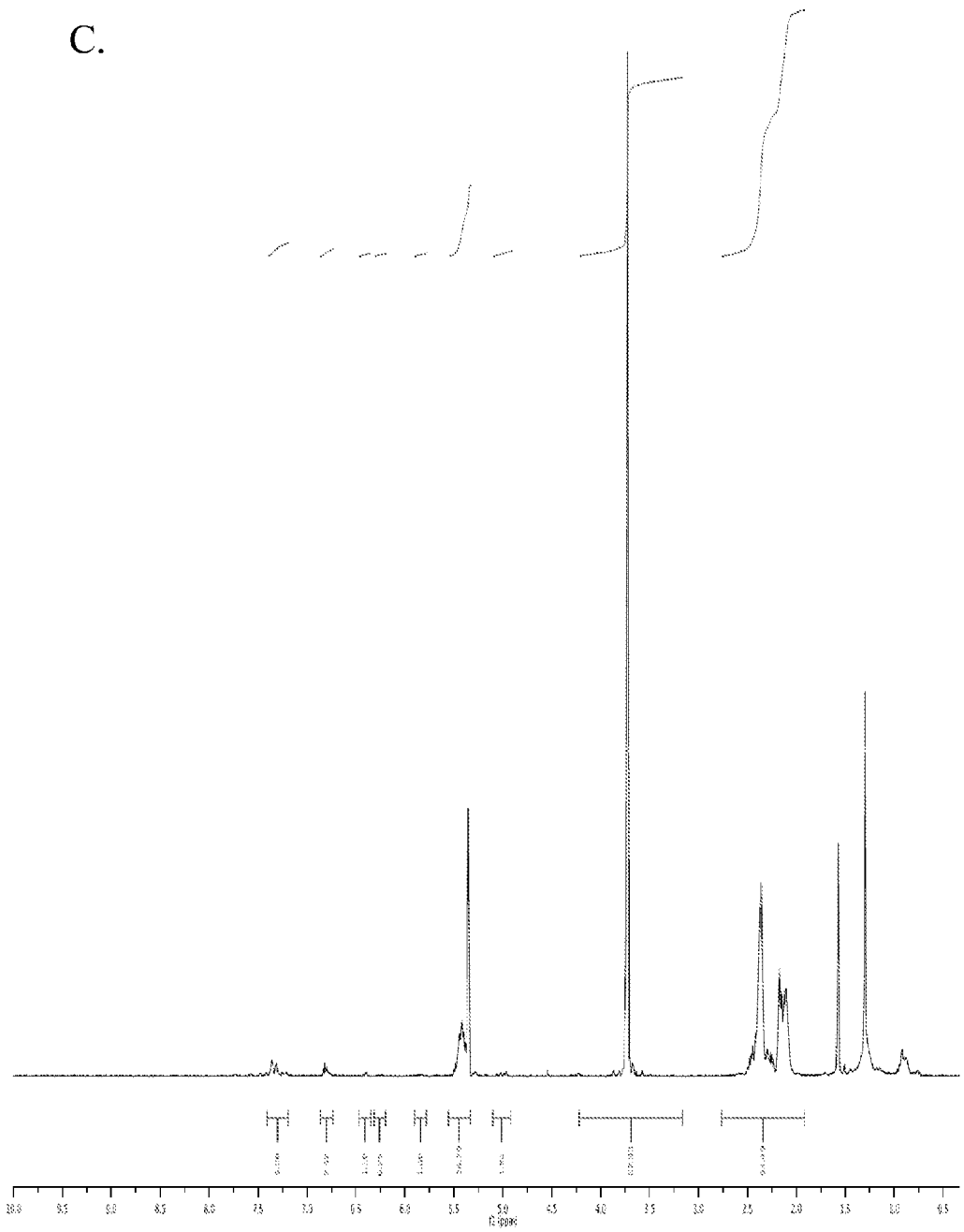
Fig. 36 (con't.)

ALTERNATING RING-OPENING METATHESIS POLYMERIZATION

CROSS REFERENCE TO RELATED APPLICATIONS

This application is the national phase application of International application number PCT/US2009/054538, filed Aug. 20, 2009, which claims priority to U.S. Application No. 61/189,684 filed Aug. 20, 2008, which is incorporated herein by reference in its entirety.

GOVERNMENT FUNDING

This invention was made with government support under grant numbers R01HD038519, S10RR021008, and R01GM074776 awarded by the NIH and grant number CHE0131146 awarded by the NSF. The U.S. Government has certain rights in this invention.

FIELD OF THE INVENTION

The invention relates to the field of polymers and olefin polymerization, and more specifically olefin metathesis polymerization.

BACKGROUND

Copolymers are employed in a wide range of materials, ranging from bulk plastics to specialized coatings, pharmaceutical compositions, and biomedical and electronic devices. Among the most commonly used are block copolymers, which often rely on phase separation of the two blocks for their functional properties, for example in drug delivery nanoparticles, and random copolymers, which incorporate two or more functional moieties that act co-operatively, for example in organic light emitting diodes. Regularly alternating polymers allow for controlled positioning of functional substituents, but they are difficult to access synthetically.

Regioregular alternating polymers (for example, SAN, styrene-acrylonitrile, an alternating copolymer used in plastics) are generally synthesized by radical polymerization with kinetic control of alternation in the polymerization reaction. Recently, ring opening metathesis polymerization (ROMP) and ring opening insertion metathesis polymerization (ROIMP) have been employed to synthesize alternating polymers: Ilker, M. F.; Coughlin, E. B. *Macromolecules* 2002, 35, 54-58; Choi, T. L.; Rutenberg, I. M.; Grubbs, R. H. *Angewandte Chemie-Intl. Ed.,* 2002, 41, 3839-3841.

The existing methods of formation of alternating polymers are limited, and there remains a need for new and more structurally diverse substrates and polymers. The present invention provides substrate and catalyst combinations that can generate a wider range of alternating polymers, having a range of diverse properties.

BRIEF DESCRIPTION OF THE INVENTION

The invention provides a method for the ROMP synthesis of alternating AB copolymers comprising the repeating unit Ia or Ib,

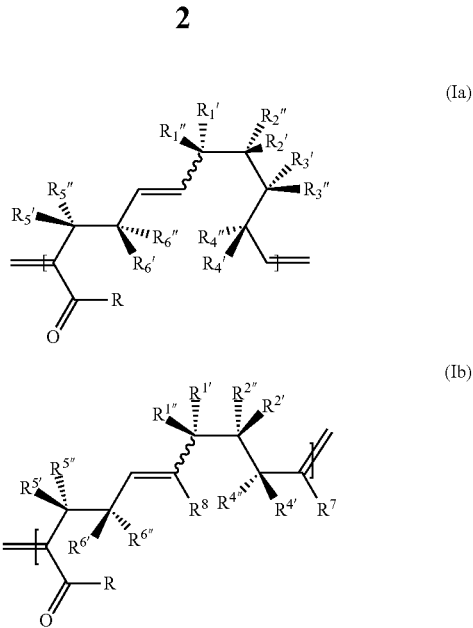

in which the A monomer is derived from a cyclobutene 1-carboxyl or 1-carbonyl derivative III, and the B monomer is derived from a cyclohexene derivative IIa or a cyclopentene derivative IIb.

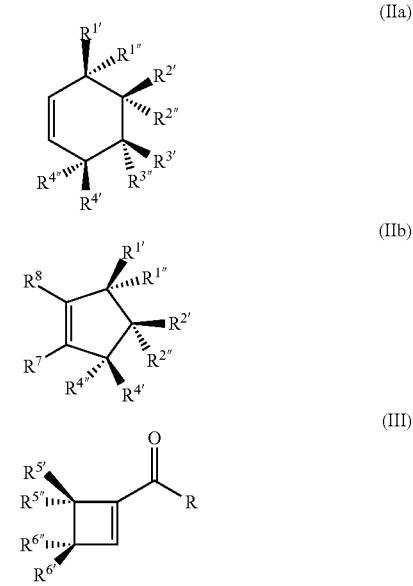

The method comprises contacting the cyclohexene derivative IIa or the cyclopentene derivative IIb with the cyclobutene derivative III in the presence of an olefin metathesis catalyst. This polymerization method enables the facile preparation of amphiphilic and bifunctional alternating polymers from simple and readily available starting materials.

The invention further provides novel polymers comprising the repeating unit Ia or Ib. According to the invention, polymers of the invention are used to inhibit microbial growth. Further, the polymers of the invention are useful for drug delivery.

DETAILED DESCRIPTION OF THE INVENTION

Figure 1:
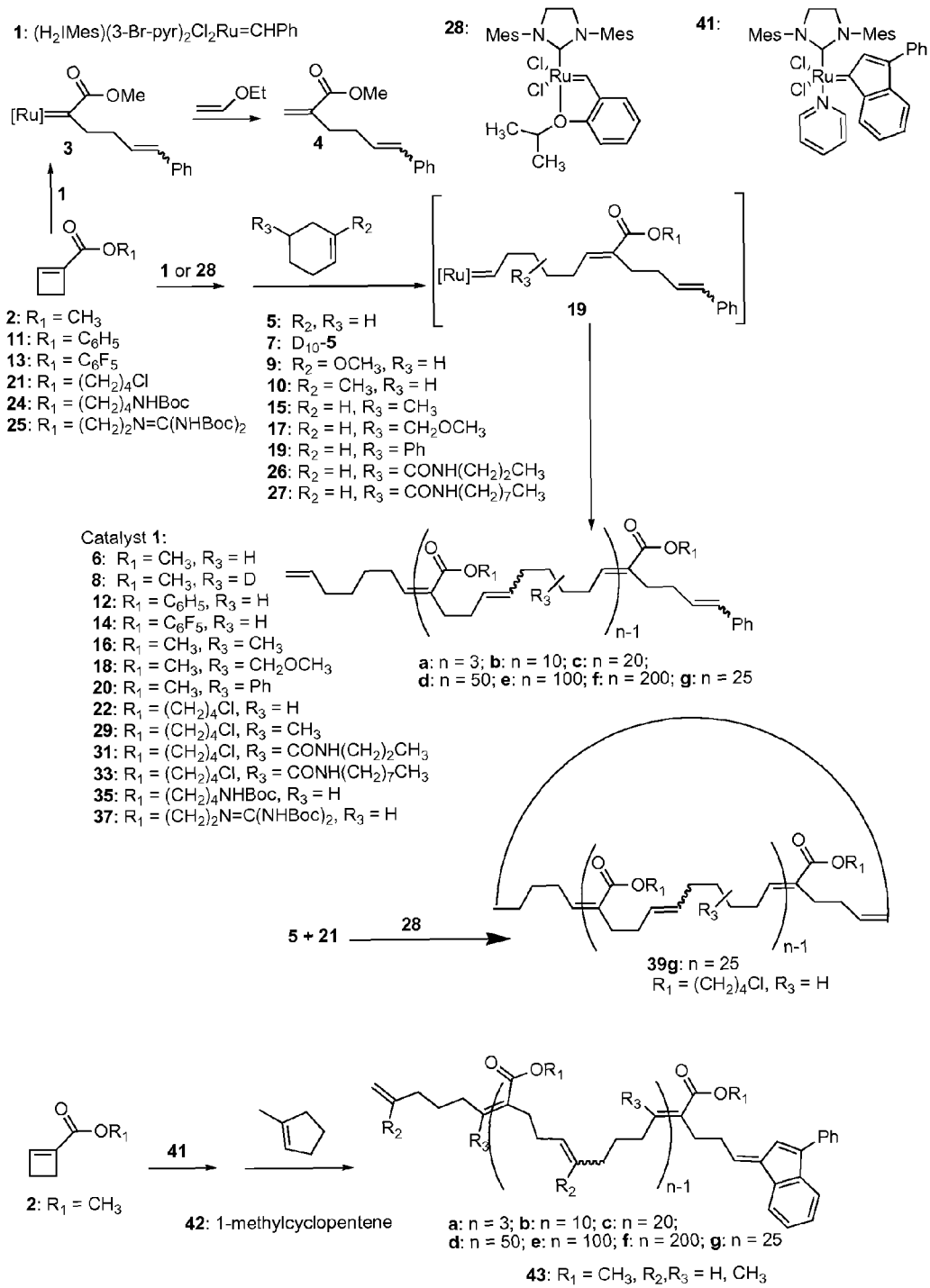
FIG. 1 shows the reaction scheme for preparation of the polymers of the invention.

The invention provides a method for producing a polymer comprising the repeating unit Ia or Ib:

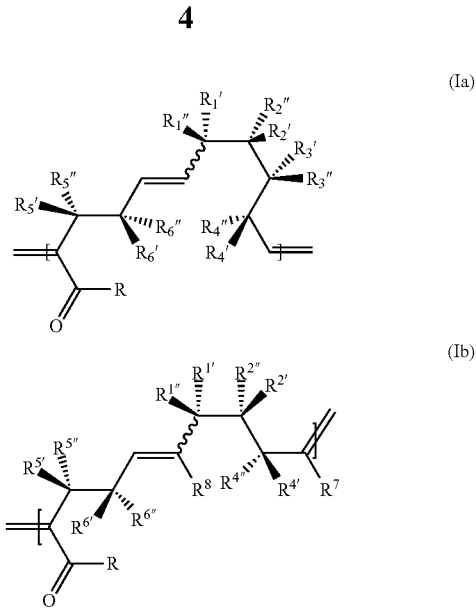

which comprises contacting an olefin of structure IIa or IIb with a cyclobutene of structure III

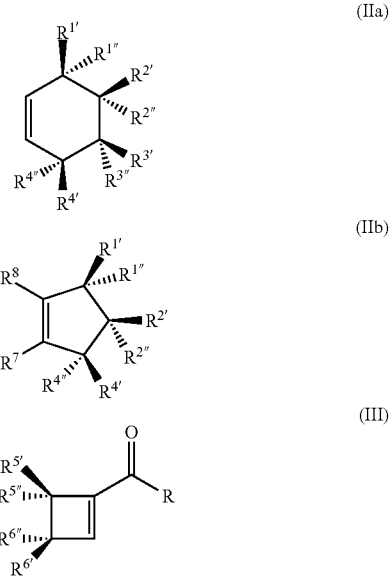

in the presence of an olefin metathesis catalyst. In the above structures, R may be, but is not limited to, H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkylthio, $C_2$-$C_{20}$ alkenyloxy, $C_2$-$C_{20}$ alkenylthio, $C_3$-$C_6$ cycloalkyloxy, $C_3$-$C_6$ cycloalkylthio, aryloxy, arylthio, heterocyclyloxy, or heterocyclylthio.

Each substituent $R^{1'}$ and $R^{1'''}$ through $R^{6'}$ and $R^{6'''}$ may independently be, but is not limited to, H, $C_1$-$C_{20}$ alkyl, $C_2$-$C_{20}$ alkenyl, $C_3$-$C_6$ cycloalkyl, $C_1$-$C_{20}$ hetero-substituted alkyl, aryl, heterocyclyl, aralkyl, $C_1$-$C_{20}$ alkoxy, $C_2$-$C_{20}$ alkenyloxy, $C_3$-$C_6$ cycloalkyloxy, aryloxy, heterocyclyloxy, or halogen. Additionally adjacent pairs of substituents, such as $R^1$—$R^2$, $R^2$—$R^3$, $R^3$—$R^4$, and $R^5$—$R^6$, together with the carbons to which they are attached, may form a carbocyclic or heterocyclic ring.

Additionally adjacent pairs of substituents, such as $R^{1'}$—$R^{2'}$, $R^{2'}$—$R^{3'}$, $R^{3'}$—$R^{4'}$, and $R^{5'}$—$R^{6'}$, together with the carbons to which they are attached, may form a carbocyclic or heterocyclic ring.

$R^7$ and $R^8$ may independently be, but are not limited to H, $C_1$-$C_{20}$ alkyl, $C_1$-$C_{20}$ hetero-substituted alkyl, $C_3$-$C_6$ cycloalkyl, aryl, heterocyclyl, $C_1$-$C_{20}$ alkoxy, $C_1$-$C_{20}$ acyloxy, $C_1$-$C_{20}$ substituted-amino, $C_1$-$C_{20}$ protected-amino, $C_3$-$C_6$ cycloalkyloxy, aryloxy, heterocyclyloxy, or halogen.

By way of example, suitable cyclohexene and cyclobutene species include but are not limited to the following:

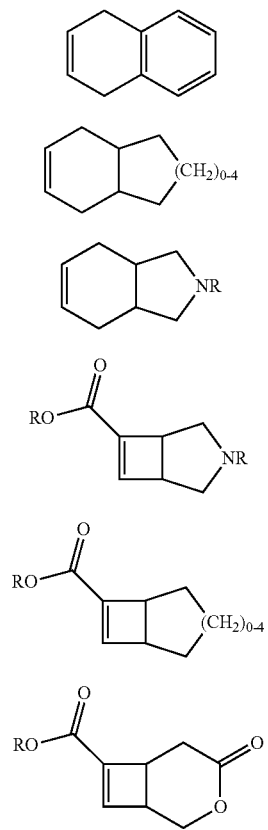

It will be understood that olefins in the substituents should be essentially unreactive with the metathesis catalyst under the reaction conditions, so that the metathesis polymerization involves the cyclobutene and cyclohexene or cyclopentene double bonds exclusively, or nearly so. Generally, any carbon-carbon double bonds in R, $R^{1'}$ and $R^{1'''}$ through $R^{6'}$ and $R^{6'''}$, $R^7$ and $R^8$ should be trisubstituted or tetrasubstituted, or otherwise rendered unreactive with the catalyst.

Aryl, as used herein, includes but is not limited to substituted or unsubstituted single-ring aromatic groups (i.e., phenyl,) and substituted or unsubstituted polycyclic ring systems (i.e., naphthyl, anthracenyl, phenanthryl groups and fullerenes, etc.). The polycyclic rings may have two or more rings in which two atoms are common to two adjoining rings (the rings are "fused") wherein at least one of the rings is an aryl group, e.g., the other rings can be cycloalkyls, aryl, heterocycles and/or heteroaryls. Aryl groups may have from 5 to 60 ring atoms, and preferably from 6 to 20 ring atoms. The aryl group may be optionally substituted with one or more substituents.

Heterocycle and heterocyclyl refer to substituted or unsubstituted monocyclic and substituted or unsubstituted fused polycyclic heteroaromatic and heteroaliphatic ring systems containing at least one N, O, S, or P atom. Heterocyclic groups may contain from 3 to 60 ring atoms, and preferably from 5 to 20 ring atoms. Heterocyclic groups and may include furan, thiophene, pyrrole, imidazole, oxazole, thiazole, triazole, pyrazole, pyridine, pyrazine, pyridazine, to large chromophores such as phthalocyanines. The heterocyclic group may be optionally substituted with one or more substituents.

The term "halo" or "halogen" as used herein includes fluorine, chlorine, bromine and iodine.

The term "alkyl" as used herein contemplates substituted or unsubstituted, straight and branched chain alkyl radicals containing from one to twenty carbon atoms. The alkyl group may be optionally substituted with one or more substituents.

The term "hetero-substituted alkyl" as used herein refers to straight and branched chain alkyl radicals containing from one to twenty carbon atoms which are bonded through, interrupted by, a hetero atom. The hetero-substituted alkyl group may additionally be further substituted.

The term "alkenyl" as used herein contemplates substituted or unsubstituted, straight and branched chain alkene radicals containing from two to twenty carbon atoms and one or more double bonds between two adjacent carbon atoms. An alkenyl group may be optionally substituted with one or more substituents. If an alkenyl group is present as a substituent on the cyclobutene III, cyclopentene IIb or cyclohexene IIa, it is preferable that the double bond(s) should be trisubstituted or tetrasubstituted, or otherwise rendered substantially unreactive with the catalyst.

The term "cycloalkyl" as used herein contemplates substituted or unsubstituted cyclic alkyl radicals containing form 3 to 8 carbon atoms and includes cyclopropyl, cyclobutyl, cyclopentyl, cyclohexyl, and the like. A cycloalkyl group may be optionally substituted with one or more substituents.

The term "aralkyl" as used herein contemplates an alkyl group which has as a substituent an aryl group. Both the alkyl portion and the aryl portion of the aralkyl group may optionally be further substituted with one or more substituents.

It will be apparent that alkyl, alkenyl, cycloalkyl, heterocyclyl, and aryl moieties in the substituents R, $R^{1'}$ and $R^{1'''}$ through $R^{6'}$ and $R^{6'''}$, $R^7$ and $R^8$ may be optionally substituted with functional groups known to be compatible with the catalyst. Examples include, but are not limited to, $C_1$-$C_4$ acyl, acyloxy, alkoxy and alkylthio groups, halogens, $C_1$-$C_4$ alkyl, aryl, protected amino groups such as BocNH— and FmocNH—, protected hydroxy groups such at TMSO—, BzO—, and BnO—, and protected carboxyl groups such as —$CO_2$-t-Bu and —$CO_2$Bn. Accordingly, the terms alkyl, alkenyl, cycloalkyl, aryl, and heterocyclyl as used herein encompass such substituents.

All value ranges are inclusive over the entire range. Thus, a range of 0 to 4 would include the values 0, 1, 2, 3 and 4.

The method may be used to prepare block copolymers as well; the proportion of alternating and block copolymer regions in the polymer being dependent upon the catalyst and substrate. The catalyst may be any olefin metathesis catalyst known in the art. It is preferably an alkylidene ruthenium complex of formula (L)(L')$X_2$Ru=CHR' or (L)$_2$(L')$X_2$Ru=CHR', wherein R' may be, for example, H, $C_1$-$C_{10}$ alkyl, $C_2$-$C_{10}$ alkenyl, $C_3$-$C_6$ cycloalkyl, and aryl. The ligand L is typically a trialkyl phosphine, triarylphosphine, tri(cycloalkyl)phosphine, a pyridine, or derivatives thereof, and, when R' is aryl, L may be an ortho alkoxy substituent on R'. L' is a second ligand, and may be a trialkyl phosphine, triarylphosphine, tri(cycloalkyl)phosphine, a pyridine, or derivatives thereof. L' may also be an imidazolin-2-ylidine carbene of formula

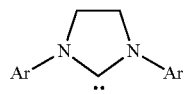

wherein Ar is an aryl group, particularly ortho-substituted aryl. The halogen X may be F, Cl, or Br, and is preferably Cl.

Preferably, at least one of L and L' is a pyridine. Pyridine and bromopyridine are particularly preferred. In other embodiments, one of L and L' may be trialkyl phosphine, more preferably a hindered trialkylphosphine such as tricyclohexylphosphine, tricyclopentylphosphine, or triisopropylphosphine. In certain embodiments, it is preferred that L is triphenylphosphine. In another embodiments, L' is an imidazolin-2-ylidine carbene and Ar is mesityl, 2-methylphenyl, 2-ethylphenyl, 2-isopropylphenyl, 2,3-diisopropylphenyl, 2,6-difluorophenyl, or 3,5-di-t-butylphenyl.

In alternative embodiments, the catalyst may be a molybdenum or tungsten metathesis catalyst, such as are known in the art (e.g., U.S. Pat. Nos. 4,590,174 and 6,433,113; see also D. Astruc, *New J. Chem.*, 2005, 29, 42-56.).

The invention also provides a polymer comprising the repeating unit Ia or Ib.

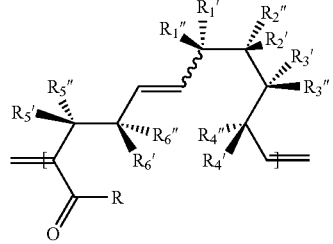

wherein R and $R^{1'}$ and $R^{1''}$ through $R^{6'}$ and $R^{6''}$ are as defined above. The polymer may, in certain embodiments, be a block copolymer, wherein one of the block types consists of repeating units of Ia or Ib.

The polymers of the present invention may be prepared according to the representative Schemes I to IV below:

Scheme I

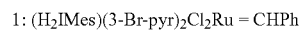

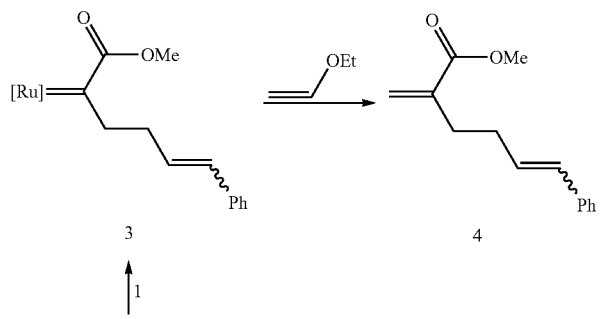

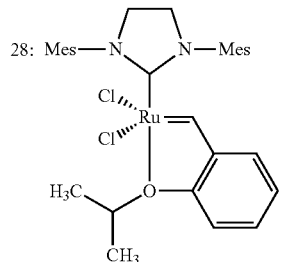

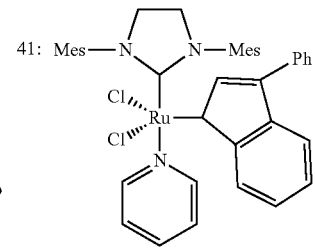

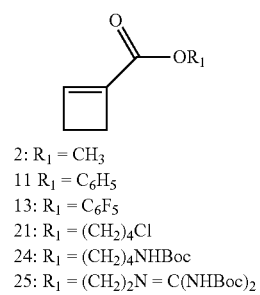

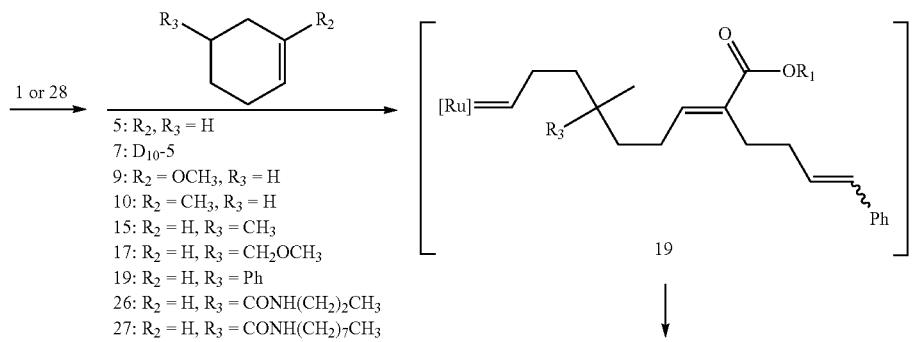

-continued

Catalyst 1:
6: $R_1 = CH_3$, $R_3 = H$
8: $R_1 = CH_3$, $R_3 = D$
12: $R_1 = C_6H_5$, $R_3 = H$
14: $R_1 = C_6F_5$, $R_3 = H$
16: $R_1 = CH_3$, $R_3 = CH_3$
18: $R_1 = CH_3$, $R_3 = CH_2OCH_3$
20: $R_1 = CH_3$, $R_3 = Ph$
22: $R_1 = (CH_2)_4Cl$, $R_3 = H$
29: $R_1 = (CH_2)_4Cl$, $R_3 = CH_3$
31: $R_1 = (CH_2)_4Cl$, $R_3 = CONH(CH_2)_2CH_3$
33: $R_1 = (CH_2)_4Cl$, $R_3 = CONH(CH_2)_7CH_3$
35: $R_1 = (CH_2)_4NHBoc$, $R_3 = H$
37: $R_1 = (CH_2)_2N=C(NHBoc)_2$, $R_3 = H$

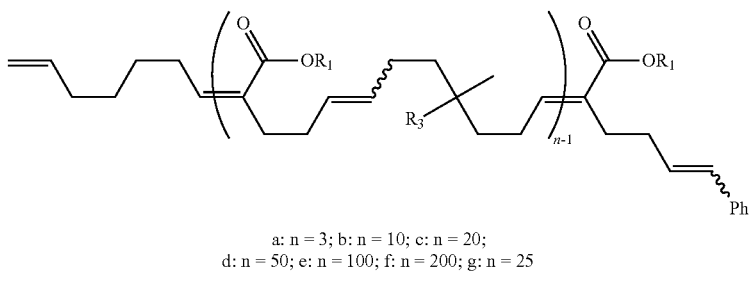

a: n = 3; b: n = 10; c: n = 20;
d: n = 50; e: n = 100; f: n = 200; g: n = 25

Scheme II $5 + 21 \xrightarrow{28}$

Scheme III

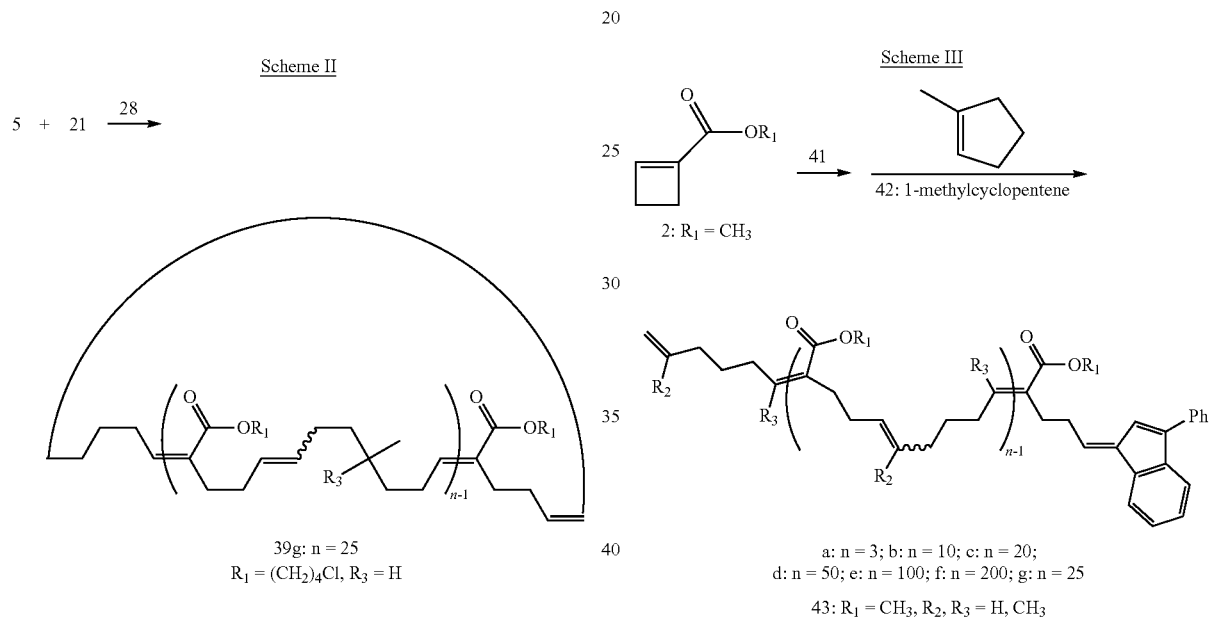

2: $R_1 = CH_3$

42: 1-methylcyclopentene

39g: n = 25
$R_1 = (CH_2)_4Cl$, $R_3 = H$ a: n = 3; b: n = 10; c: n = 20;
d: n = 50; e: n = 100; f: n = 200; g: n = 25

43: $R_1 = CH_3$, $R_2, R_3 = H, CH_3$

Scheme IV

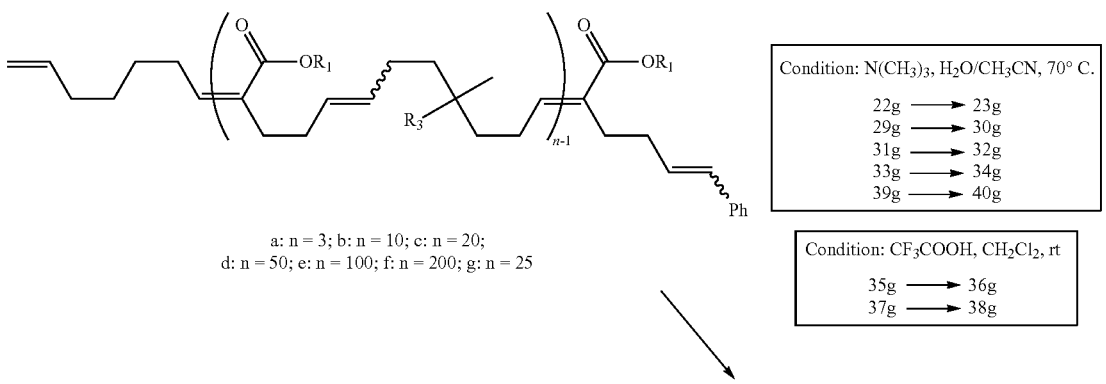

a: n = 3; b: n = 10; c: n = 20;
d: n = 50; e: n = 100; f: n = 200; g: n = 25

Condition: $N(CH_3)_3$, $H_2O/CH_3CN$, 70° C.
22g → 23g
29g → 30g
31g → 32g
33g → 34g
39g → 40g Condition: $CF_3COOH$, $CH_2Cl_2$, rt
35g → 36g
37g → 38g Catalyst 1:
- 22: $R_1 = (CH_2)_4Cl$, $R_3 = H$
- 29: $R_1 = (CH_2)_4Cl$, $R_3 = CH_3$
- 31: $R_1 = (CH_2)_4Cl$, $R_3 = CONH(CH_2)_2CH_3$
- 33: $R_1 = (CH_2)_4Cl$, $R_3 = CONH(CH_2)_7CH_3$
- 35: $R_1 = (CH_2)_4NHBoc$, $R_3 = H$
- 37: $R_1 = (CH_2)_2N=C(NHBoc)_2$, $R_3 = H$ Catalyst 28:
- 39: $R_1 = (CH_2)_4Cl$, $R_3 = H$

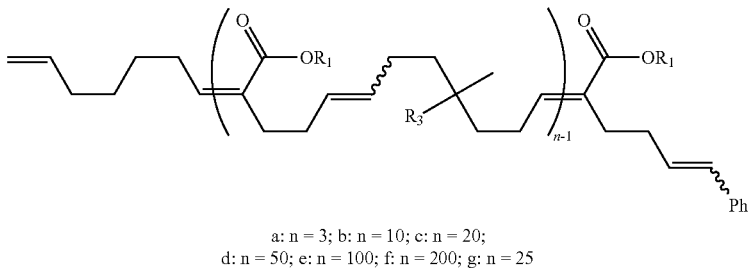

-continued a: n = 3; b: n = 10; c: n = 20;
d: n = 50; e: n = 100; f: n = 200; g: n = 25

Catalyst 1:
- 23: $R_1 = (CH_2)_4N(CH_3)_3{}^+Cl^-$, $R_3 = H$
- 30: $R_1 = (CH_2)_4N(CH_3)_3{}^+Cl^-$, $R_3 = CH_3$
- 32: $R_1 = (CH_2)_4N(CH_3)_3{}^+Cl^-$, $R_3 = CONH(CH_2)_2CH_3$
- 34: $R_1 = (CH_2)_4N(CH_3)_3{}^+Cl^-$, $R_3 = CONH(CH_2)_7CH_3$
- 36: $R_1 = (CH_2)_4NH_3{}^+CF_3COO^-$, $R_3 = H$
- 38: $R_1 = (CH_2)_2NH=C(NH_2)_2{}^+CF_3COO^-$, $R_3 = H$ Scheme V

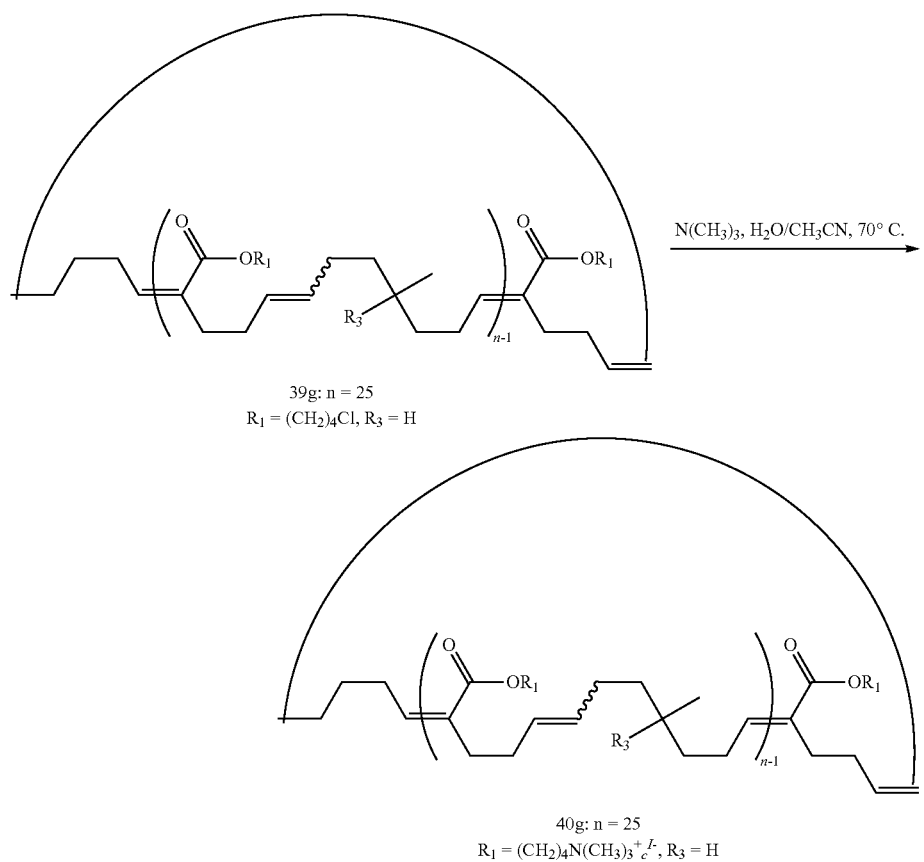

Cyclobutene 1-carboxamides are known to undergo ruthenium-catalyzed ring-opening metathesis to yield translationally invariant polymers. Lee, J. C.; Parker, K. A.; Sampson, N. S. *Journal of the American Chemical Society* 2006, 128, 4578-4579. The present inventors have surprisingly discovered that in the ROMP of cyclobutenecarboxylic acid derivatives with precatalyst 1, cyclobutene methyl ester 2 undergoes ring-opening metathesis without polymerization to afford, with 10 mole % of catalyst, approximately 10% of the α-methylene ester 4 (FIG. 1). As in the ring-opening metathesis of 1-substituted cyclobutene amides, the ring-opening metathesis is regiospecific. However with ester 2, the resulting enoic ruthenium carbene 3 does not react with additional substrate; rather, it survives to react with the quenching agent, providing ester 4.

Cyclohexene is not a ring-opening metathesis substrate when treated with ruthenium catalyst alone (K. J. Ivin, J. C. Mol, *Olefin Metathesis and Metathesis Polymerization*, 2nd edition, Academic Press, San Diego 1997), although it does undergo ring opening cross metathesis with acrylates. Choi, T. L.; Lee, C. W.; Chatterjee, A. K.; Grubbs, R. H. *Journal of the American Chemical Society* 2001, 123, 10417-10418; Fomine, S.; Tlenkopatchev, M. A. *Organometallics* 2007, 26, 4491-4497. It has now been discovered that when cyclobutene ester 2 and cyclohexene 5 are combined with precatalyst 1, alternating ring-opening metathesis polymerization (AROMP, Scheme 1) ensues with regio- and stereoregular ring-opening of ester 2, as shown by $^1$H-NMR and $^{13}$C-NMR spectroscopic analysis. Copolymers ranging in length from 3 A/B to 200 A/B units are obtained with 97%-75% conversion (6a-6f, Table 1). For each of the polymers, the relative intensities of the phenyl and vinyl protons are consistent with polymer 6 containing nearly equal amounts of repeating units A and B generated from monomers 2 and 5, respectively.

Figure 2:
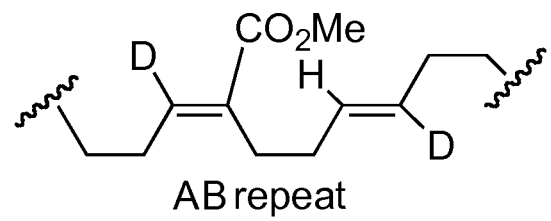
FIG. 2 shows the substructures in the alternating and block copolymers.
Figure 2:
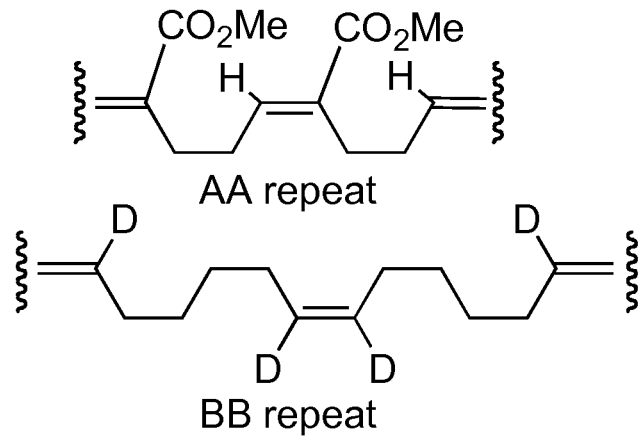

An isotopic labeling experiment was conducted to ascertain whether any block copolymer was formed during the course of copolymerization. In an alternating AB structure, the trisubstituted olefinic protons ($\delta$=6.8 ppm) originate from the cyclohexene, whereas the disubstituted olefinic protons ($\delta$=5.4 ppm) derive from both cyclohexene and cyclobutene 2 in an n:n−1 molar ratio. In a polyA structure, the trisubstituted olefinic protons ($\delta$=6.8 ppm) derive from cyclobutene 2. Analogously, in a polyB structure, the disubstituted olefins originate entirely from cyclohexene (FIG. 2).

Figure 3:
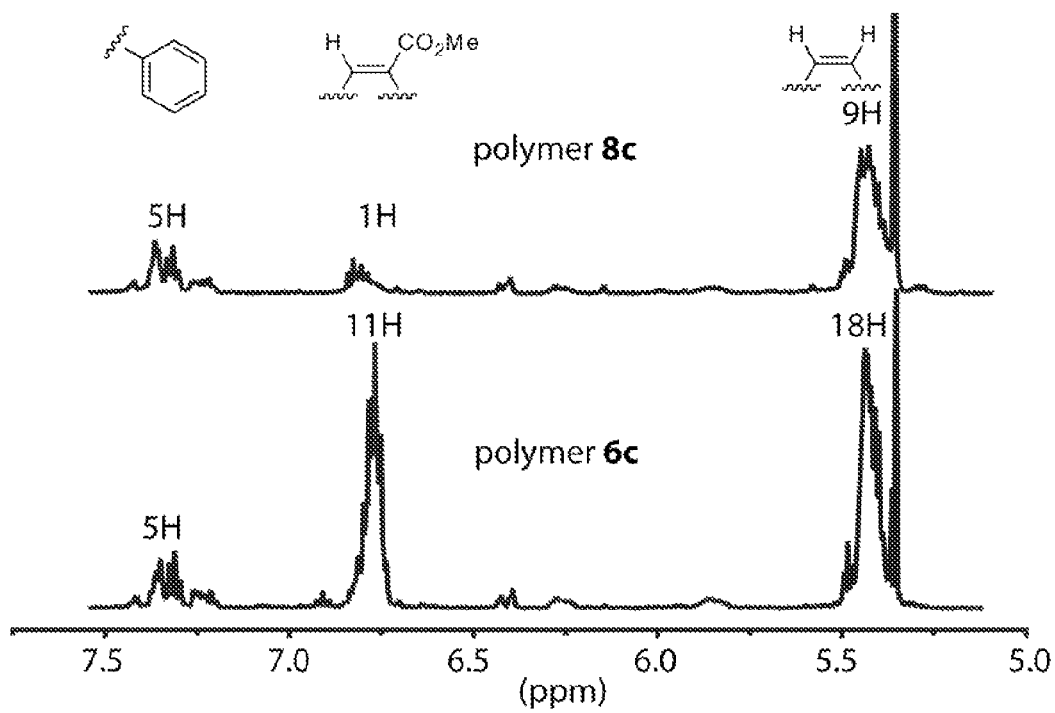
FIG. 3 shows a representative NMR spectrum and illustrates the method for determining the relative amounts of alternating and block copolymer components.

Cyclohexene-D$_{10}$, 7, and cyclobutene 2 were subjected to AROMP, the $^1$H-NMR spectra of the crude polymers acquired, and the intensities of the olefinic peaks integrated against the phenyl end group (FIG. 3). As expected, for an alternating AB copolymer, the disubstituted olefinic proton peak ($\delta$=5.4 ppm) in the deuterated polymer 8c spectrum was reduced to half its original integrated intensity as compared to the spectrum of polymer 6c. Moreover, the trisubstituted olefinic proton peak ($\delta$=6.8 ppm) in the deuterated polymer spectrum was reduced to 9% of its original intensity in the undeuterated polymer spectrum (approaching 0%) as expected for an alternating AB copolymer. The percent of trisubstituted olefin that remained was constant regardless of the original A:B feed ratio in the AROMP reaction. Thus, 90% of the polymer backbone is of alternating structure with about 10% polyA formed during the polymerization. To further establish the alternating nature of the polymer backbone, $^1$H—$^1$H gCOSY spectroscopy was employed, and clear internal connectivity between repeating units A and B was observed.

Without being bound by theory, the present inventors believe that the key to alternation is the lack of reactivity of cyclohexene with the alkylidene 19 that results from reaction of cyclohexene with enoic carbene 3. Consistent with this lack of reactivity, cyclohexene incubated with precatalyst 1 does not generate any ring-opened product. Cross metathesis of cyclohexene and ester alkylidenes is thought to be favorable due to the coordination of the carbonyl oxygen atom to ruthenium, resulting in transition state stabilization. Fomine, S.; Tlenkopatchev, M. A. *Organometallics* 2007, 26, 4491-4497.

The ester moiety was varied to determine whether more electrophilic esters would be tolerated in AROMP. Electrophilic esters would allow later elaboration with additional functionality after polymerization. AROMP of 5 and either phenyl ester 11 or trifluorophenyl ester 13 proceeded with high conversion (>95%) at room temperature in 4 or 13 hours to yield 12c or 14b, respectively. Thus, functionally complex, alternating polymers may be prepared by AROMP.

With respect to substituents on the cyclohexene, both 9 and 10, when subjected to AROMP with 2 did not generate any polymer. However, substitution remote from the cyclohexene alkene is tolerated. Both 15 and 17 underwent AROMP with 2 to generate the corresponding alternating polymers, 16c and 18c, with 94% conversion in 4 hours. The integration ratio of the three alkene protons (6.8 ppm and 5.4 ppm) in the $^1$H-NMR spectra indicated that substitution of the cyclohexene at the 4-position did not interfere with alternation, and the percentage of alternating structure remained 90%. Diversely substituted cyclohexenes are readily available through Diels-Alder chemistry. Therefore the AROMP process of the present invention provides entry to copolymers of alternating functionality.

Figure 4:
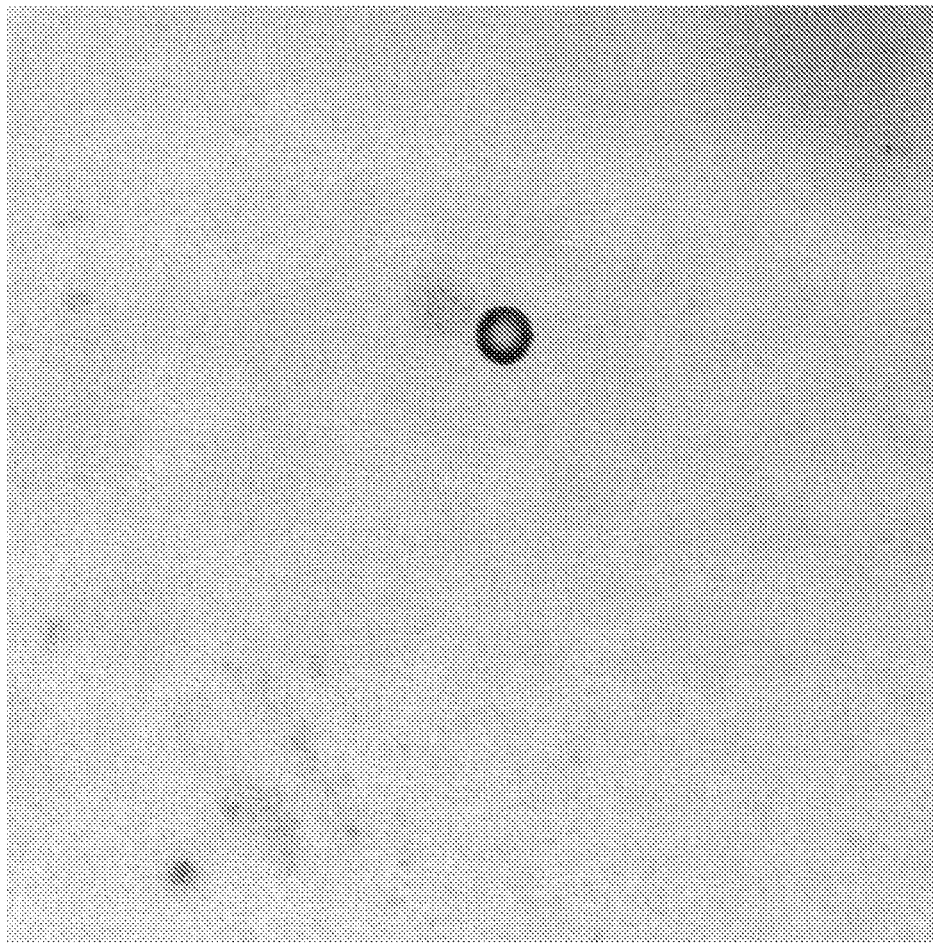
FIG. 4 is a TEM image showing the micelle-forming ability of a polymer of the invention.
Figure 5:
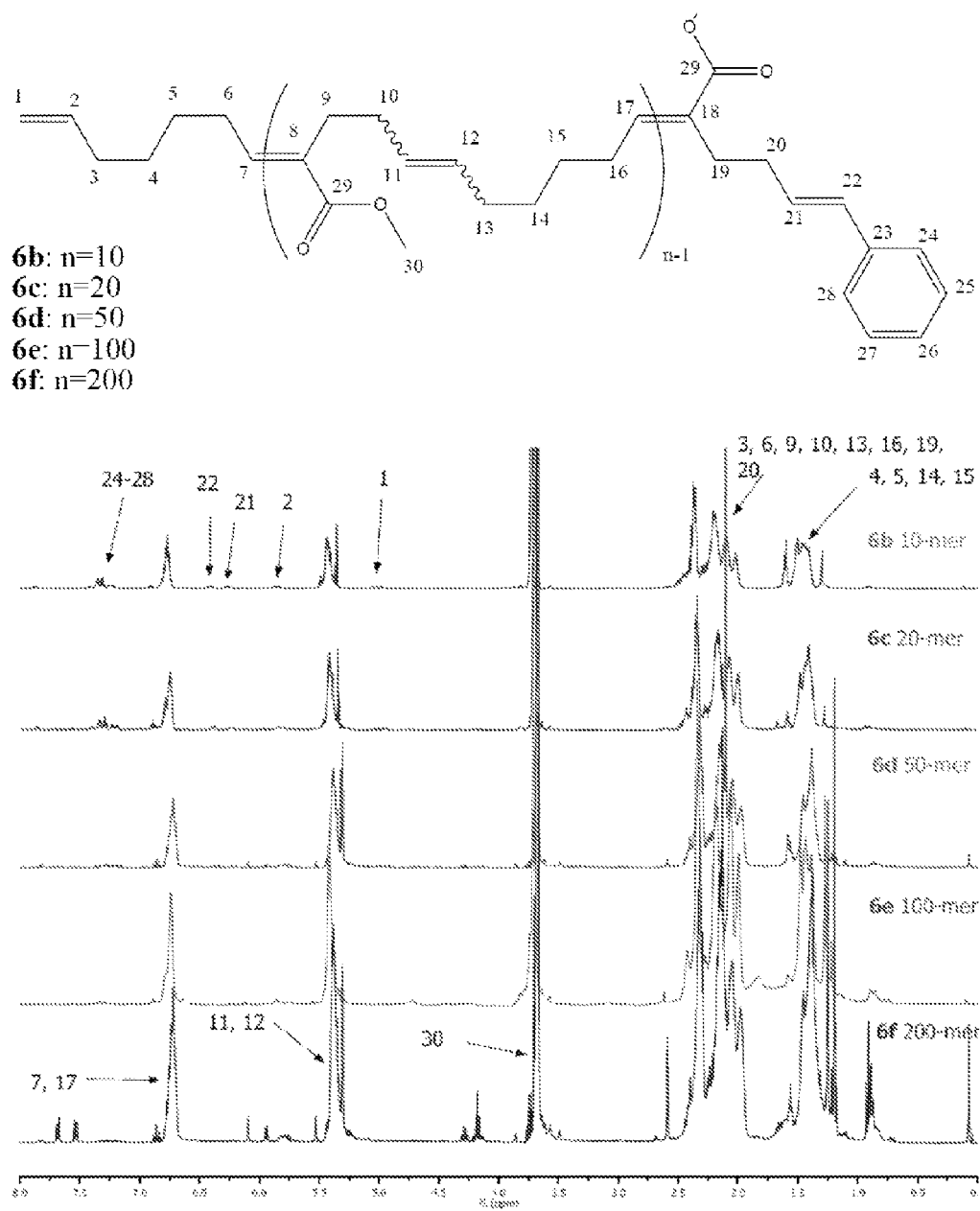
FIG. 5 depicts the $^1$H-NMR spectra of alternating ROMP polymers.
Figure 6:
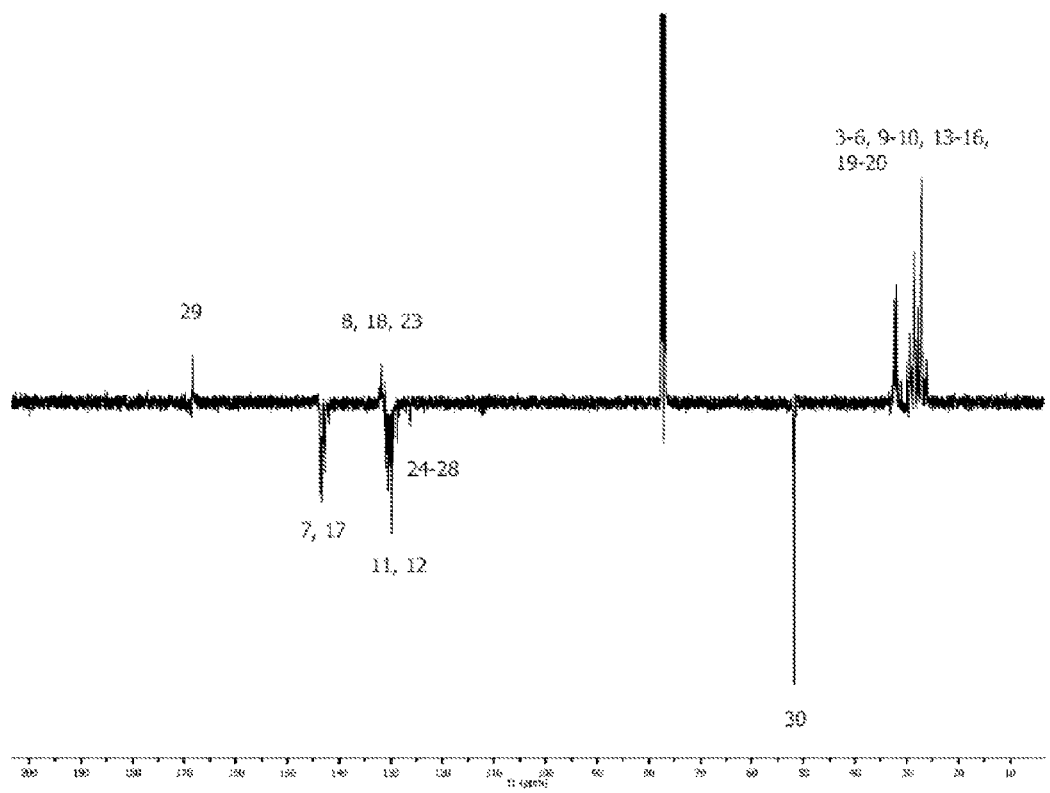
FIG. 6 depicts the $^{13}$C-APT-NMR spectrum of alternating ROMP polymer $(2\text{-}5)_{20}$.
Figure 7:
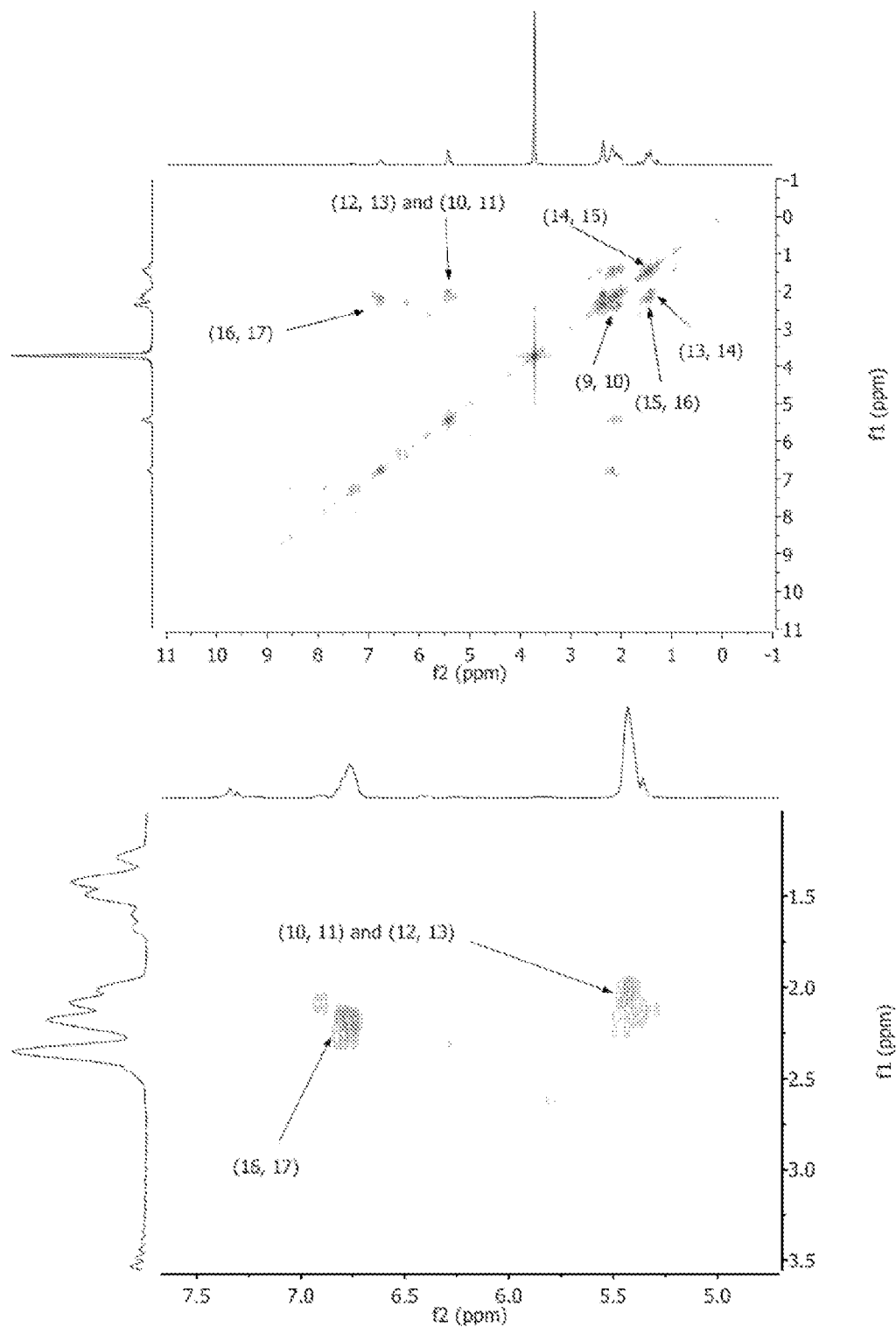
FIG. 7 depicts the $^1$H—$^1$H-gCOSY-NMR spectrum of alternating ROMP polymer $(2\text{-}5)_{20}$.
Figure 8:
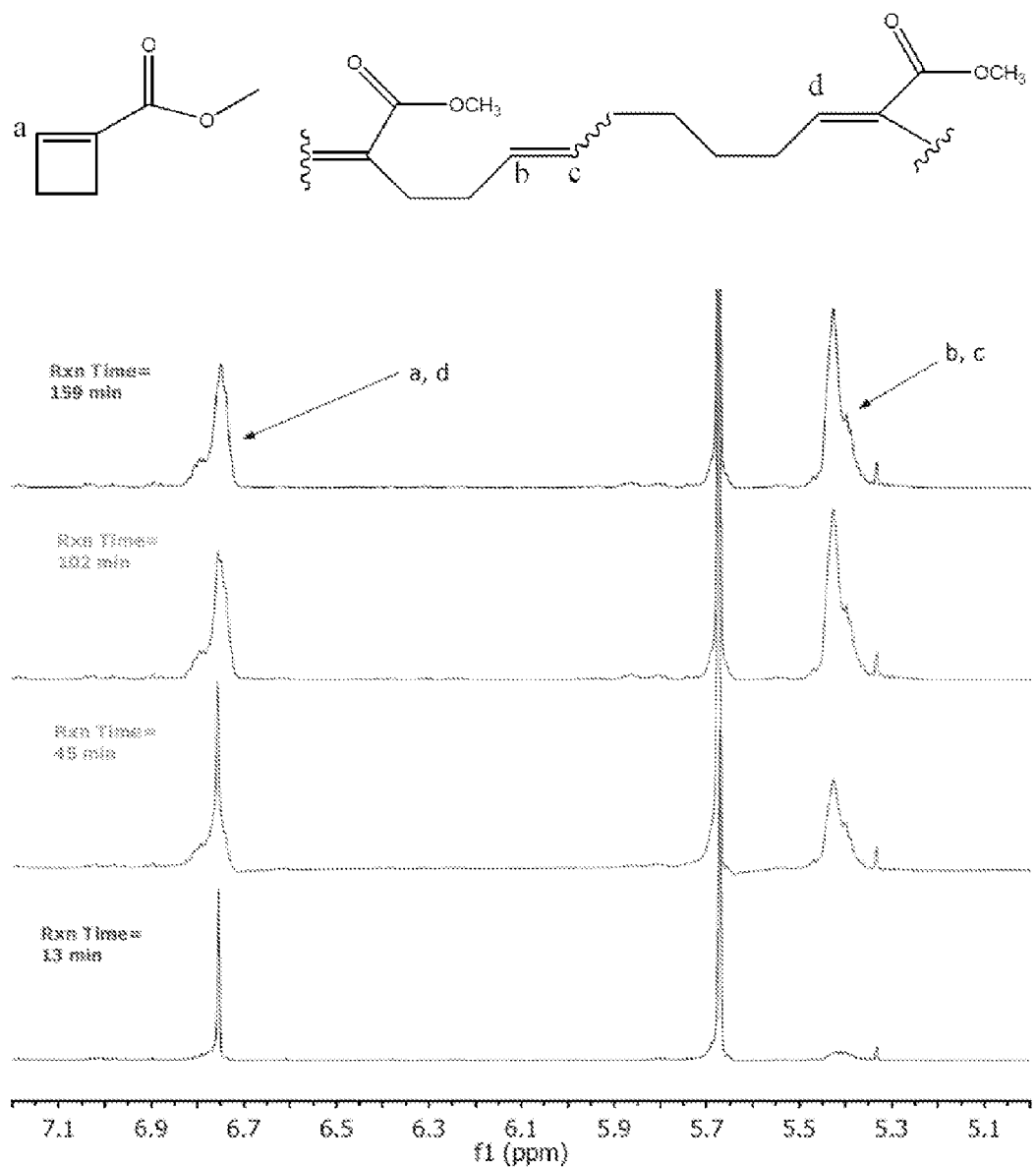
FIG. 8 depicts a kinetic NMR-monitoring experiment of $(2\text{-}5)_{100}$.
Figure 9:
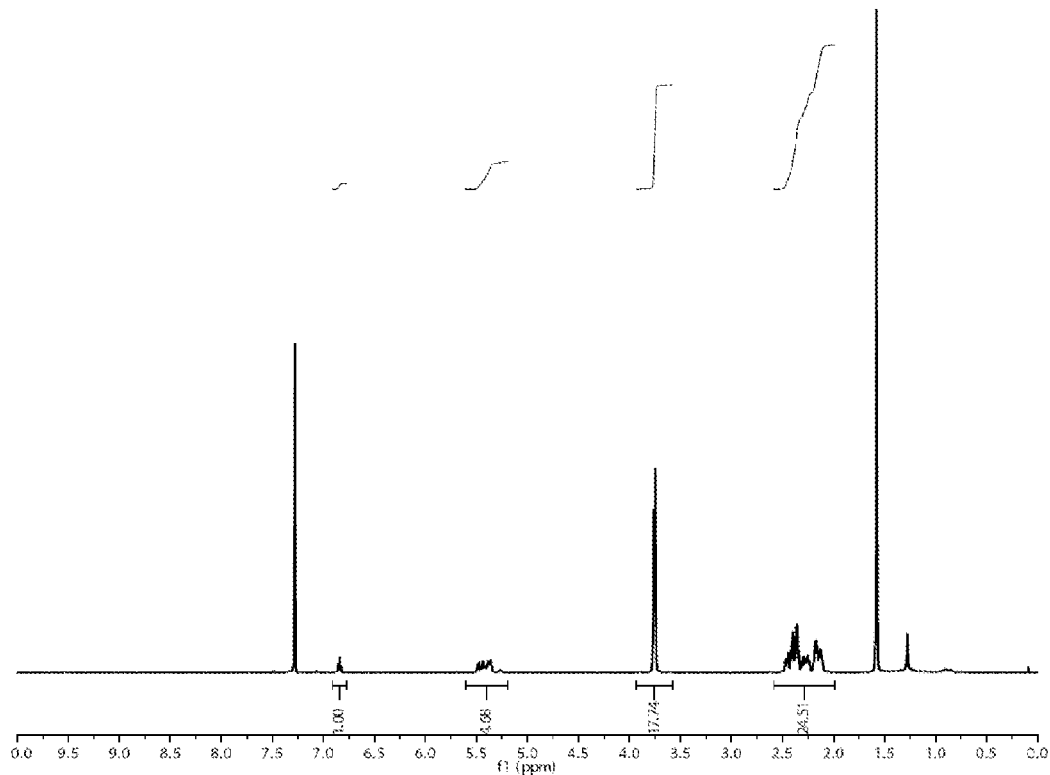
FIG. 9 depicts the $^1$H-NMR spectrum of cyclic polymer cyc-$(2\text{-}7)_{20}$.
Figure 9:
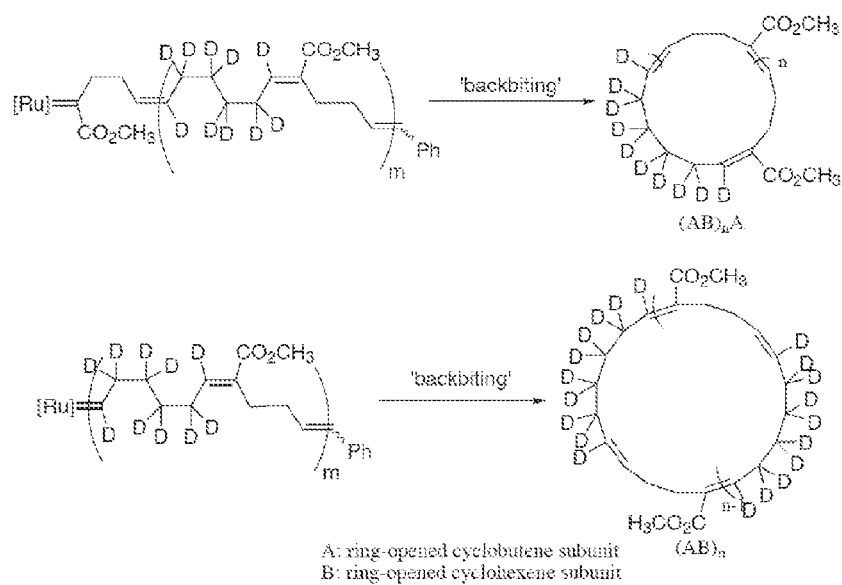

The invention thus provides a method for preparation of (AB)$_n$ heteropolymers with an alternating backbone and alternating functionality, from readily accessible starting monomers. These regioregular, alternating polymers, with directly-incorporated and highly varied functionality, are useful in a variety of applications, and can readily be modified post-polymerization. For example, the polymer 23g was prepared by nucleophilic displacement of chloride from polymer 22g. The amphiphilic polymer 23g self-assembles into supramolecular, spherical structures in aqueous solution, having an average diameter of 624 nm based on dynamic light scattering and transmission electron microscopy (see FIG. 4). Such structures have utility as drug delivery systems, and have antimicrobial activity (Table 2) and can be used to inhibit (i.e., prevent or reduce) microbial growth.

For example, in one embodiment, amphiphilic polymer-drug conjugates are produced which form a core-shell micellar structure in aqueous solution, with the hydrophobic drug-binding portion as the hydrophobic core and the hydrophilic portion as the hydrated outer shell. In another embodiment, an amphiphilic polymers of the invention is placed in solution with a desired drug substance, and micelle formation is induced in the solution, thereby incorporating the drug substance into the micelles. Specific targeting can be accomplished by conjugating specific ligands to the micelle polymers, prior to or after micelle formation.

Antimicrobial polymers of the invention can be used in solution, incorporated onto surfaces or included in bulk materials with retention of antimicrobial properties. Thus, they are suitable for coatings where microbial growth, including biofilm formation, is undesirable or must be avoided, including paints, glazes, textile coatings, fabric finishes, and the like. The polymers can be incorporated into articles such as door handles, railings, toilet or kitchen surfaces, materials for water-conveying parts such as pipes, seals, and valves. In one embodiment, the polymer coatings form the surface of a medical device or implant. In another embodiment, the medical device or implant is impregnated with a polymer of the invention. In certain embodiments, the antimicrobial surface inhibits the growth of microorganisms in the medium adjoining the surface, so that preservative packaging of easily spoiled aqueous goods is also possible without the need for addition of toxic or unsafe substances.

Alternating copolymers with regularly spaced hole-transport and emitting chromophores are useful in organic light-emitting devices, and alternating copolymers containing both donor and acceptor moieties have potential for use in photovoltaic devices. The methods and polymers of the present invention will make such structures much more readily accessible.

TABLE 1

AROMP Polymer Preparations[a]

| A | B | [Ru] (M) | [A]:[B]:[Ru] | Reaction time (h) | Product | % conv.[b] |
|---|---|---|---|---|---|---|
| 2 | none | 0.01 | 10:0:1 | 5 | 4 | 10 |
| 2 | none | 0.067 | 1:0:1.5 | 20 | 4 | 55[c] |
| 2 | 5 | 0.05 | 3:6:1 | 6 | 6a | 74[c] |
| 2 | 5 | 0.01 | 10:20:1 | 3 | 6b | 98 |
| 2 | 5 | 0.01 | 20:40:1 | 3 | 6c | 98 |
| none | 5 | 0.01 | 0:40:1 | 6 | NR[d] | 0 |
| 2 | 5 | 0.01 | 50:100:1 | 3 | 6d | 98 |
| 2 | 5 | 0.01 | 100:200:1 | 3 | 6e | 97 |
| 2 | 5 | 0.005 | 200:400:1 | 6 | 6f | 73 |
| 2 | 5 | 0.01 | 200:400:1 | 6 | 6f | 75 |
| 2 | 7 | 0.01 | 20:24:1 | 3 | 8c | 97 |
| 2 | 7 | 0.01 | 20:40:1 | 3 | 8c | 97 |
| 2 | 7 | 0.01 | 20:160:1 | 3 | 8c | 97 |
| 2 | 9 | 0.01 | 10:20:1 | 3 | NR | 0 |
| 2 | 10 | 0.01 | 10:20:1 | 3 | NR | 0 |
| 11 | 5 | 0.01 | 20:40:1 | 4 | 12c | 96 |
| 13 | 5 | 0.01 | 10:20:1 | 13 | 14b | 95 |
| 2 | 15 | 0.01 | 20:40:1 | 4 | 16c | 95 |
| 2 | 17 | 0.01 | 20:40:1 | 4 | 18c | 95 |
| 2 | 19 | 0.01 | 20:40:1 | 6 | 20c | 90 |
| 21 | 5 | 0.01 | 25:50:1 | 5 | 22g | 90 |
| 21 | 15 | 0.01 | 25:50:1 | 3[e] | 29g | 94 |
| 21 | 26 | 0.01 | 25:50:1 | 3[e] | 31g | 92 |
| 21 | 27 | 0.01 | 25:50:1 | 5[e] | 33g | 96 |
| 24 | 5 | 0.01 | 25:50:1 | 1.5[e] | 35g | 97 |
| 25 | 5 | 0.01 | 25:50:1 | 1.5[e] | 37g | 97 |
| 21 | 5 | 0.01 | 25:50:1 | 5[f] | 39g | 90 |
| 21 | 42 | 0.01 | 20:40:1 | 3[g] | 43c | 50 |

[a]AROMP reactions were performed in $CD_2Cl_2$ and monitored by $^1$H-NMR spectroscopy at room temperature.
[b]Percent conversion determined by integration of 1H-NMR spectra unless specified otherwise.
[c]AROMP reactions were performed in $CH_2Cl_2$, and the isolated yield was determined after flash column chromatography purification.
[d]NR: no reaction.
[e]Reaction temperature: 50° C., solvent: $CDCl_3$
[f]Catalyst: Hoveyda-Grubbs 2nd Generation catalyst 28
[g]Reaction temperature: 50° C., solvent: $CDCl_3$, Catalyst: 41

TABLE 2

Minimum Inhibitory Concentrations (MIC)[a] and $HC_{50}$[b]

| Strain | 23g (µg/mL) | 30g (µg/mL) | 32g (µg/mL) | 34g (µg/mL) | 40g (µg/mL) | 36g (µg/mL) | 38g (µg/mL) |
|---|---|---|---|---|---|---|---|
| *Pseudomonas aeruginosa* ATCC 27853 | 64 | >64 | >64 | >64 | >64 | 128 | 32 |
| *Escherichia coli* ATCC 25922 | 16 | 64 | >64 | >64 | >64 | 64 | 8 |
| *Bacillus cereus* ATCC 10987 | 8 | 16 | >64 | 32 | 64 | 64 | 8 |
| *Staphylococcus aureus* ATCC 25923 | 4 | 8 | >64 | 32 | 16 | 32 | 4 |
| *Enterococcus faecalis* ATCC 19433 | 4 | 16 | >64 | 32 | 32 | 64 | 8 |
| *Enterococcus faecium* ATCC 19434 | 4 | 16 | >64 | 32 | 32 | 32 | 8 |
| $HC_{50}$ | 256 | 768 | >1024 | 192 | 1024 | 1024 | 512 |

[a]Indicated strains were incubated with an aqueous solution of 23g for 18 h, and the lowest concentration at which no growth is detected is reported.
[b]Hemolytic activity towards red blood cells ($HC_{50}$ = concentration at which 50% of blood cells are lysed)

EXAMPLES

Table 1 summarizes the results of several exemplary applications of the AROMP process of the invention. These results are presented by way of example only, and do not represent the scope of the invention.

Exemplary procedures for carrying out the invention are presented below.

General Information

All reactions were performed under an $N_2$ or Ar atmosphere. $CH_2Cl_2$ was dried in a GlassContour solvent pushstill system. $CD_2Cl_2$ was degassed before use for reactions. Second-generation Grubbs' catalyst [($H_2$IMes)($PCy_3$)($Cl$)$_2$Ru=CHPh], ethyl 1-bromo-cyclobutanecarboxylate and 3-cyclohexene-1-methanol were purchased from Aldrich (Cat #: 56974-7, 19729-7 and 162167). Cyclohexene 5, 1-methylcyclohexene 10, and 4-methyl-1-cyclohexene 15 were purchased from Fisher Scientific. Cyclohexene-$D_{10}$ 7 was purchased from CDN Isotope Inc. (Cat #D0173). The synthesis of precatalyst 1 was performed with the published procedure (Love, J. A.; Morgan, J. P.; Trnka, T. M.; Grubbs, R. H., *Angew Chem Int Edit* 2002, 41, 4035-4037.)

Mallinckrodt silica gel 60 (230-400 mesh) was used for column chromatography. Aluminum TLC (thin layer chromatography) plates were silica gel 60 (F254). $^1$H NMR spectra were reported as chemical shift in ppm (multiplicity, coupling constant in Hz, and integration). $^{13}$C NMR spectra were reported as chemical shift in ppm. The solvent peak was used as an internal reference.

LC-MS spectra were acquired on a Waters ACQUITY™ Ultra Performance Liquid Chromatography system with an SQD detector and using a 10 cm×2.1 mm ACQUITY™ 1.7 µm column (Waters Corp, Milford, Mass., USA) with elution by a linear gradient of 20-100% B at 0.5 ml/min, where A=water and B=methanol.

The molecular weights of the polymers were assessed by gel permeation chromatography (Phenogel 5µ MXL GPC column, Phenomenex) eluting with THF.

Cyclobut-1-enecarboxylic acid[2,3]

Cyclobut-1-enecarboxylic acid was prepared according to the procedure for preparation of 3,3-dimethylcylobutene carboxylic acid as described by Campbell et al. with minor modifications. KOH (6.00 g, 107 mmol) and toluene (90 ml) were mixed and then heated to reflux until the KOH dissolved. Ethyl 1-bromocyclobutanecarboxylate (4.90 g, 23.7 mmol) was added dropwise without heating. The reaction mixture was heated at reflux for 1 h, then cooled to RT. Cold water (60 ml) was added, the aqueous layer was washed with pentane (2×40 ml) and the pH was adjusted to 2.5 with 30% aq $H_2SO_4$. The product was then extracted from the aqueous layer with $Et_2O$ (4×40 ml) and dried over anhydrous $Na_2SO_4$. The $Et_2O$ was evaporated to give a yellow oil. The oil was dissolved in pentane (50 ml) and the upper layer was separated from the lower layer. The upper layer was cooled in an acetone-dry ice bath and stirred for 20 min. The resulting precipitate was filtered and dried under vacuum (1.14 g, 49% yield). The dried solid was stored at −20° C. to prevent decomposition. $^1$H-NMR (400 MHz, $CDCl_3$) δ 10.23 (bs, 1H), 6.94 (t, J=1.2 Hz, 1H), 2.76 (t, J=3.2 Hz, 2H), 2.51 (td, J=3.2 Hz, 1.2 Hz, 2H); $^{13}$C-NMR (100 MHz, $CDCl_3$) δ 167.5, 150.1, 138.4, 29.1, 27.5.

Methyl cyclobut-1-enecarboxylate, (2)[4,5]

The ester 2 was prepared according to the literature.[4,5] $_1$H-NMR (400 MHz, $CDCl_3$) δ 6.74 (s, 1H), 3.68 (s, 3H), 2.69 (m, 2H), 2.46 (m, 2H). $^{13}$C-NMR (150 MHz, $CDCl_3$) δ 162.7, 146.5, 138.8, 51.2, 29.3, 27.3.

1-Methoxycyclohexene, (9)[6-8]

Cyclohexanone (0.19 mol, 20 ml) and p-toluenesulfonic acid (0.97 mmol, 184 mg) were mixed together, and cooled to −20° C. Trimethoxymethane (0.21 mol, 23 ml) was added to the solution. The solution was warmed up to room temperature and was stirred for 24 h at rt. Then the solution was distilled first at normal pressure to remove $HCOOCH_3$ (32° C.), methanol (65° C.) and excess $CH(OCH_3)_3$ (102° C.). The remaining solution was distilled at 139 C at normal pressure to yield 9 (13 g, 61%) as a colorless liquid. $^1$H-NMR (500 MHz, $CDCl_3$) δ 4.55 (t, J=3.5 Hz, 1H), 3.42 (s, 3H), 2.00 (m, 4H), 1.62 (m, 2H), 1.50 (m, 2H). $^{13}$C-NMR (125 MHz, $CDCl_3$) δ 157.9, 95.5, 56.1, 30.3, 26.0, 25.5, 25.4. LC-MS (APCI): Peak time=1.59 min, m/z calcd for $C_7H_{13}O$ [M+H]$^+$ 113.09, found 113.08.

Phenyl cyclobut-1-enecarboxylate, (11)

Cyclobut-1-enecarboxylic acid (0.51 mmol, 50 mg) was dissolved in 0.5 ml dry $CH_2Cl_2$. The solution was cooled to 0° C. and oxalyl dichloride (0.51 mmol, 43 μl) was added. The temperature of the solution was raised to room temperature, and the mixture was allowed to react for 1 h. The solvent was evaporated to generate a viscous oil. Phenol (0.51 mmol, 48 mg) and triethylamine (1.02 mmol, 142 μl) were dissolved in 0.5 ml dry $CH_2Cl_2$, and the solution was stirred at 0° C. for 45 min before being added to a vial containing the cyclobut-1-enecarboxylic chloride. The reaction mixture was stirred for 16 h at rt. The reaction was quenched with 1 N HCl, and was extracted with $CH_2Cl_2$ (30 ml). The $CH_2Cl_2$ solution was washed with 5% $NaHCO_3$ (2×10 ml), dried over $Na_2SO_4$, concentrated by rotary evaporation, and then purified by flash column chromatography (100% $CH_2Cl_2$) to yield 11 as a colorless oil (42 mg, 47%). $^1$H-NMR (100 MHz) δ 7.42 (m, 2H), 7.28 (m, 1H), 7.14 (m, 2H), 7.02 (s, 1H), 2.88 (t, J=3.0 Hz, 2H), 2.60 (m, 2H). $^{13}$C-NMR (400 MHz) δ 160.5, 150.8, 149.2, 138.3, 129.6, 125.9, 121.8, 29.5, 27.7. HRMS (EI) calcd. for $C_{11}H_{10}O_2$ [M]$^+$ 174.0679, found 174.0681.

Perfluorophenyl cyclobut-1-enecarboxylate, (13)

Cyclobut-1-enecarboxylic acid (0.51 mmol, 50 mg) was dissolved in 0.5 ml dry $CH_2Cl_2$. The solution was cooled to 0° C. and oxalyl dichloride (0.51 mmol, 43 μl) was added. The temperature of the solution was raised to room temperature, and the mixture was allowed to react for 1 h. The solvent was evaporated to generate a viscous oil. 2,3,4,5,6-Pentafluorophenol (0.51 mmol, 94 mg) and triethylamine (1.02 mmol, 142 μl) were dissolved in 0.5 ml dry CH2Cl2, and the solution was stirred at 0° C. for 45 min before being added to a vial containing cyclobut-1-enecarboxylic chloride. The reaction mixture was stirred for 16 h at rt. The reaction was quenched with 1 N HCl, and was extracted with $CH_2Cl_2$ (30 ml). The $CH_2Cl_2$ solution was washed with 5% $NaHCO_3$ (2×10 ml), dried over $Na_2SO_4$, concentrated by rotary evaporation, and then purified by flash column chromatography (100% $CH_2Cl_2$) to yield 13 as a colorless oil (59 mg, 44%). $^1$H-NMR (500 MHz, $CDCl_3$) δ 7.12 (s, 1H), 2.86 (m, 2H), 2.60 (m, 2H). $^{13}$C-NMR (125 MHz, $CDCl_3$) δ 156.7, 152.6, 142.1, 140.3, 138.8, 138.3, 135.2, 53.3, 30.6, 29.2. HRMS (ESI) calcd. for $C_{11}H_6O_2F_5$ [M+H]$^+$ 265.0293, found 265.0288.

4-(Methoxymethyl)cyclohexene, (17)

3-Cyclohexene-1-methanol (8.92 mmol, 1.00 g) and NaH (17.8 mmol, 428 mg) were mixed in THF (30 mL) at rt, and the THF solution was stirred for 1 h at rt. MeI (17.8 mmol, 1.10 mL) was added slowly into the above THF solution. After stirring for 16 h at rt, the solution was diluted with water (30 ml), and then was extracted with diethyl ether (2×30 mL). The organic layer was dried over $Na_2SO_4$, was concentrated by rotary evaporation, and then was distilled to generate the final product 17 as a colorless liquid (460 mg, 41%). $^1$H-NMR (500 MHz) δ 5.68 (m, 2H), 3.36 (s, 3H), 3.28 (dd, J=6.5 Hz, J=4 Hz), 2.06-2.14 (m, 3H), 1.92 (m, 1H), 1.83 (m, 1H), 1.75 (m, 1H), 1.29 (m, 1H). $^{13}$C-NMR (100 MHz) δ 127.2, 126.1, 78.0, 58.9, 34.0, 28.6, 25.8, 24.7. LC-MS (APCI): Peak time=1.59 min, m/z calcd for $C_8H_{15}O$ [M+H]$^+$ 127.11, found 127.10.

Cyclobut-1-enecarboxylic acid 4-chloro-butyl ester, (21)

Cyclobut-1-enecarboxylic acid (2.04 mmol, 200 mg) was dissolved in 1.5 mL dry $CH_2Cl_2$. The solution was cooled to 0° C. and oxalyl dichloride (4.08 mmol, 345 μL) was added. The temperature of the solution was raised to rt, and the mixture was allowed to react for 1 h. The solvent was evaporated to generate a viscous oil. 4-chlorobutanol (1.36 mmol, 148 mg) and triethylamine (2.72 mmol, 379 μL) were dissolved in 1.0 mL dry $CH_2Cl_2$, and the solution was stirred at 0° C. for 45 min before being added to a vial containing cyclobut-1-enecarboxylic chloride. The reaction mixture was stirred for 16 h at rt. The $CH_2Cl_2$ solution was concentrated by rotary evaporation, and then purified by flash column chromatography (60% $CH_2Cl_2$/pentane) to yield 21 as a colorless oil (98 mg, 38%). $^1$H-NMR (500 MHz, $CDCl_3$) δ 6.73 (s, 1H), 4.11 (t, J=6.0 Hz, 2H), 3.54 (t, J=6.0 Hz, 2H), 2.68 (t, J=6.0 Hz, 2H), 2.43 (m, 2H), 1.81 (m, 4H). $^{13}$C NMR (100 MHz, $CDCl_3$) δ 162.27, 146.69, 138.71, 63.31, 44.58, 29.31, 29.20, 27.20, 26.20.

tert-Butyl 4-(cyclobut-1-enecarboxyloyloxy)butylcarbamate, (24)

Cyclobut-1-enecarboxylic acid (1.02 mmol, 100 mg) was dissolved in 1.5 mL dry $CH_2Cl_2$. The solution was cooled to 0° C. and oxalyl dichloride (4.08 mmol, 345 μL) was added. The temperature of the solution was raised to rt, and the mixture was allowed to react for 1 h. The solvent was evaporated to generate a viscous oil. Tert-butyl 4-hydroxybutylcarbamate (1.22 mmol, 232 mg) and pyridine (2.04 mmol, 164 µL) were dissolved in 1.0 mL dry $CH_2Cl_2$, and the solution was stirred at 0° C. for 45 min before being added to a vial containing cyclobut-1-enecarboxylic chloride. The reaction mixture was stirred for 16 h at rt. The $CH_2Cl_2$ solution was concentrated by rotary evaporation, and then purified by flash column chromatography (5% Acetone/$CH_2Cl_2$) to yield 24 as a colorless oil (170 mg, 62%). $^1$H NMR (400 MHz, $CDCl_3$) δ 8.56 (s, 2H), 6.78 (s, 1H), 4.20 (t, J=8 Hz, 2H), 3.67 (m, 2H), 2.69 (m, 2H), 2.42 (m, 2H), 1.44 (m, 2H). $^{13}$C NMR (100 MHz, $CDCl_3$) δ 163.60, 161.92, 153.27, 147.52, 138.36, 83.38, 83.31, 79.54, 79.49, 77.54, 77.22, 76.90, 53.58, 39.75, 39.45, 37.33, 31.03, 29.21, 28.41.

$CBCOO(CH_2)_2N=C(NHBoc)_2$, (25)

Cyclobut-1-enecarboxylic acid (1.02 mmol, 100 mg) was dissolved in 1.5 mL dry $CH_2Cl_2$. The solution was cooled to 0° C. and oxalyl dichloride (4.08 mmol, 345 µL) was added. The temperature of the solution was raised to rt, and the mixture was allowed to react for 1 h. The solvent was evaporated to generate a viscous oil. $HO(CH_2)_2N=C(NHBoc)_2$ (0.51 mmol, 155 mg) and pyridine (2.04 mmol, 164 µL) were dissolved in 1.0 mL dry $CH_2Cl_2$, and the solution was stirred at 0° C. for 45 min before being added to a vial containing cyclobut-1-enecarboxylic chloride. The reaction mixture was stirred for 16 h at rt. The $CH_2Cl_2$ solution was concentrated by rotary evaporation, and then purified by flash column chromatography (10% Acetone/$CH_2Cl_2$) to yield 25 as a colorless oil (90 mg, 46%). $^1$H NMR (600 MHz, $CDCl_3$) δ 6.76 (s, 1H), 4.13 (t, J=6 Hz, 2H), 3.15 (m, 2H), 2.71 (m, 2H), 2.46 (m, 2H), 1.68 (m, 2H), 1.55 (m, 2H), 1.43 (s, 9H). $^{13}$C NMR (100 MHz, $CDCl_3$) δ 162.31, 156.19, 146.68, 138.93, 64.16, 53.72, 40.46, 31.10, 29.32, 28.60, 27.27, 26.22.

N-propylcyclohex-3-enecarboxamide, (26)

Cyclohex-3-enecarboxylic acid (0.71 mmol, 90 mg), $NH_2CH_2CH_2CH_3$ (0.86 mmol, 70 µL) and EDC.HCl (0.86 mmol, 164 mg) were dissolved in $CH_2Cl_2$ (3 mL). DIEA (1.43 mmol, 252 µL) was added at 0° C., and the reaction was stirred for 16 h at rt. The usual workup and chromatography (Acetone/$CH_2Cl_2$/10:90) yielded N-propylcyclohex-3-enecarboxamide 26 as a white powder (65 mg, 55%). $^1$H NMR (400 MHz, $CDCl_3$) δ 5.64 (m, 3H), 3.17 (dd, J=8 Hz, J=8 Hz, 2H), 2.30-1.93 (m, 5H), 1.87-1.81 (m, 1H), 1.72-1.59 (m, 1H), 1.43 (m, 2H), 0.87 (t, J=8 Hz, 3H). $^{13}$C NMR (100 MHz, $CDCl_3$) δ 175.93, 126.94, 125.61, 41.52, 41.22, 28.35, 25.97, 24.80, 23.07, 11.49.

N-octylcyclohex-3-enecarboxamide, (27)

Cyclohex-3-enecarboxylic acid (1.11 mmol, 140 mg), $NH_2$-octyl (1.33 mmol, 220 µL) and EDC.HCl (1.33 mmol, 255 mg) were dissolved in $CH_2Cl_2$ (3 mL). DIEA (2.22 mmol, 393 µL) was added at 0° C., and the reaction was stirred for 16 h at rt. The usual workup and chromatography (Acetone/$CH_2Cl_2$/10:90) yielded N-octylcyclohex-3-enecarboxamide 27 as a white powder (215 mg, 82%). $^1$H NMR (400 MHz, $CDCl_3$) δ 5.77 (s, 1H), 5.63 (s, 2H), 3.18 (dd, J=8 Hz, J=8 Hz, 2H), 2.33-2.00 (m, 5H), 1.86-1.82 (s, 1H), 1.70-1.60 (m, 1H), 1.43 (m, 2H), 1.22 (m, 10H), 0.82 (t, J=8 Hz, 3H). $^{13}$C NMR (100 MHz, $CDCl_3$) δ 175.89, 126.88, 125.59, 41.46, 39.56, 31.91, 29.81, 29.39, 29.33, 28.32, 27.05, 25.93, 24.79, 22.75, 14.19.

PDI (Polydispersity Index) Determination

Polymers are dissolved in THF (0.5 mg/mL). An aliquot (100 µL) of the polymer solution was analyzed by gel permeation chromatography using a Phenogel column (300×7.80 mm, 5 µm, linear mixed bed, 0-40 k MW range). Elution was performed at 0.7 mL/min with THF and detection at 220 nm at 30° C. Narrowly dispersed polystyrene standards from Aldrich were used as molecular weight calibrants. The number average and weighted average molecular weights were calculated from the chromatogram.

General Procedure for AROMP

The NMR tube was evacuated under high vacuum for 15 min, and then was purged with Ar gas for another 15 min. Under an Ar atmosphere, a solution of monomer A (1-cyclobutene-carboxylate ester) in $CD_2Cl_2$ (300 µl) was added to the NMR tube. Then a solution of precatalyst ($H_2$IMes)(3-Br-Py)$_2$Cl$_2$Ru=CHPh 1 in $CD_2Cl_2$ (300 µl) was added to the NMR tube. After complete mixing of the solution, the NMR tube was spun for 4-30 min at 25° C. in the NMR spectrometer (400, 500 or 600 MHz) until the precatalyst had been reacted. Then monomer B (cyclohexene derivatives) in $CD_2Cl_2$ (300 µl) was added to the NMR tube. After all of monomer A was converted, the reaction was quenched with ethylvinyl ether (50 µl) and was stirred for 1 h.

(2-5)$_{10}$: (6b)

Cyclobutene 2 (0.06 mmol), cyclohexene 5 (0.12 mmol) and 1 (0.006 mmol) were mixed in $CD_2Cl_2$ (600 µl) in an NMR tube. The reaction was maintained for 3 h to reach 98% completion. Degree of polymerization (DP)=98. $M_n^{calc}$=2044. $M_n^{GPC}$=376. $M_w^{GPC}$=962. PDI=2.6.

(2-5)$_{20}$: (6c)

Cyclobutene 2 (0.12 mmol), cyclohexene 5 (0.24 mmol) and 1 (0.006 mmol) were mixed in $CD_2Cl_2$ (600 µl in an NMR tube. The reaction was maintained for 3 h to reach 98% completion. DP=98. $M_n^{calc}$=3984. $M_n^{GPC}$=668. $M_w^{GPC}$=1816. PDI=2.7.

(2-5)$_{50}$: (6d)

Cyclobutene 2 (0.30 mmol), cyclohexene 5 (0.60 mmol) and 1 (0.006 mmol) were mixed in $CD_2Cl_2$ (600 µl) in an NMR tube. The reaction was maintained for 3 h to reach 98% completion. DP=98. $M_n^{calc}$=9804. $M_n^{GPC}$=652. $M_w^{GPC}$=2634. PDI=4.0.

Figure 10:
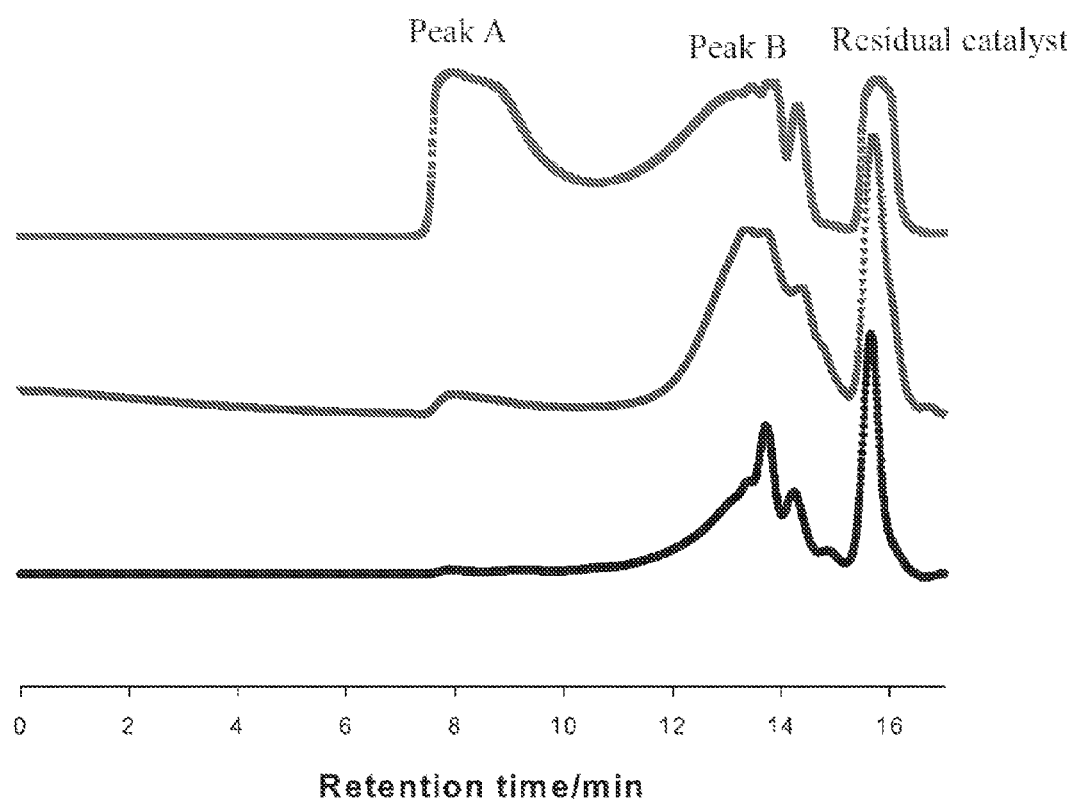
FIG. 10 depicts GPC traces of $(2\text{-}5)_{100}$ and $(2\text{-}5)_{200}$.

(2-5)$_{100}$: (6e):

Cyclobutene 2 (0.60 mmol), cyclohexene 5 (1.20 mmol) and 1 (0.006 mmol) were mixed in $CD_2Cl_2$ (600 µl) in an NMR tube. The reaction was maintained for 3 h to reach 97% completion. The crude solution was evaporated to remove solvent, and the residue was purified by flash column chromatography (acetone:$CH_2Cl_2$/3:97) to provide polymer 6e (72 mg, 62%). DP=97. According to GPC chromatographic analysis, the copolymer had a bimodal molecular weight distribution (FIG. 10). $M_n^{calc}$=19504. $M_n^{GPC}$=1869. $M_w^{GPC}$=10872. PDI=5.8.

(2-5)$_{200}$: (6f)

Figure 11:
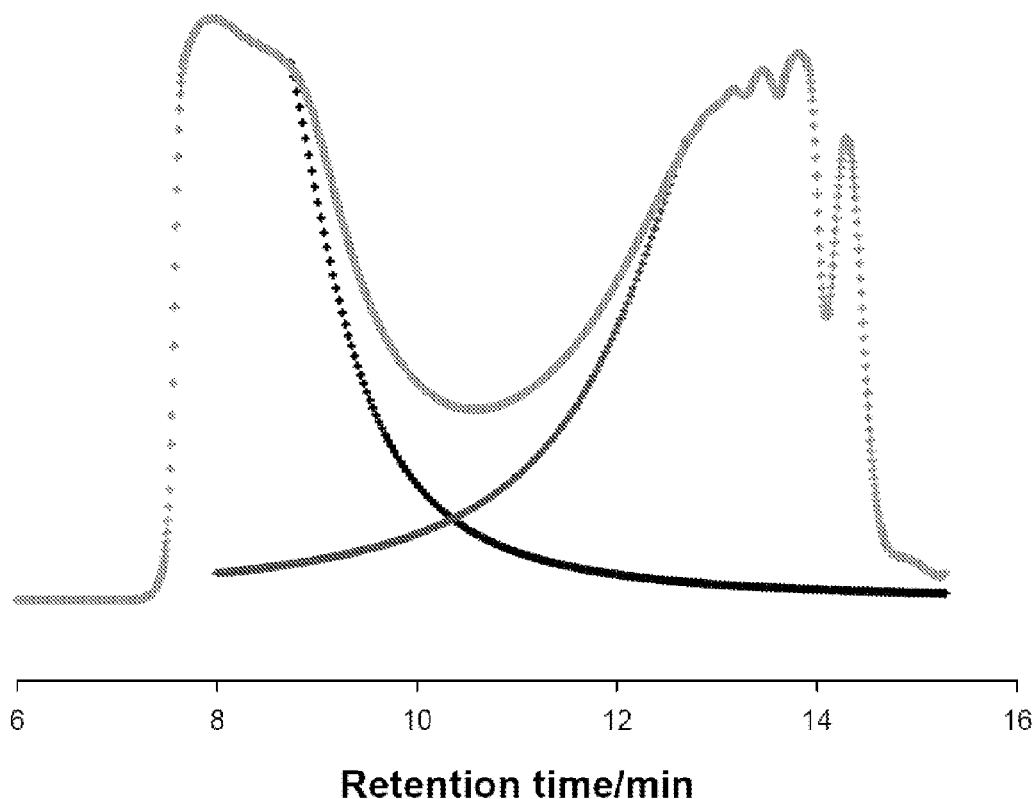
FIG. 11 shows bimodal peak fitting of GPC trace of $(2\text{-}5)_{200}$.
Figure 12:
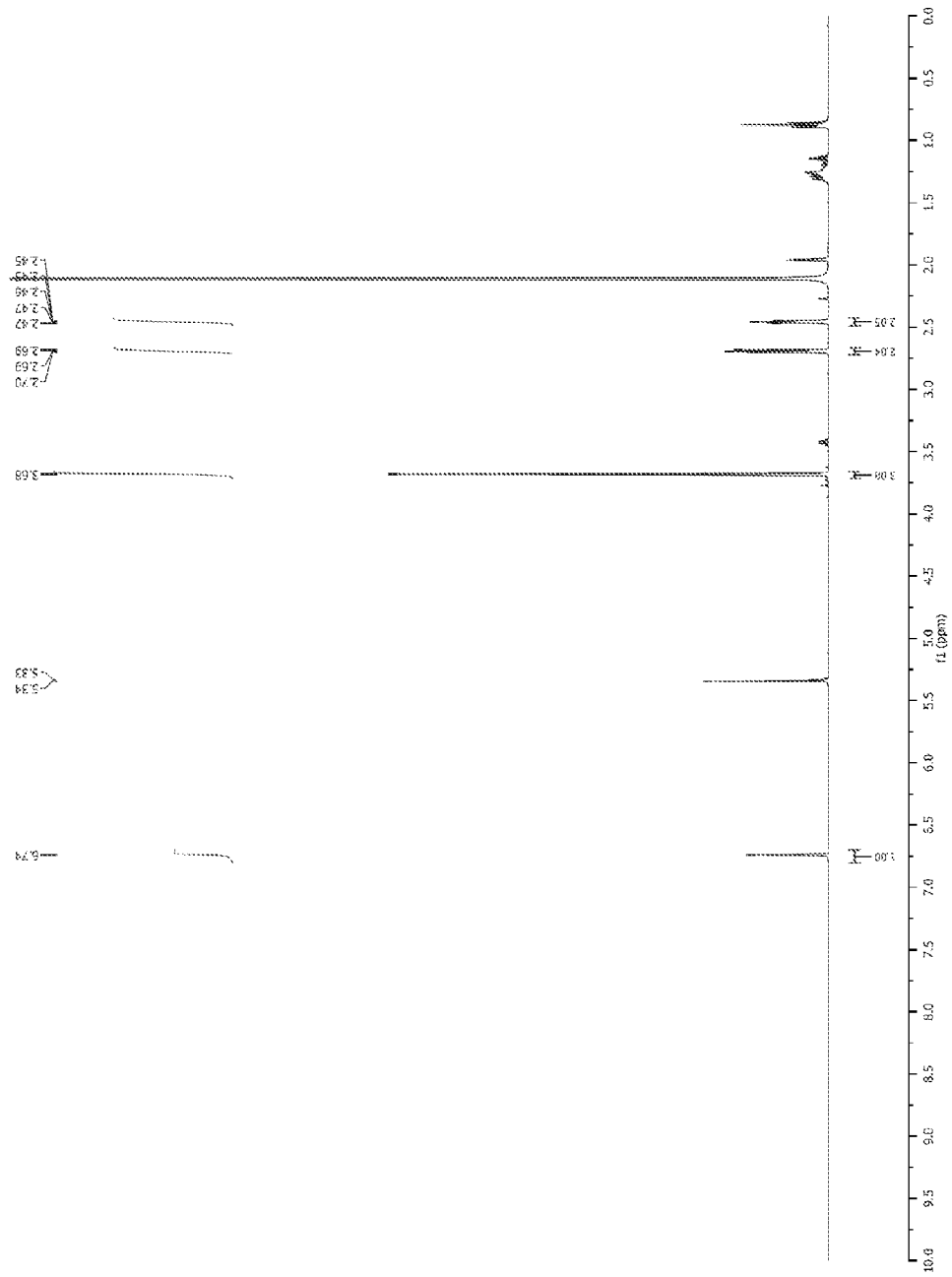
FIG. 12 depicts the $^1$H-NMR spectrum of 2.
Figure 13:
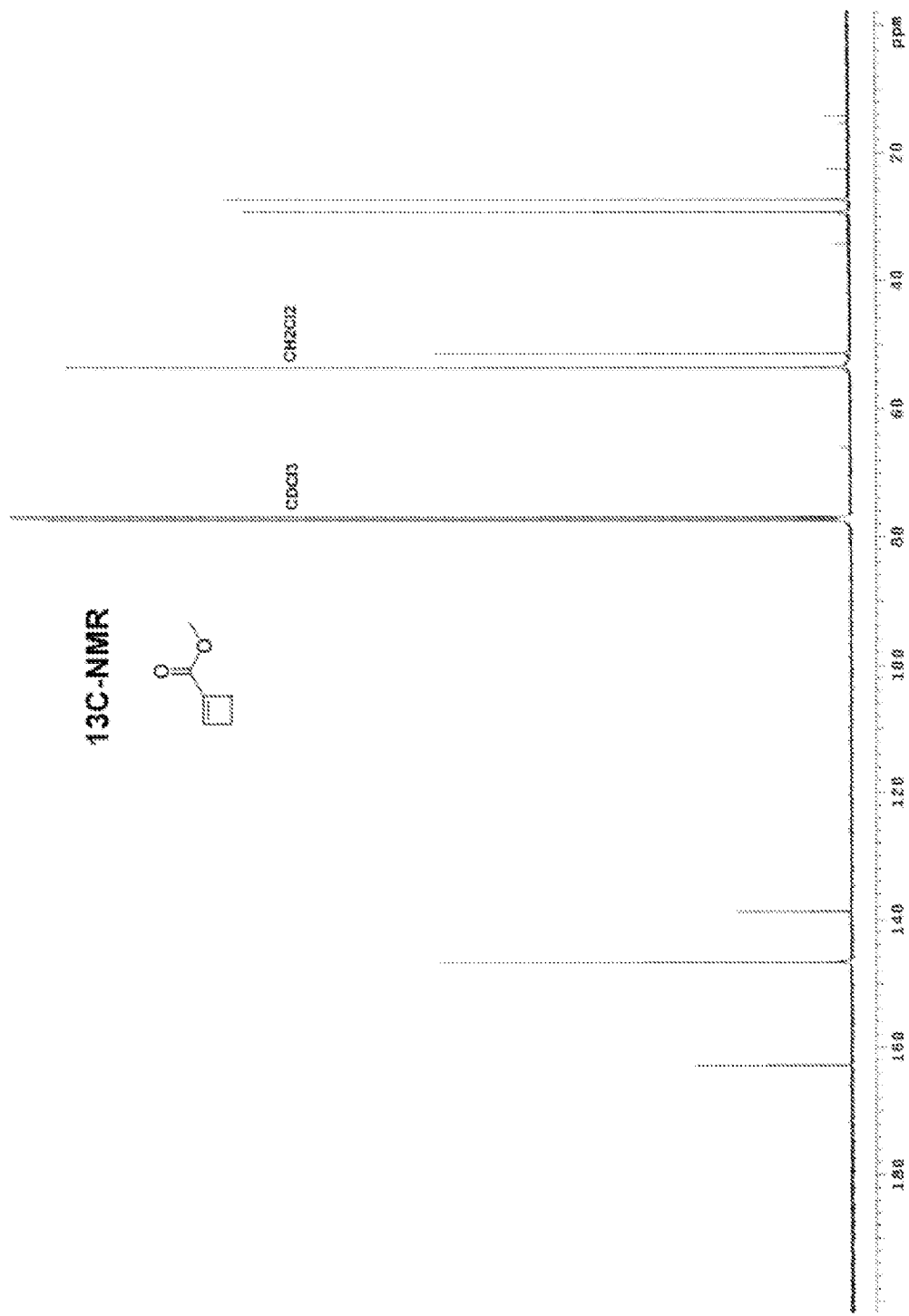
FIG. 13 depicts the $^{13}$C-NMR spectrum of 2
Figure 14:
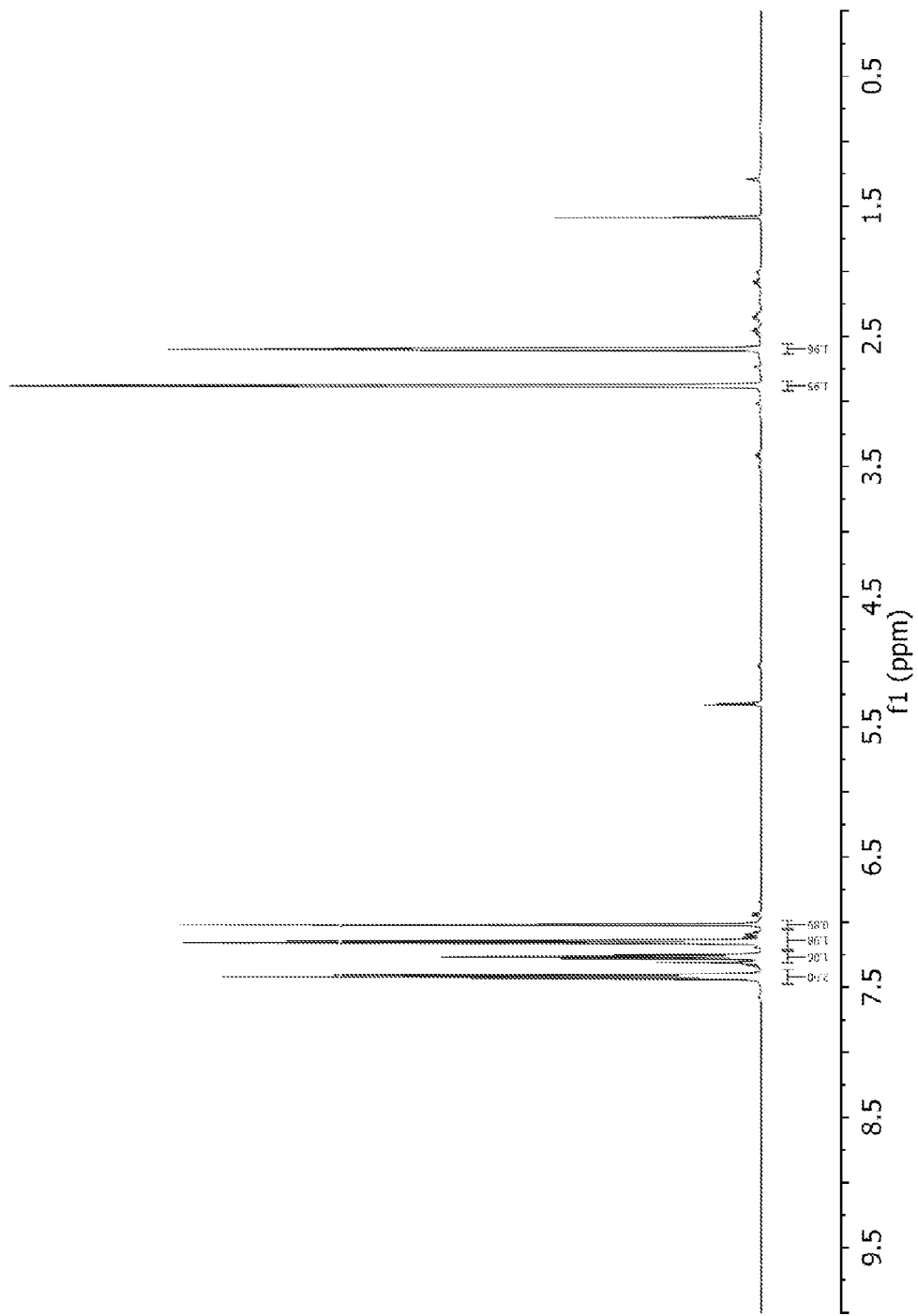
FIG. 14 depicts the $^1$H-NMR spectrum of 11.
Figure 15:
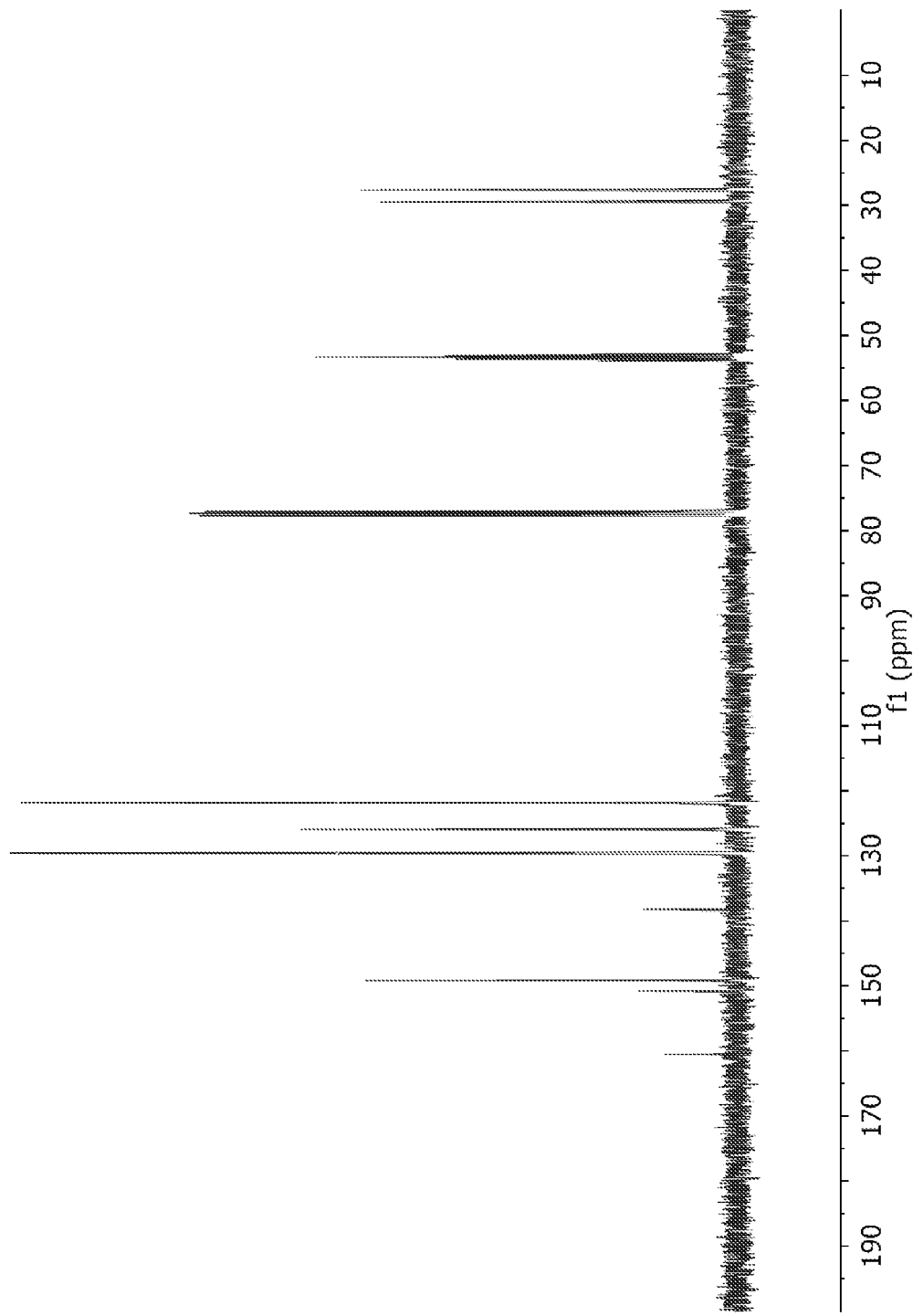
FIG. 15 depicts the $^{13}$C-NMR spectrum of 11.
Figure 16:
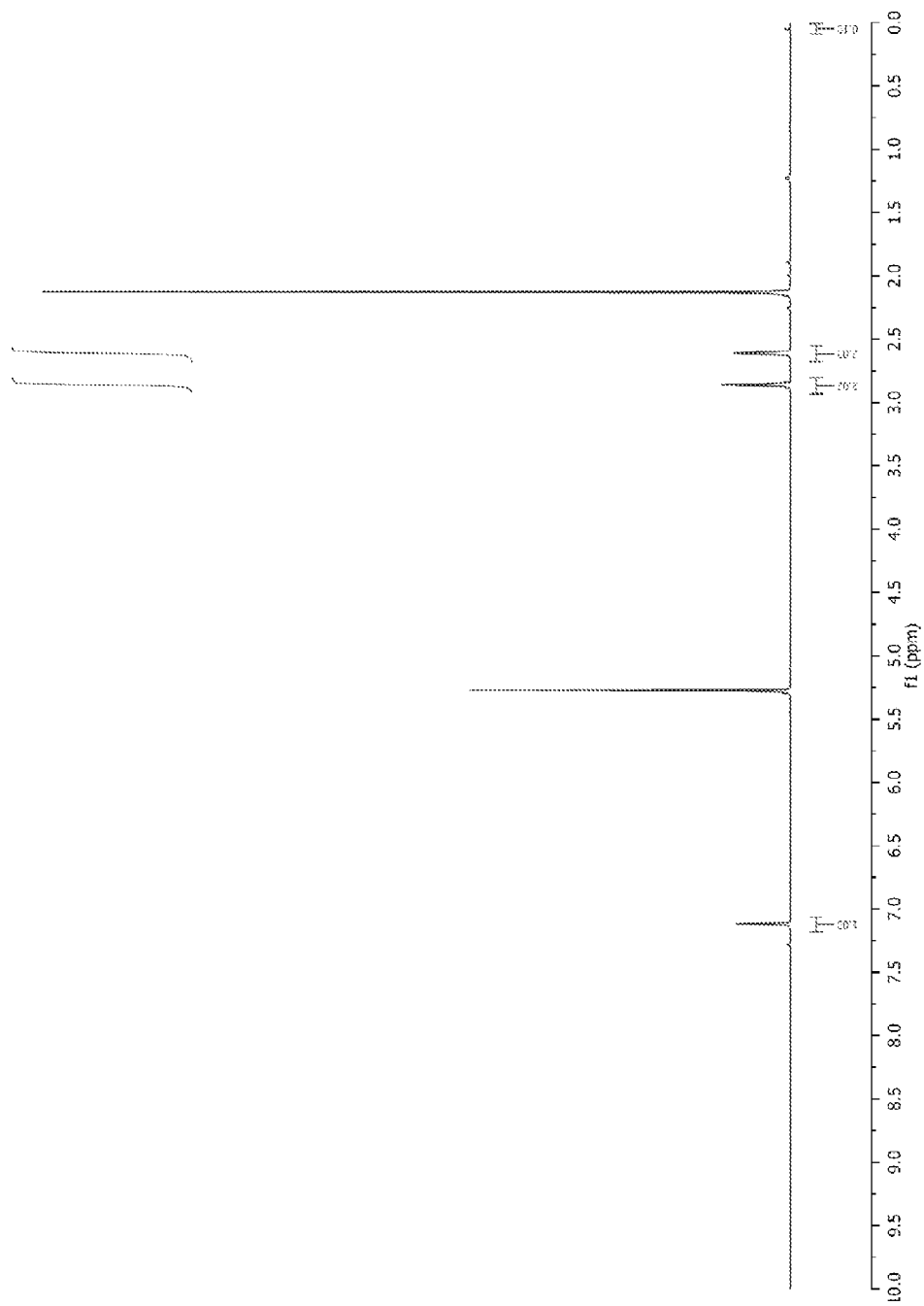
FIG. 16 depicts the $^1$H-NMR spectrum of 13.
Figure 17:
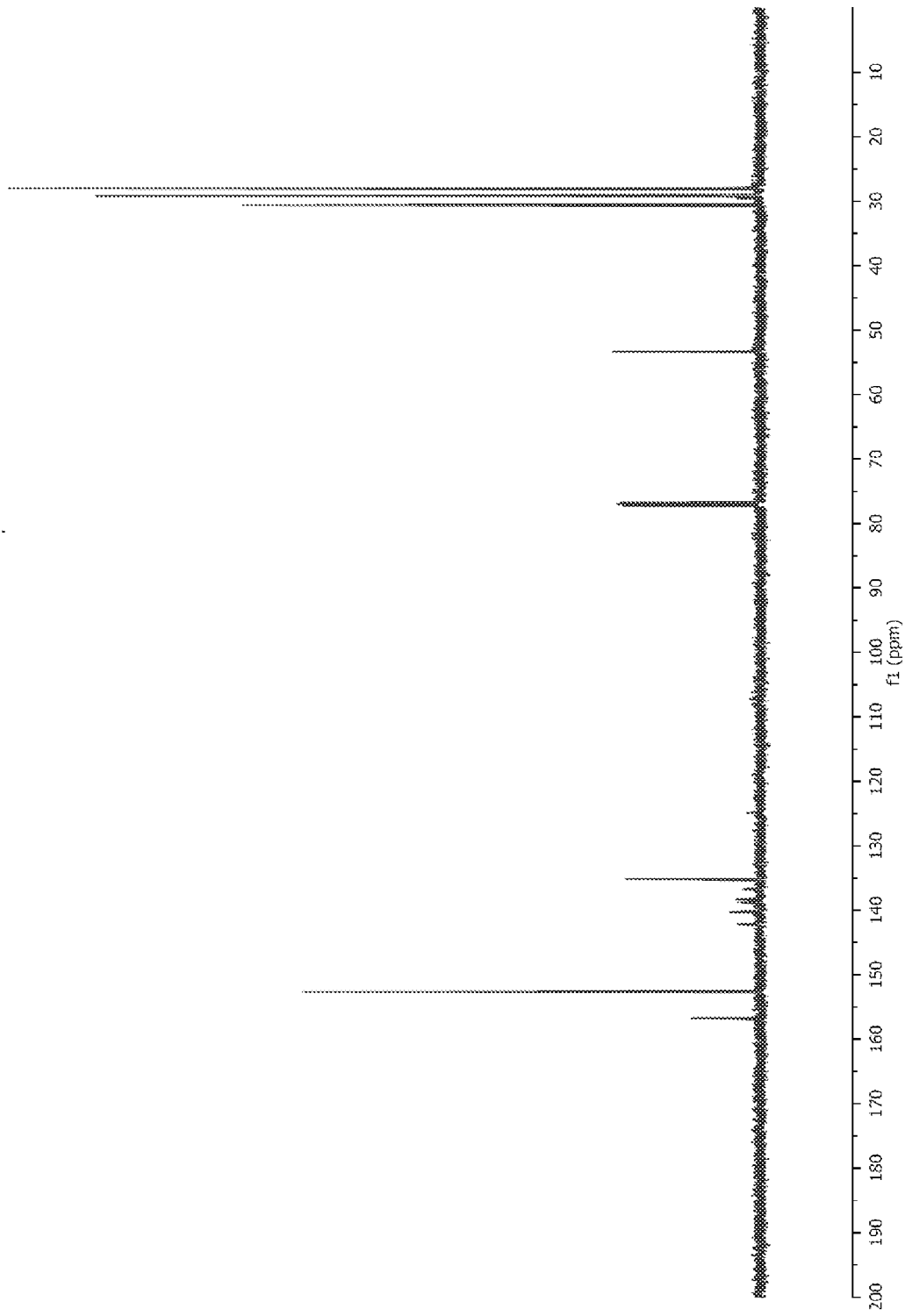
FIG. 17 depicts the $^{13}$C-NMR spectrum of 13.
Figure 18:
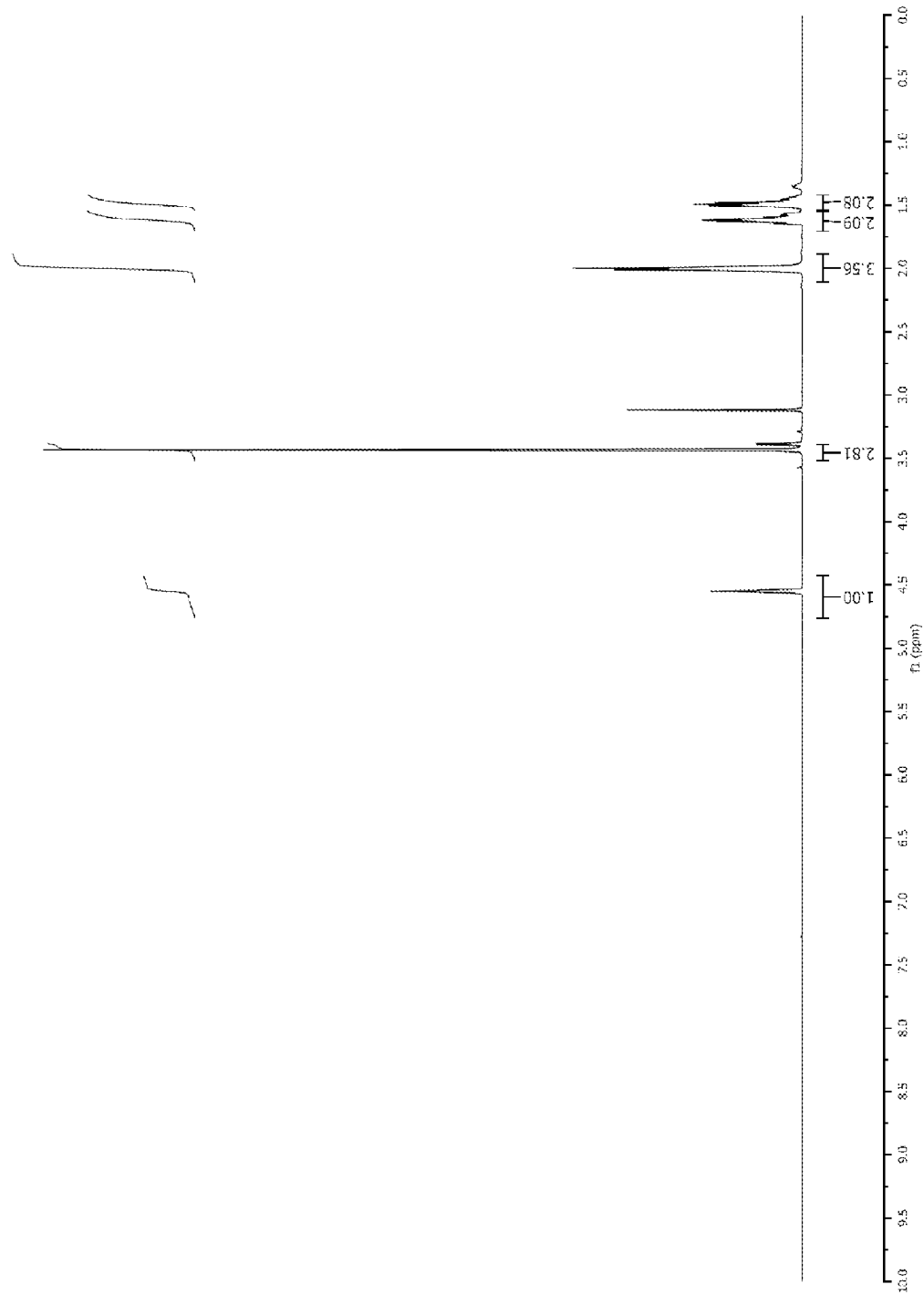
FIG. 18 depicts the $^1$H-NMR spectrum of 10.
Figure 19:
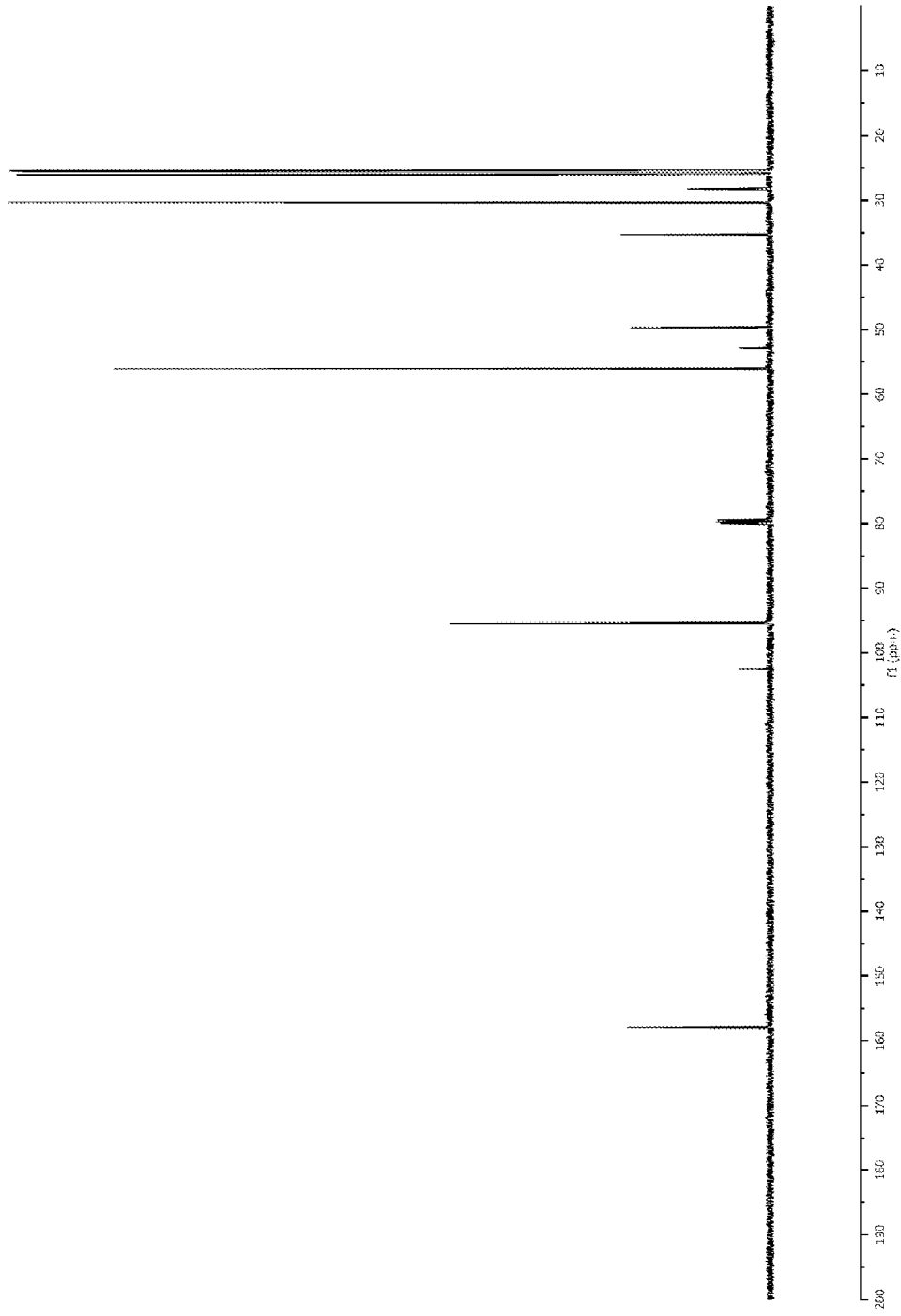
FIG. 19 depicts the $^{13}$C-NMR spectrum of 10.
Figure 20:
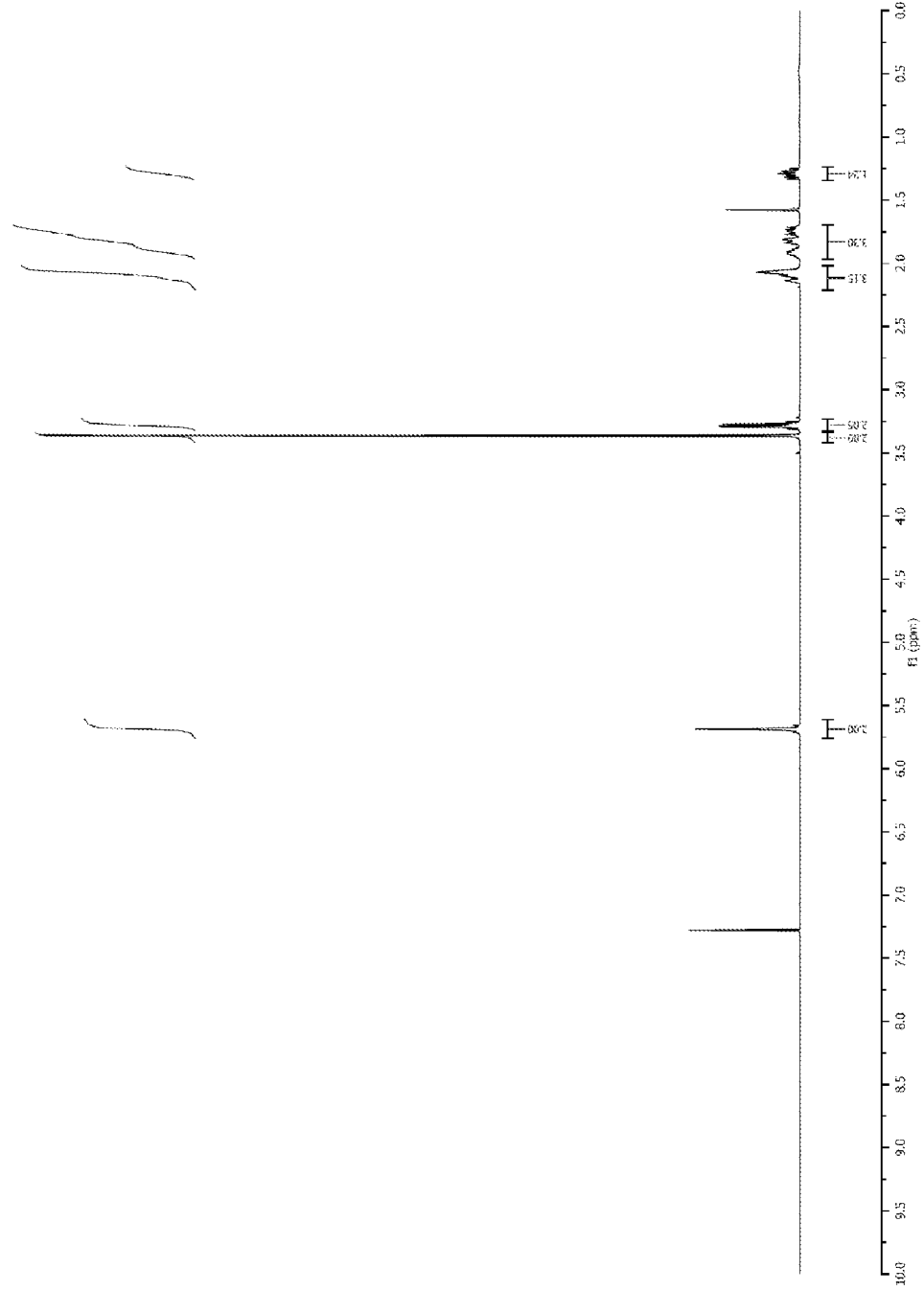
FIG. 20 depicts the $^1$H-NMR spectrum of 16.
Figure 21:
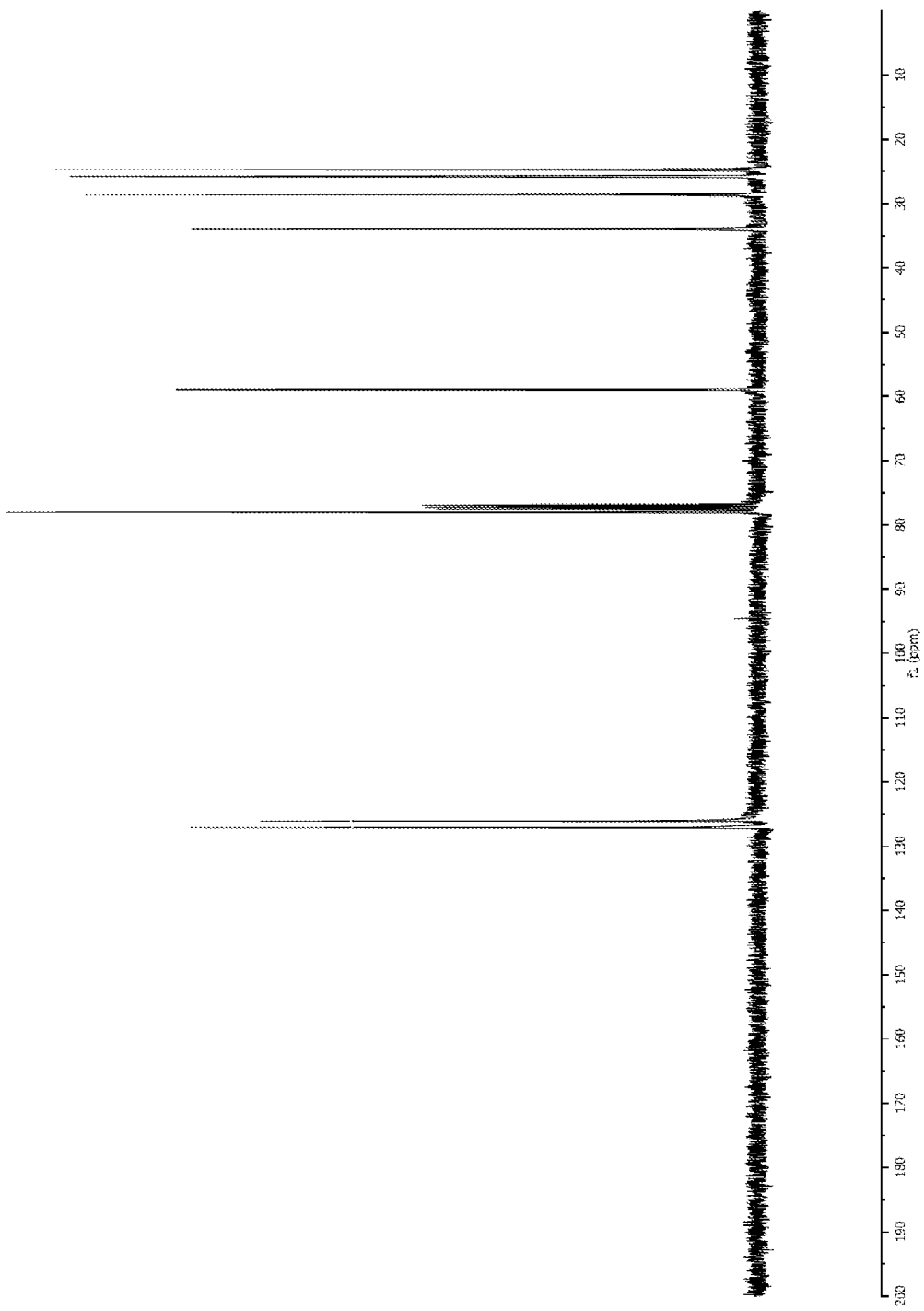
FIG. 21 depicts the $^{13}$C-NMR spectrum of 16.
Figure 22:
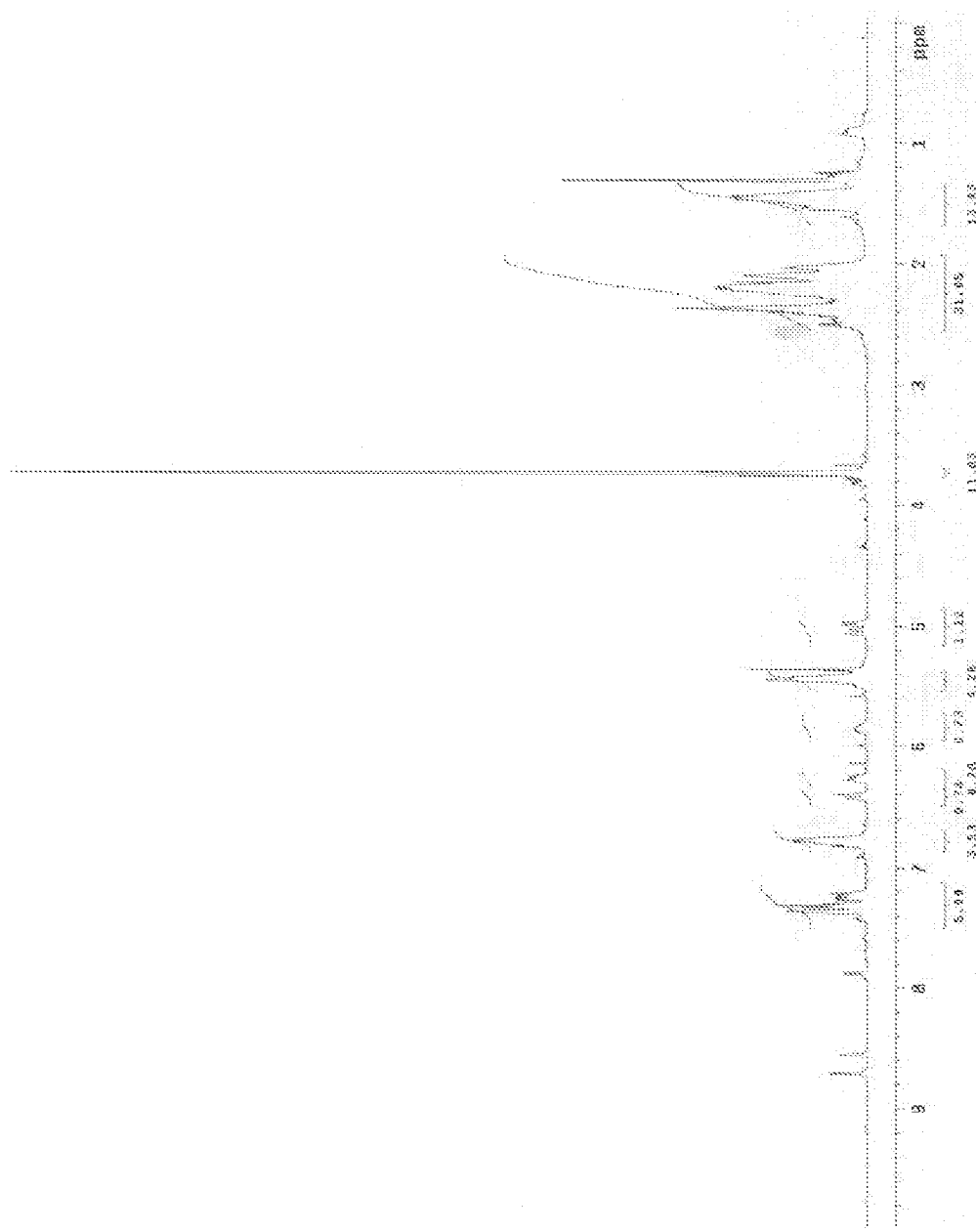
FIG. 22 depicts the $^1$H-NMR spectrum of $(2\text{-}5)_3$.
Figure 23:
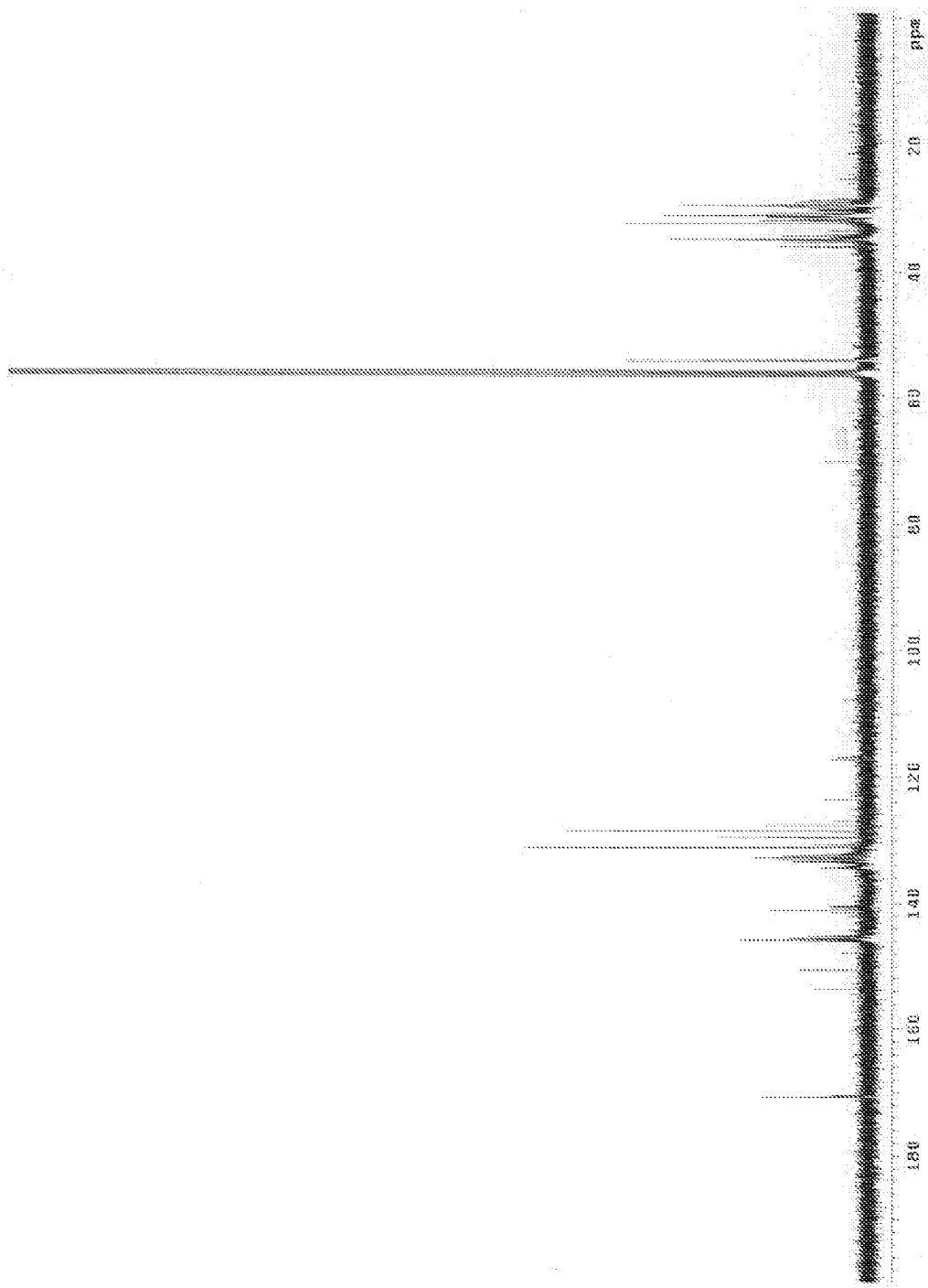
FIG. 23 depicts the $^{13}$C-NMR spectrum of $(2\text{-}5)_3$.
Figure 24:
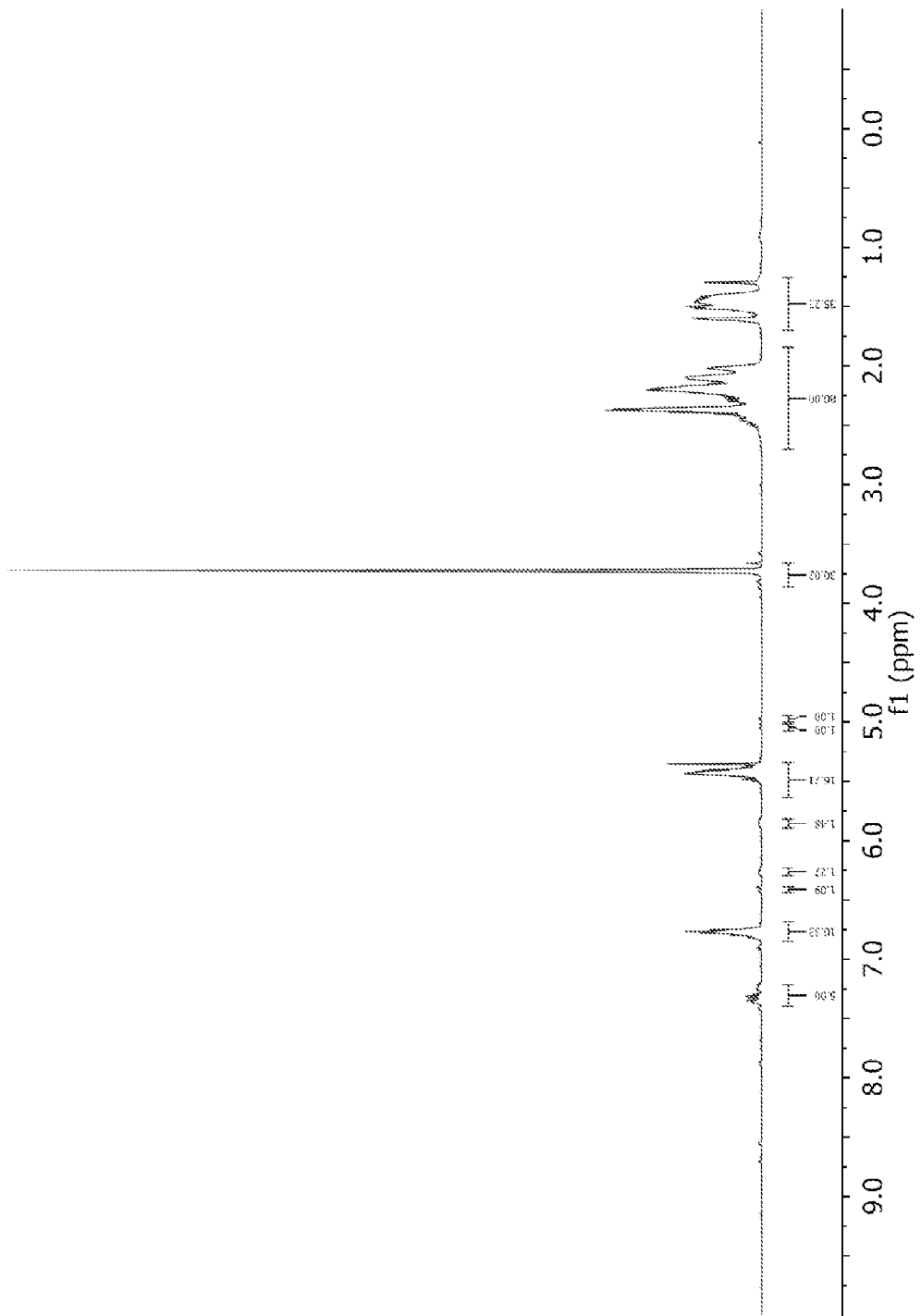
FIG. 24 depicts the $^1$H-NMR spectrum of $(2\text{-}5)_{10}$.
Figure 25:
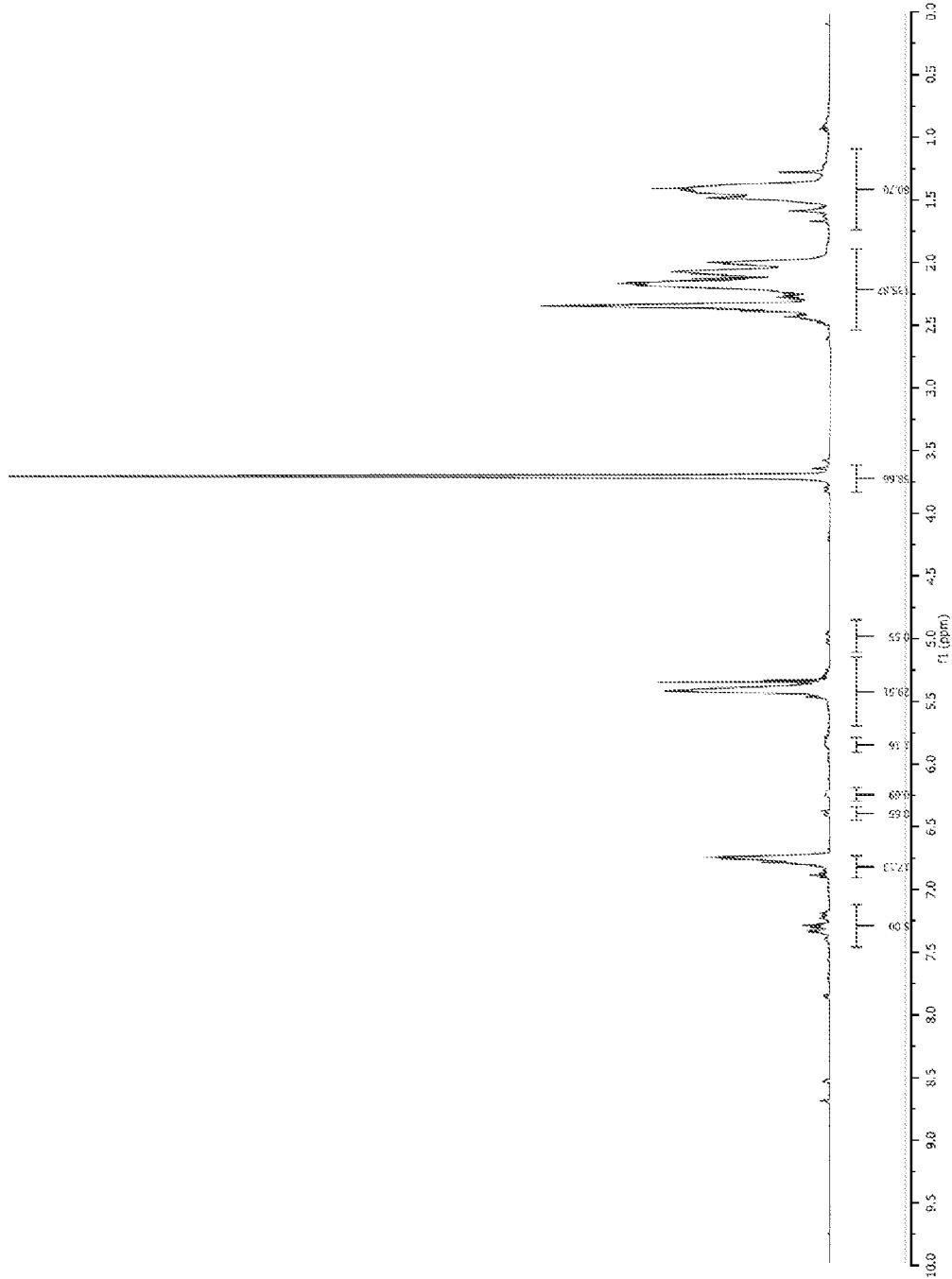
FIG. 25 depicts the $^1$H-NMR spectrum of $(2\text{-}5)_{20}$.
Figure 26:
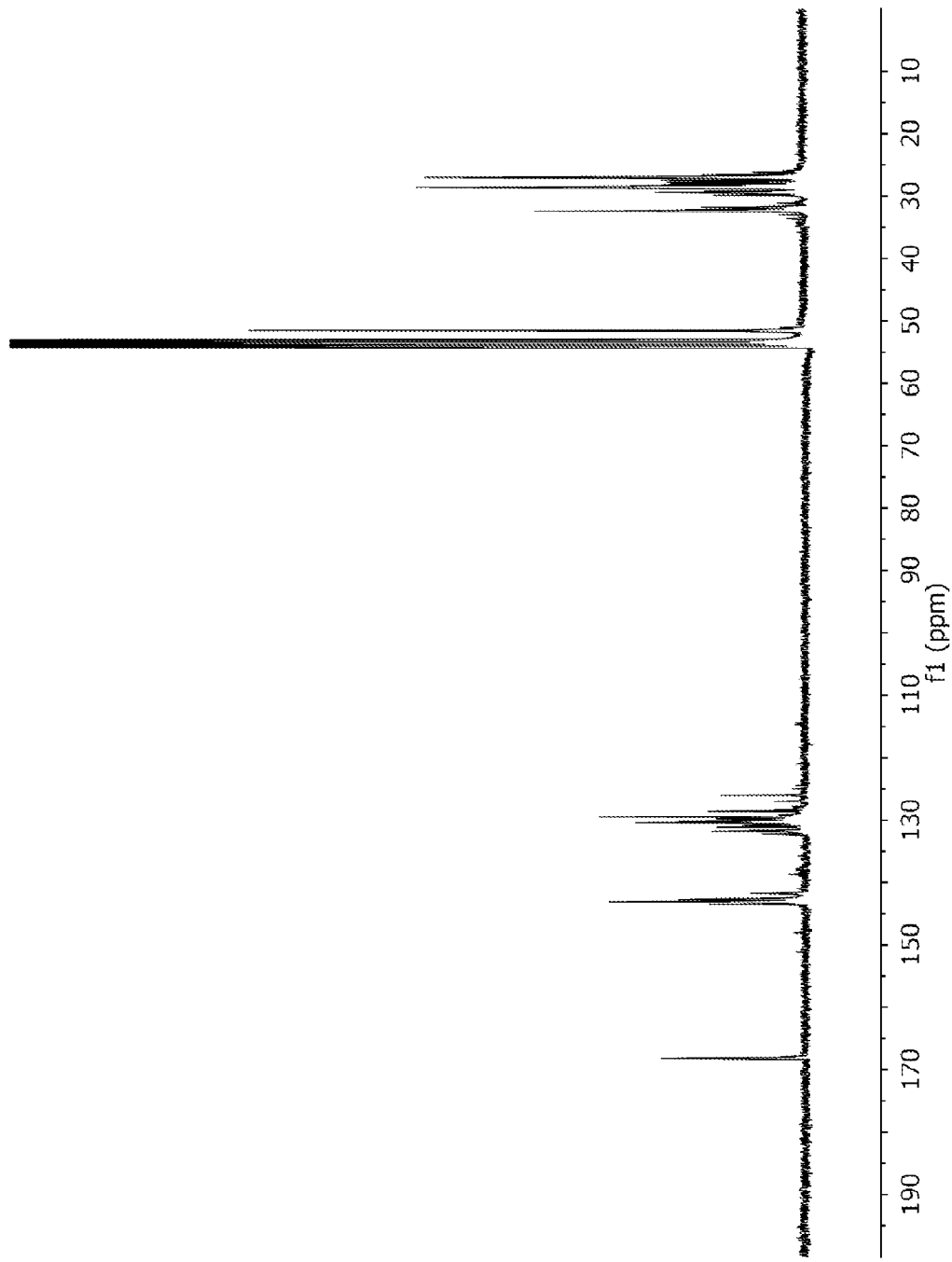
FIG. 26 depicts the $^{13}$C-NMR spectrum of $(2\text{-}5)_{20}$.
Figure 27:
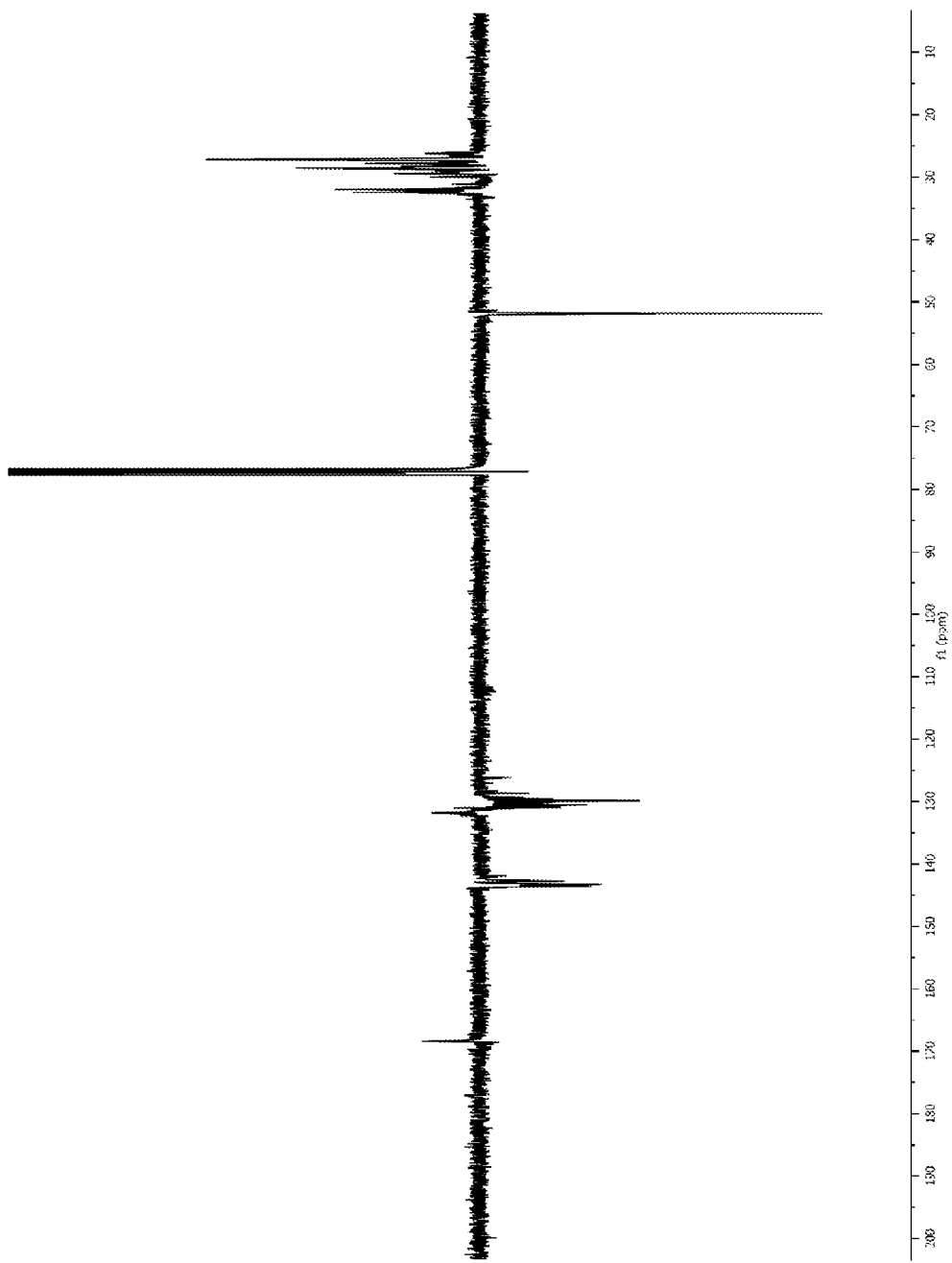
FIG. 27 depicts the $^{13}$C-APT-NMR spectrum of $(2\text{-}5)_{20}$.
Figure 28:
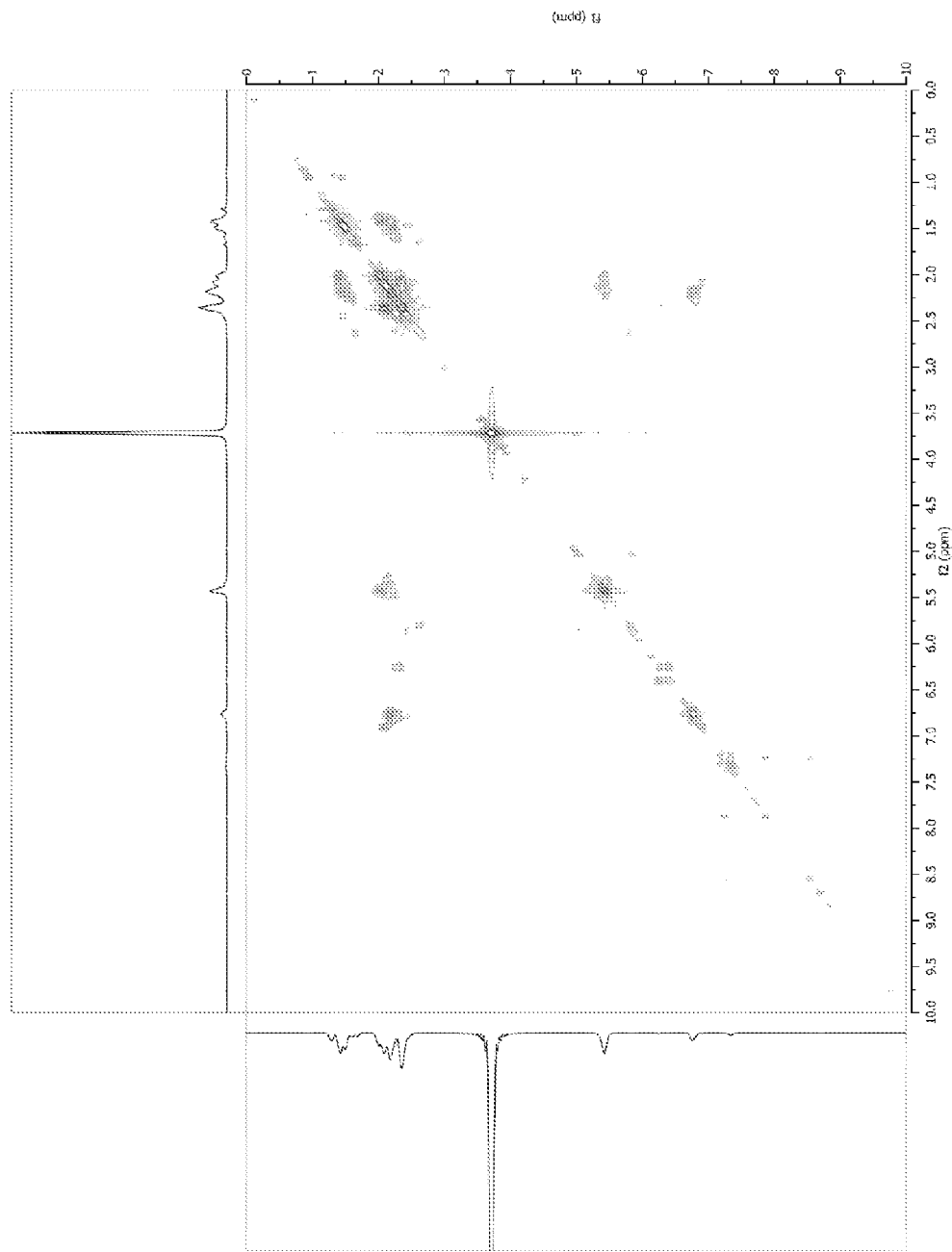
FIG. 28 depicts the $^1$H-gCOSY-NMR spectrum of $(2\text{-}5)_{20}$.
Figure 29:
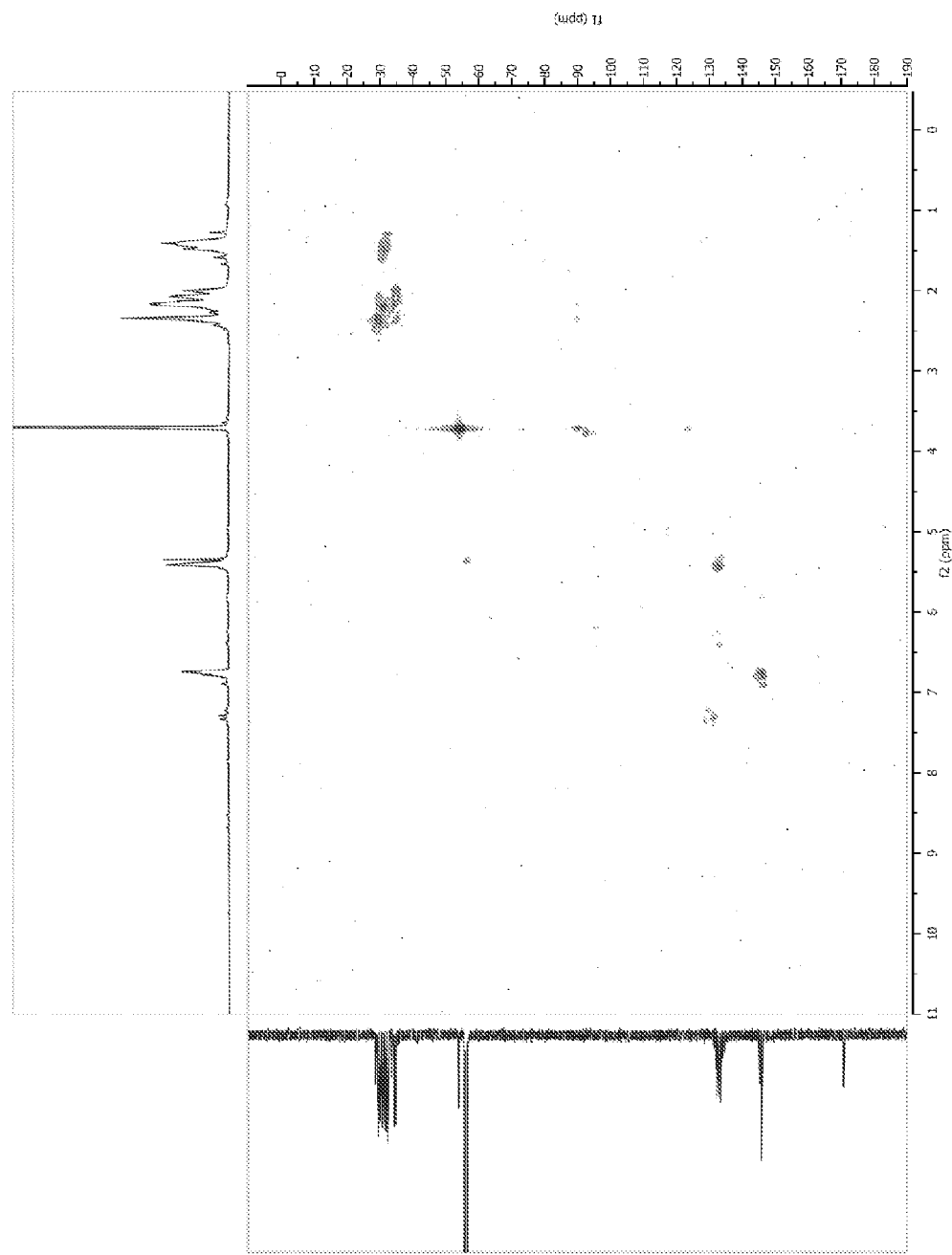
FIG. 29 depicts the $^1$H—$^{13}$C-HMQC-NMR spectrum of $(2\text{-}5)_{20}$.
Figure 30:
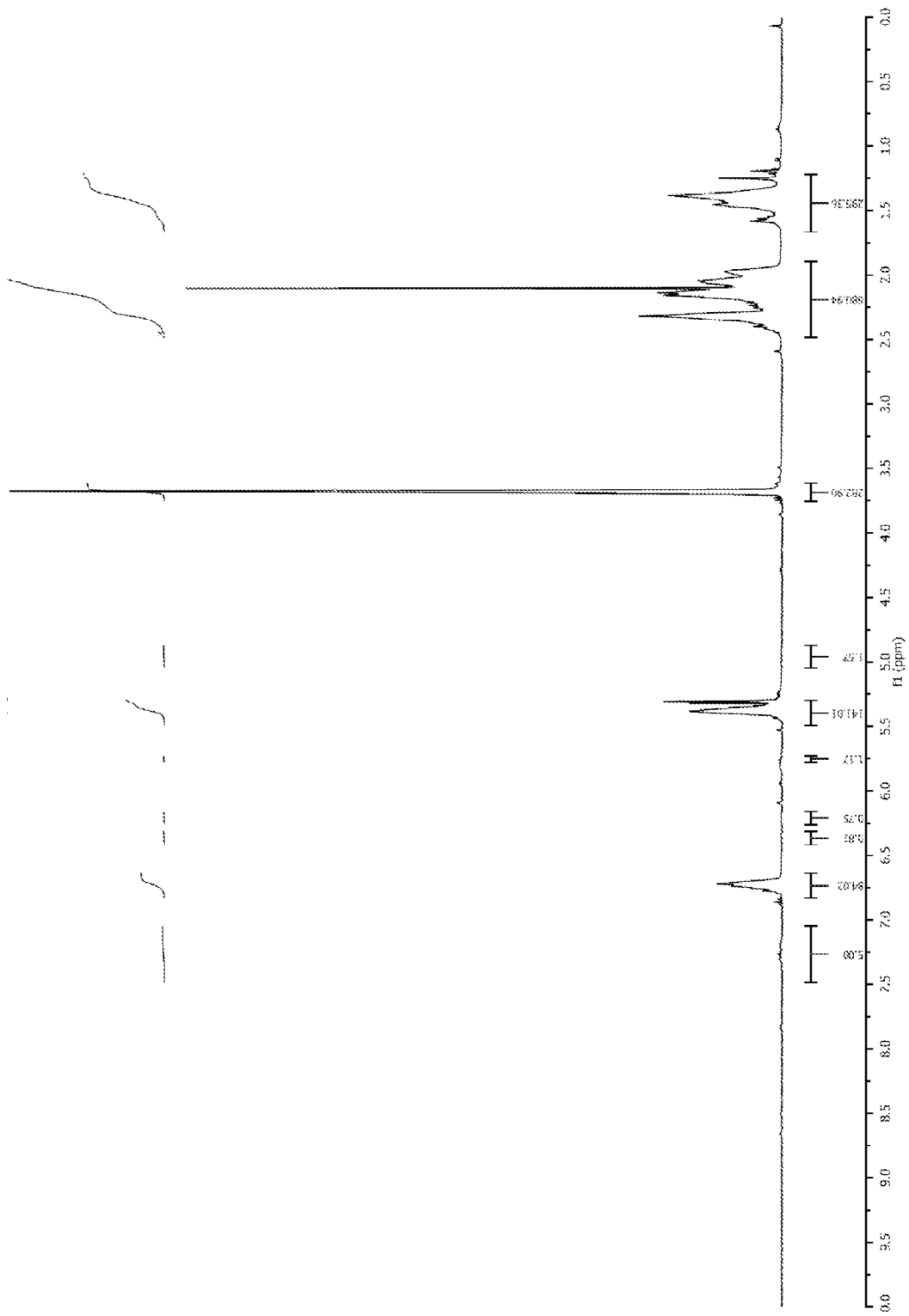
FIG. 30 depicts the $^1$H-NMR spectrum of $(2\text{-}5)_{50}$.
Figure 31:
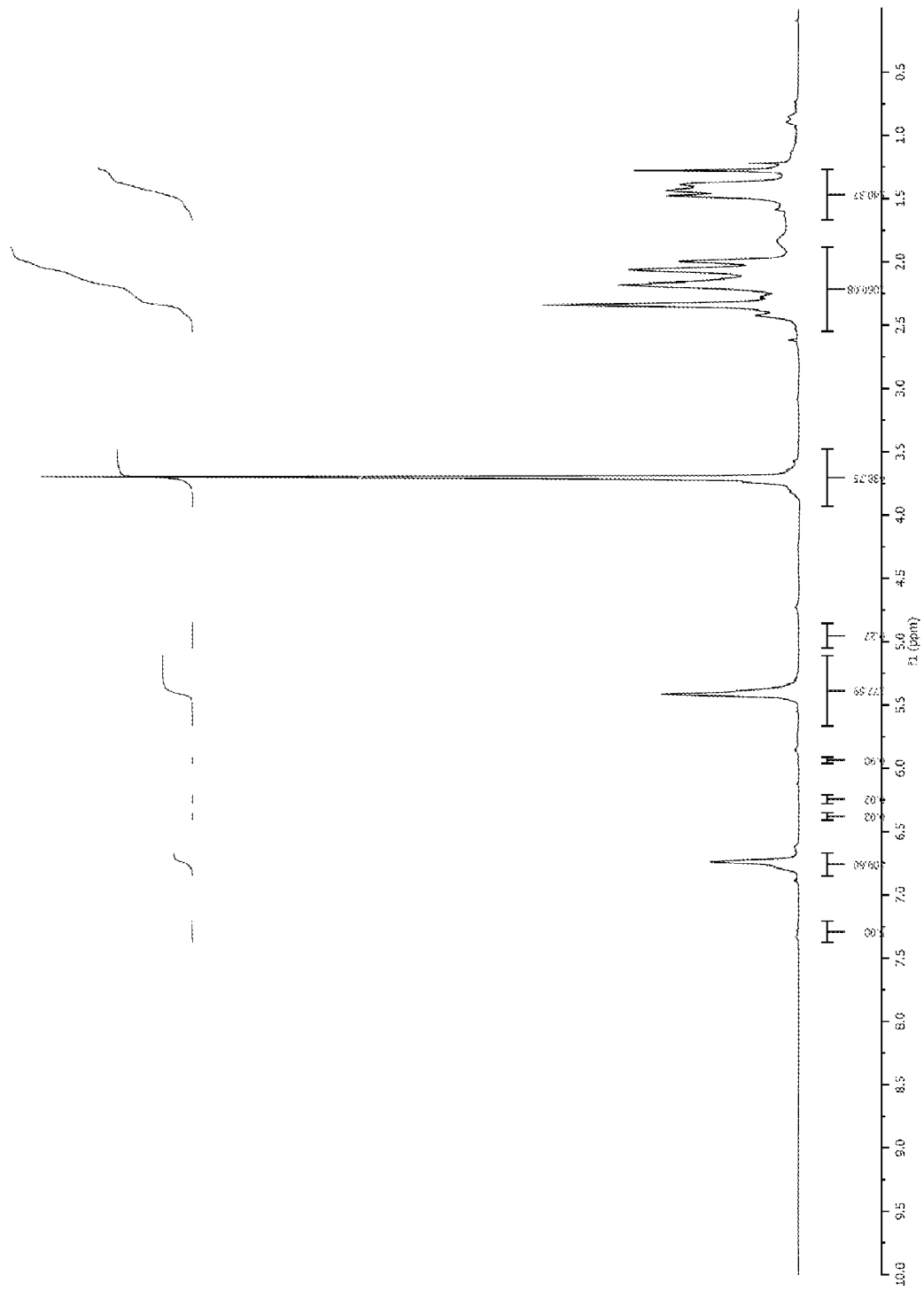
FIG. 31 depicts the $^1$H-NMR spectrum of $(2\text{-}5)_{100}$.
Figure 32:
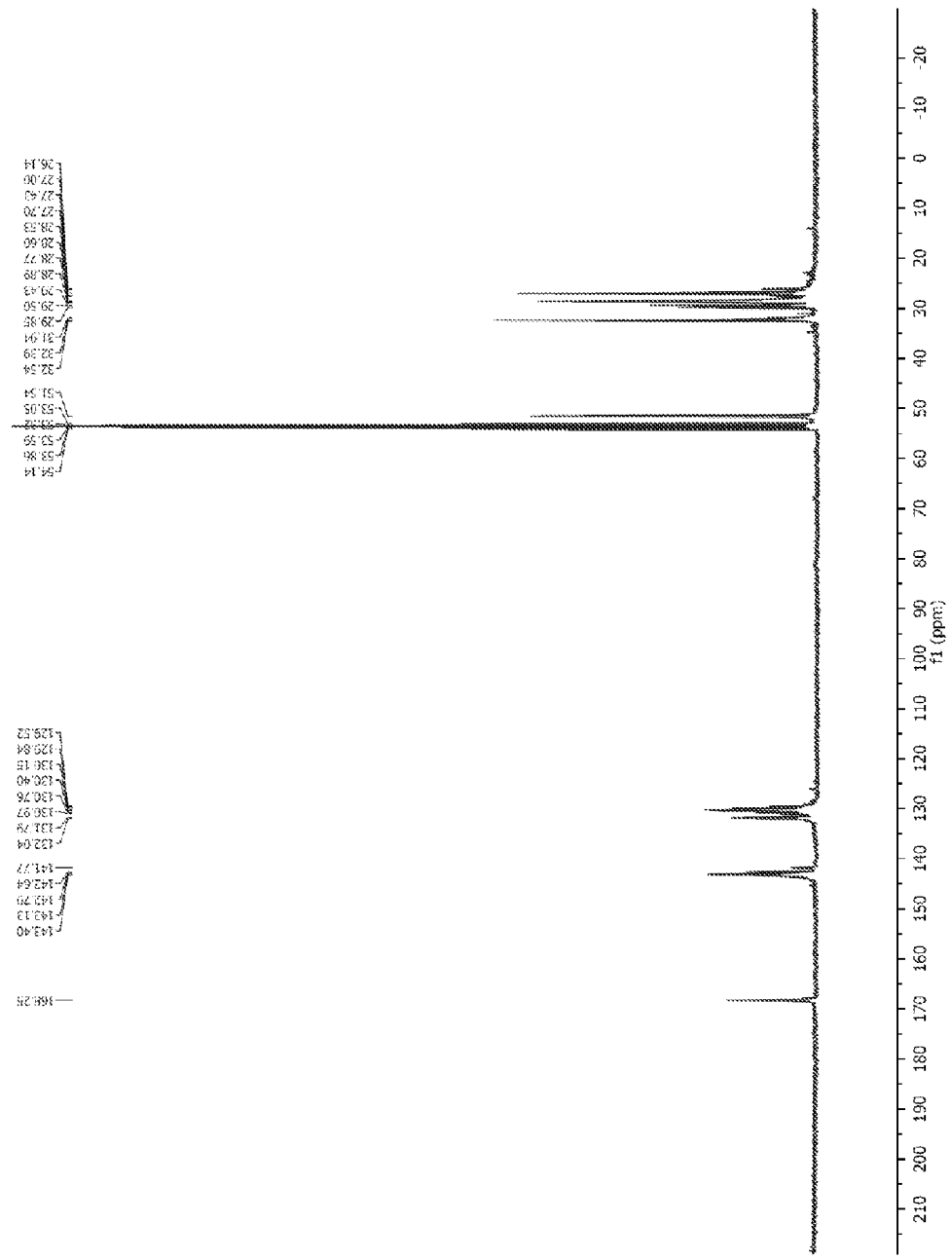
FIG. 32 depicts the $^{13}$C-NMR spectrum of $(2\text{-}5)_{100}$.
Figure 33:
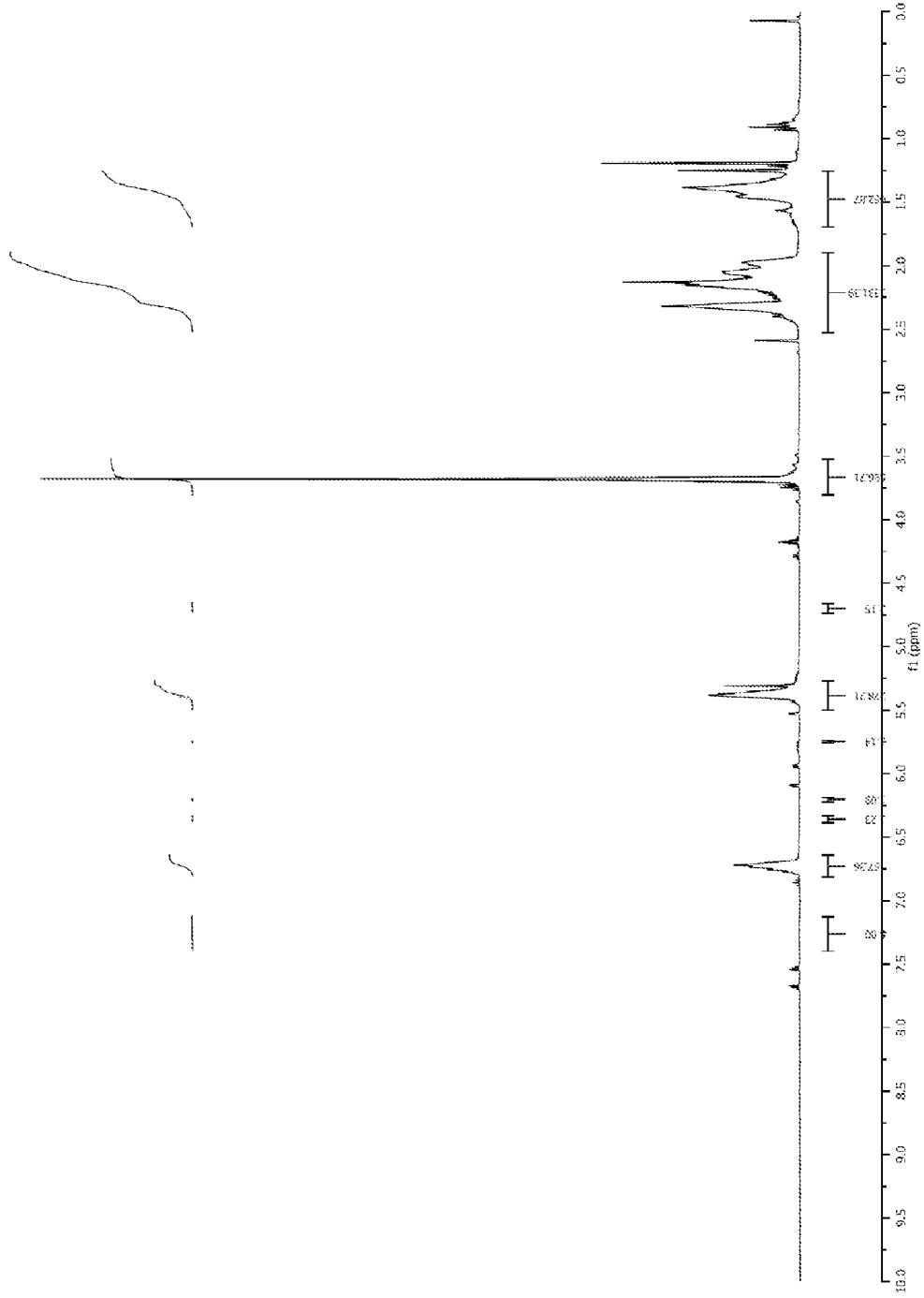
FIG. 33 depicts the $^1$H-NMR spectrum of $(2\text{-}5)_{200}$.
Figure 34:
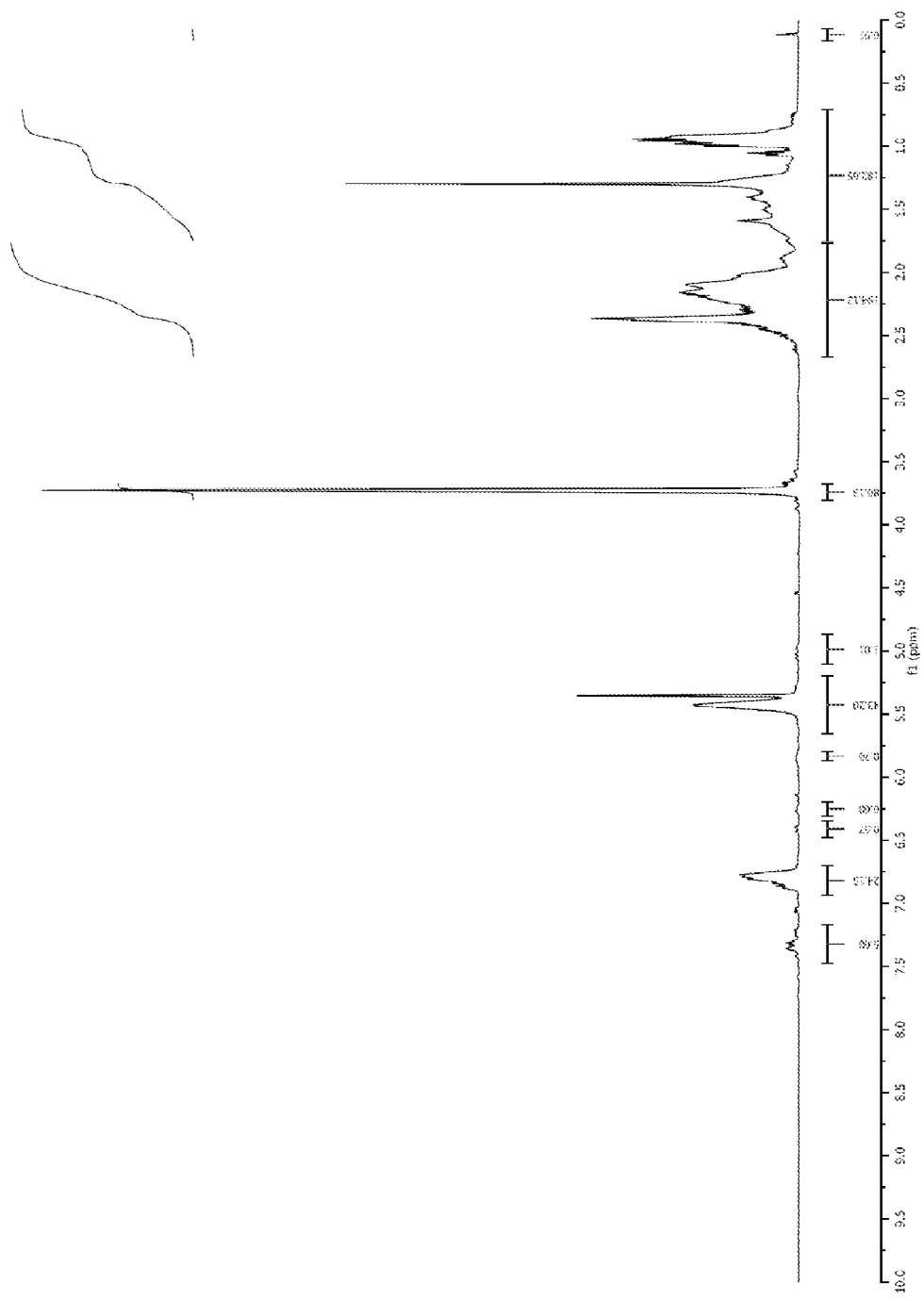
FIG. 34 depicts the $^1$H-NMR spectrum of $(2\text{-}15)_{20}$.
Figure 35:
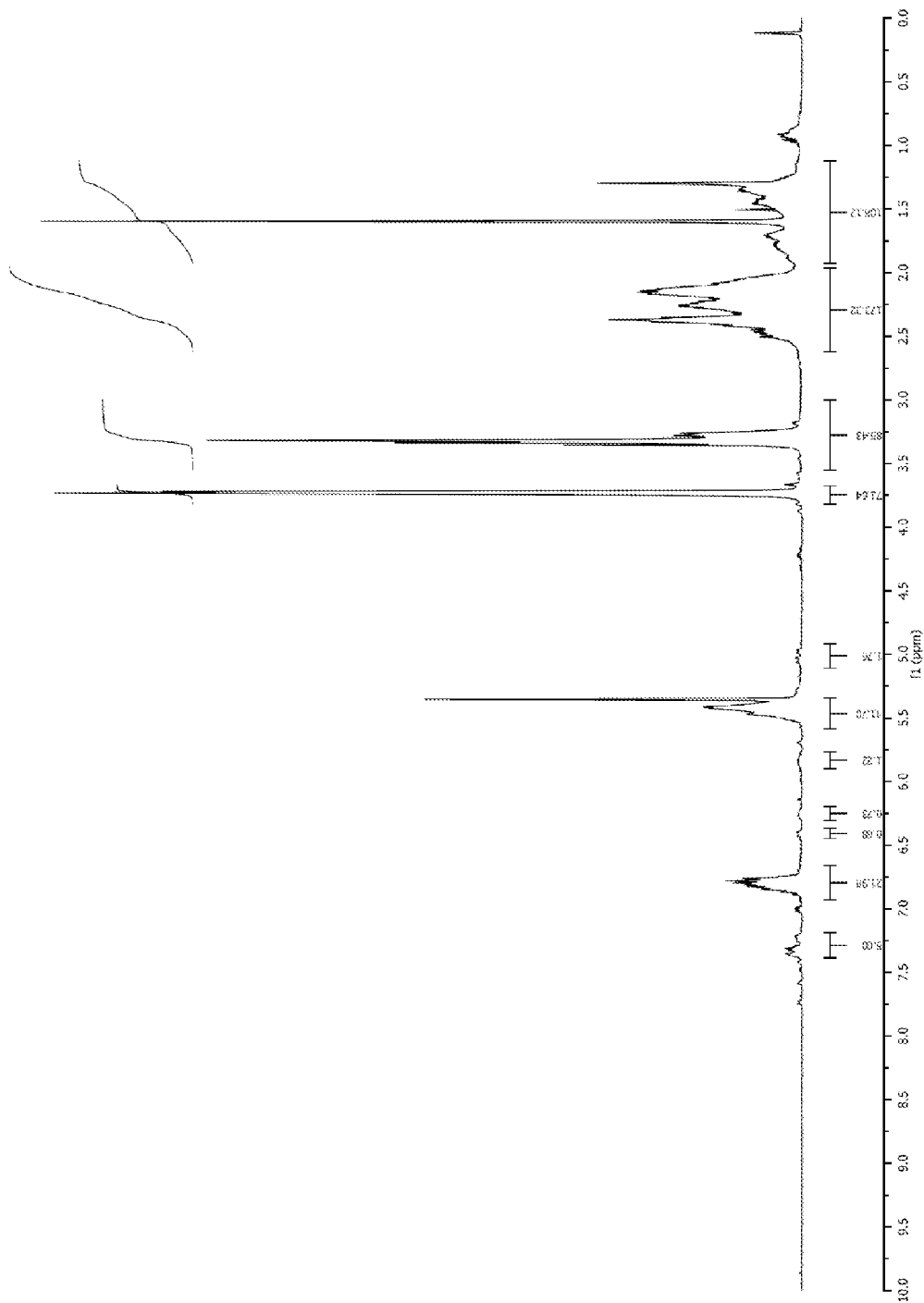
FIG. 35 depicts the $^1$H-NMR spectrum of $(2\text{-}17)_{20}$.
Figure 36:
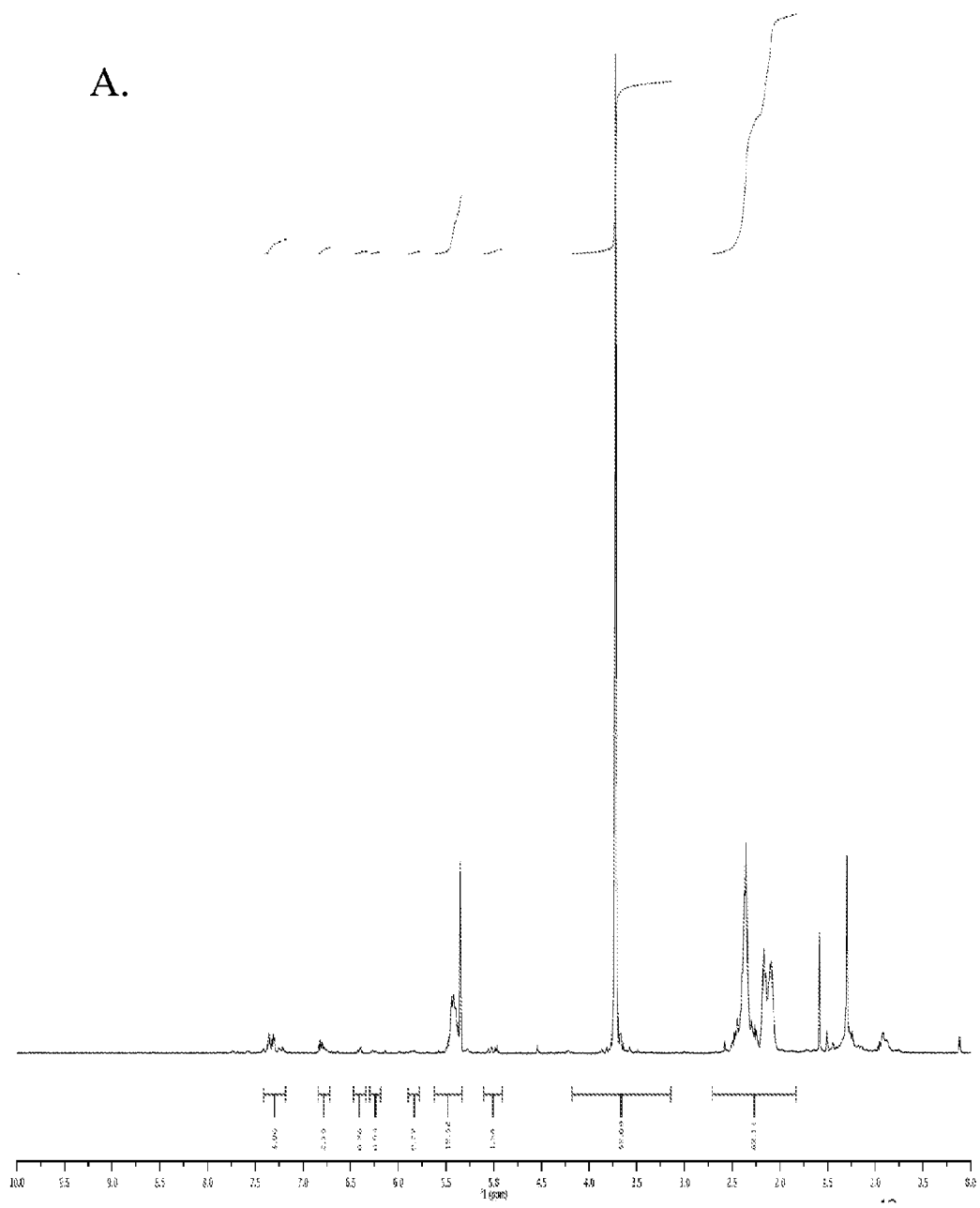
FIG. 36 depicts the $^1$H-NMR spectrum of $(2\text{-}7)_{20}$ for polymers produced with varying equivalents of 7. Panel A: 24 equivalents of 7. Panel B: 40 equivalents of 7. Panel C: 160 equivalents of 7.
Figure 37:
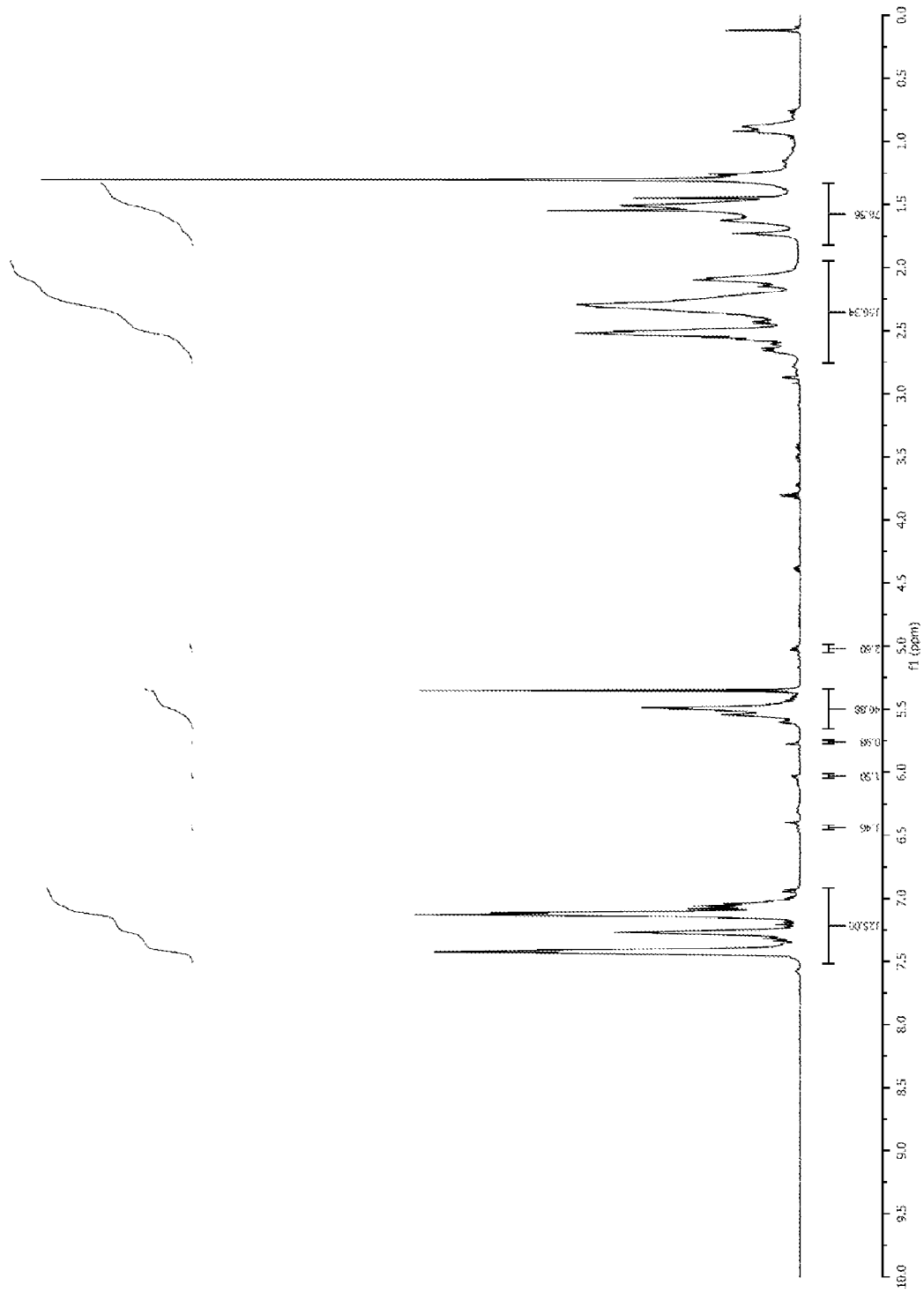
FIG. 37 depicts the $^1$H-NMR spectrum of $(11\text{-}5)_{20}$.
Figure 38:
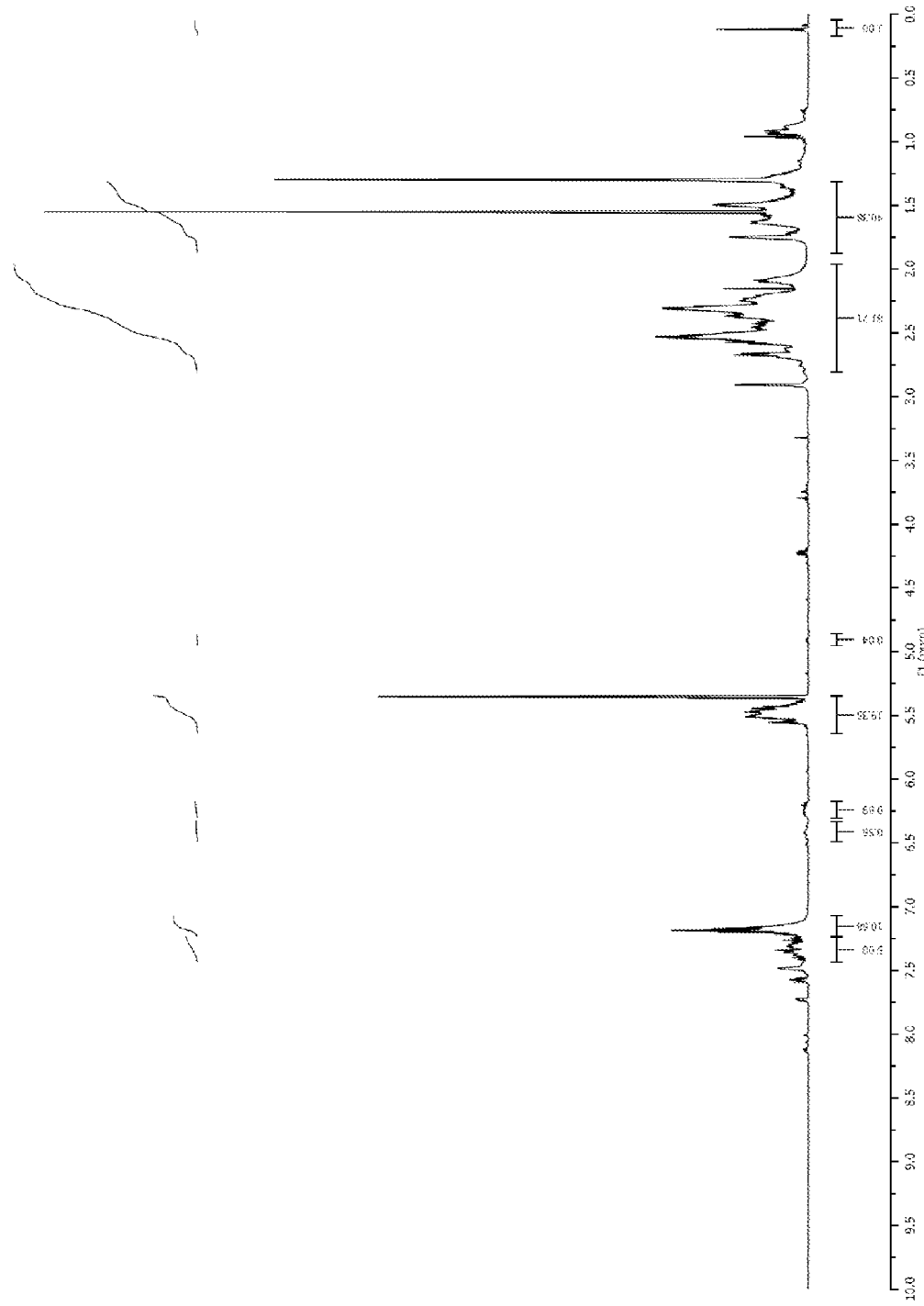
FIG. 38 depicts the $^1$H-NMR spectrum of $(13\text{-}5)_{10}$.
Figure 39:
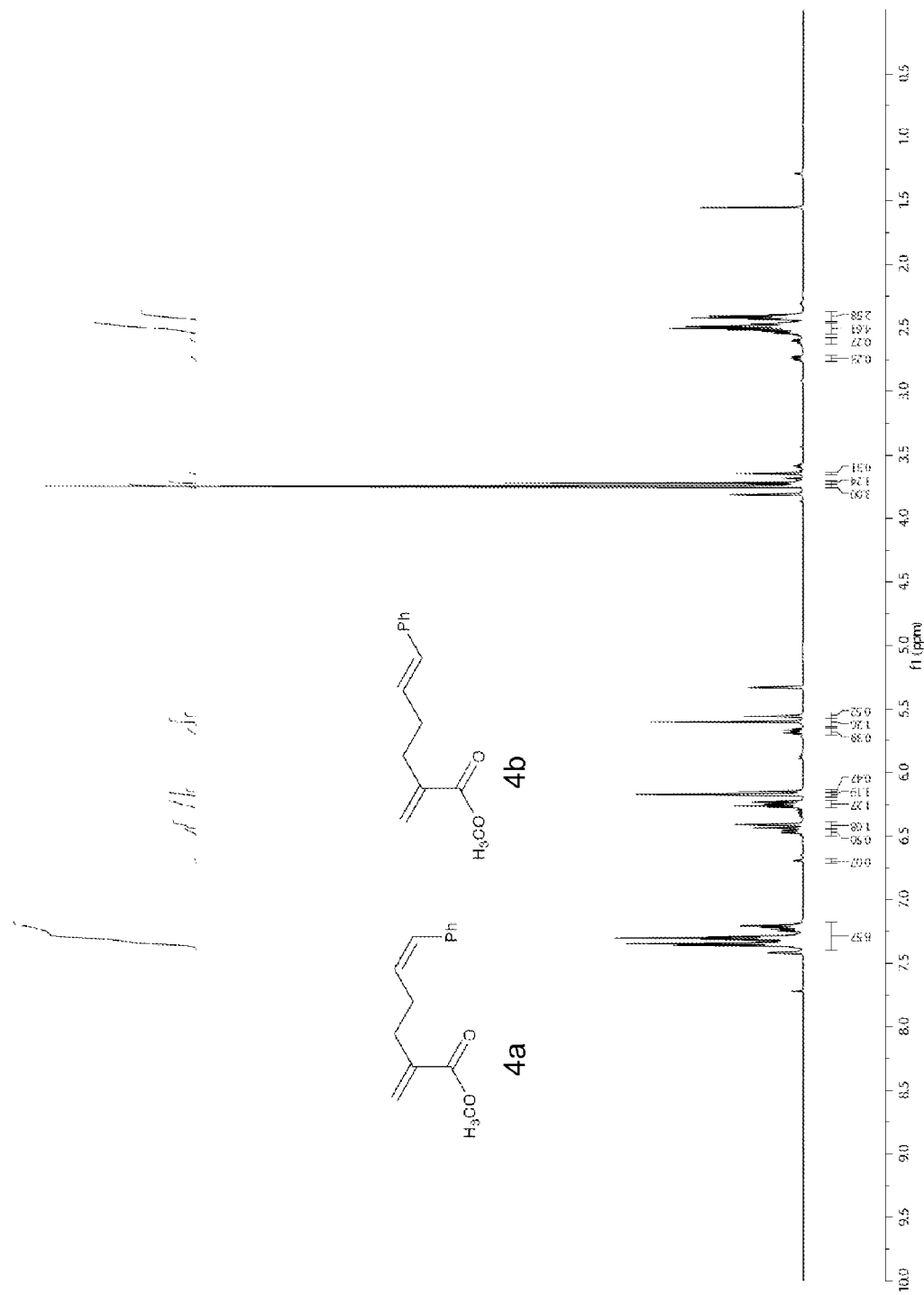
FIG. 39 depicts the $^1$H-NMR spectrum of 4a and 4b.
Figure 40:
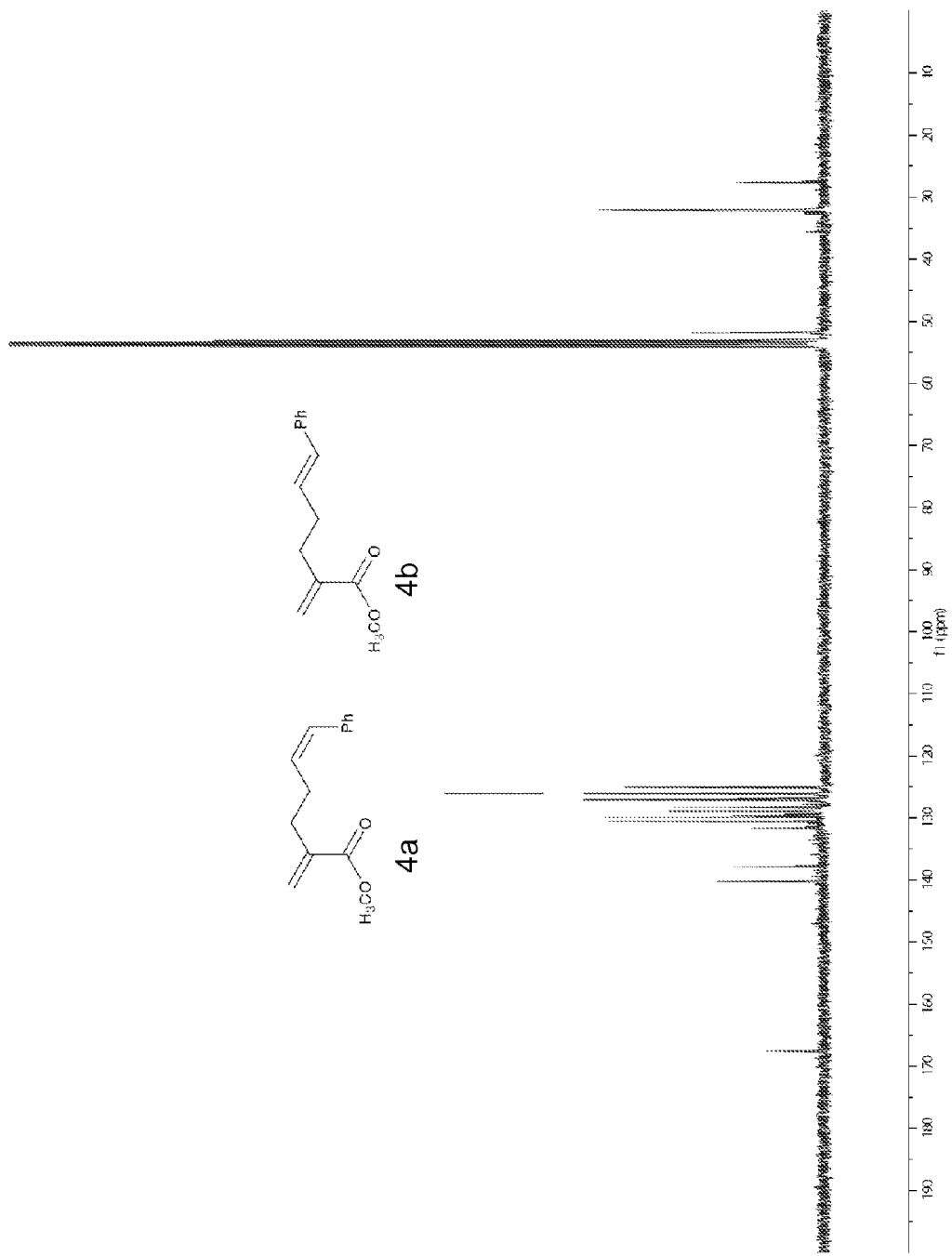
FIG. 40 depicts the $^{13}$C-NMR spectrum of 4a and 4b.

Cyclobutene 2 (0.60 mmol), cyclohexene 5 (1.20 mmol) and 1 (0.003 mmol) were mixed in $CD_2Cl_2$ (600 µl) in an NMR tube. The reaction was maintained for 6 h to reach 73% completion. The crude solution was evaporated to remove solvents, and was purified by flash column chromatography (acetone:$CH_2Cl_2$/3:97) to generate polymer 6f (48 mg, 41%). DP=74. According to GPC chromatographic analysis, the copolymer had a bimodal molecular weight distribution (FIG. 10). $M_n^{calc}$=29010. The overall GPC result: $M_n^{CPC}$=7749, $M_w^{GPC}$=18501, PDI=2.4. The individual peaks were fitted using OriginPro 7.5 (OriginLab Corp.), and the molecular weight and PDI data of each peak were calculated (FIG. 11).

Peak A: $M_n^{GPC}$=17703. $M_w^{GPC}$=20388. PDI=1.2. Peak B: $M_n^{GPC}$=1038. $M_w^{GPC}$=3539. PDI=3.4.

Cyclobutene 2 (0.60 mmol), cyclohexene 5 (1.20 mmol) and 1 (0.003 mmol) were mixed in $CD_2Cl_2$ (600 μL) in an NMR tube. The reaction was maintained for 1.5 h and quenched at 50% completion. DP=50. According to GPC chromatographic analysis, the copolymer had a bimodal molecular weight distribution (FIG. 10). $M_n^{calc}$=29010. The overall GPC result: $M_n^{GPC}$=3201. $M_w^{GPC}$=18106. PDI=5.7. Peak A: $M_n^{GPC}$=25088. $M_w^{GPC}$=28697. PDI=1.1. Peak B: $M_n^{GPC}$=1383. $M_w^{GPC}$=2143. PDI=1.5.

$(2-5)_{200}$: (6f)

Cyclobutene 2 (1.20 mmol), cyclohexene 5 (2.40 mmol) and 1 (0.006 mmol) were mixed in $CD_2Cl_2$ (600 μl) in an NMR tube. The reaction was maintained for 6 h to reach 75% completion.

$(2-9)_{10}$:

Cyclobutene 2 (0.06 mmol), cyclohexene 9 (0.12 mmol) and 1 (0.006 mmol) were mixed in $CD_2Cl_2$ (600 μl) in an NMR tube. No ROMP was observed.

$(2-10)_{10}$:

Cyclobutene 2 (0.06 mmol), cyclohexene 10 (0.12 mmol) and 1 (0.006 mmol) were mixed in $CD_2Cl_2$ (600 μl) in an NMR tube. No ROMP was observed.

$(11-5)_{20}$: (12c)

Cyclobutene 11 (0.12 mmol), cyclohexene 5 (0.24 mmol) and 1 (0.006 mmol) were mixed in $CD_2Cl_2$ (600 μl) in an NMR tube. The reaction was maintained for 4 h to reach 96% completion. The solvent was removed from the crude mixture in vacuo and the residue was purified by flash column chromatography (100% $CH_2Cl_2$) to provide polymer 12c (16 mg, 55%). $^1$H (500 MHz, $CD_2Cl_2$) δ7.44-6.95 (m, 125H), 6.40 (m, 0.5H+0.5H), 6.31 (b, 0.5H), 6.03 (b, 1H), 5.78 (b, 0.5H), 5.60-5.40 (b, m, 38H), 5.03 (m, 2H), 2.66-2.10 (b, m, 160H), 1.73-1.42 (b, m, 80H). DP=96. $M_n^{calc}$=5224. $M_n^{GPC}$=1572. $M_w^{GPC}$=3302. PDI=2.1.

$(13-5)_{10}$: (14b)

Cyclobutene 13 (0.06 mmol), cyclohexene 5 (0.12 mmol) and 1 (0.006 mmol) were mixed in $CD_2Cl_2$ (600 μl) in an NMR tube. The reaction was maintained for 13 h to reach 95% completion. The solvent was removed from the crude mixture in vacuo and the residue was purified by flash column chromatography (100% $CH_2Cl_2$) to generate polymer 14b (13 mg, 61%). $^1$H (500 MHz, $CD_2Cl_2$) δ 7.26-7.40 (m, 5H), 7.25-7.16 (m, 10H), 6.42 (m, 1H), 6.27 (m, 2H), 5.47 (m, 18H), 4.90 (2H), 2.75-2.09 (m, 80H), 1.75-1.38 (m, 40H).

$(2-15)_{20}$: (16c)

Cyclobutene 2 (0.12 mmol), cyclohexene 15 (0.24 mmol) and 1 (0.006 mmol) were mixed in $CD_2Cl_2$ (600 μl) in an NMR tube. The reaction was maintained for 4 h to reach 95% completion. The solvent was removed from the crude mixture in vacuo and the residue was purified by flash column chromatography (100% $CH_2Cl_2$) to provide polymer 16c (16 mg, 55%). $^1$H (500 MHz, $CD_2Cl_2$) δ 7.41-7.21 (m, 5H), 6.84 (bs, 20H), 6.41 (m, 1H), 6.27 (m, 1H), 5.86 (m, 1H), 5.48 (bs, 38H), 5.02 (m, 2H), 3.73 (bs, 60H), 2.45-2.02 (m, 160H), 1.76-0.74 (m, 120).

$(2-17)_{20}$: (18c)

Cyclobutene 2 (0.12 mmol), cyclohexene 17 (0.24 mmol) and 1 (0.006 mmol) were mixed in $CD_2Cl_2$ (600 μl) in an NMR tube. The reaction was maintained for 4 h to reach 95% completion. The solvent was removed from the crude mixture in vacuo and the residue was purified by flash column chromatography (100% $CH_2Cl_2$) to generate polymer 18c (15 mg, 59%). $^1$H (500 MHz, $CD_2Cl_2$) δ 7.41-7.21 (m, 5H), 6.83 (m, 20H), 6.42 (m, 1H), 6.27 (m, 1H), 5.83 (m, 1H), 5.42 (m, 38H), 5.02 (m, 2H), 3.72 (bs, 60H), 3.34-3.17 (m, 100H), 2.47-2.06 (m, 160H), 1.78-1.24 (m, 60H). DP=95. $M_n^{calc}$=4264. $M_n^{GPC}$=1506. $M_w^{GPC}$=3719. PDI=2.5.

$(2-7)_{20}$ (24 equiv. of 7), (8c):

Cyclobutene 2 (0.12 mmol), cyclohexene 7 (0.144 mmol) and 1 (0.006 mmol) were mixed in $CD_2Cl_2$ (600 μl) in an NMR tube. The reaction was maintained for 3 h to reach 97% completion. The solvent was evaporated, and the residue was purified by flash column chromatography (acetone:$CH_2Cl_2$/4:96) to provide polymer $(2-7)_{20}$ as a sticky oil (17.4 mg, 71%). $^1$H (500 MHz, $CD_2Cl_2$) δ 7.41-7.21 (m, 5H), 6.78 (t, J=2.5 Hz, 2H), 6.39 (m, 1H), 6.27 (m, 1H), 5.43 (m, 20H), 5.06-5.02 (d, J=2.0 Hz, 1H), 4.98-4.97 (d, J=0.5 Hz, 1H), 3.72 (s, 60H), 2.36-2.09 (m, 80H). Polymer $(2-7)_{20}$ was further purified by flash chromatography (acetone:$CH_2Cl_2$/4:96) to provide cyclic polymer cyc-$(2-7)_{20}$ as a sticky oil (3.3 mg). Polymer cyc-$(2-7)_{20}$ was characterized by $^1$H-NMR spectroscopy and the structures are shown below. $^1$H-NMR (500 MHz, $CDCl_3$) δ 6.84 (t, J=1.0 Hz, 1H) 5.48-5.36 (m, 5H), 3.75 (m, 18H), 2.47-2.12 (m, 24H).

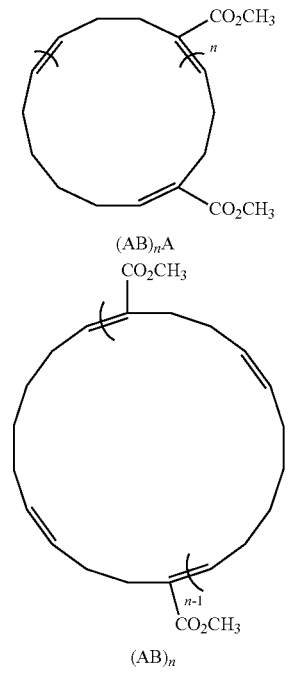

A: ring-opened cyclobutene subunit
B: ring-opened cyclohexene subunit $(2-7)_{20}$ (40 equiv. of 7), (8c):

Cyclobutene 2 (0.12 mmol), cyclohexene 7 (0.24 mmol) and 1 (0.006 mmol) were mixed in $CD_2Cl_2$ (600 μl) in an NMR tube. The reaction was maintained for 3 h to reach 97% completion.

$(2-7)_{20}$ (160 equiv. of 7), (8c):

Cyclobutene 2 (0.12 mmol), cyclohexene 7 (0.96 mmol) and 1 (0.006 mmol) were mixed in $CD_2Cl_2$ (600 μl) in an NMR tube. The reaction was maintained for 3 h to reach 97% completion.

$(5)_{20}$:

Cyclohexene 5 (0.12 mmol) and 1 (0.006 mmol) were mixed in $CD_2Cl_2$ (600 μl) in an NMR tube. No ROMP or ROM was observed.

$(2)_{10}$:

Methyl cyclobut-1-enecarboxylate 2 (0.06 mmol) and 1 (0.006 mmol) were mixed in $CD_2Cl_2$ (600 μl) in an NMR tube. The reaction was maintained for 5 h and only 10% reaction of 2 was observed.

(21-5)$_{25}$: (22g) and (23g)

Cyclobutene 21 (0.15 mmol), cyclohexene 5 (0.30 mmol) and 1 (0.006 mmol) were mixed in CD$_2$Cl$_2$ (600 µL) in an NMR tube. The reaction was maintained for 5 h at rt to reach 90% completion. The crude solution was evaporated to remove solvent, and the residue was purified by flash column chromatography (acetone:CH$_2$Cl$_2$/5:95) to provide polymer 22g (21 mg, 51%). $^1$H NMR (500 MHz, CD$_2$Cl$_2$) δ 7.40-7.21 (m, 5H), 6.78 (b, 25H), 6.43 (m, 1H), 6.27 (m, 1H), 5.85 (m, 1H), 5.44 (b, 42H), 4.17 (b, 50H), 3.63 (b, 50H), 2.44-2.02 (m, 188H), 1.88 (m, 100H), 1.52-1.44 (b, 88H). Polymer 22g and trimethylamine aqueous solution (45% wt, 1 mL) were mixed in acetonitrile (2 mL). The solution was heated to 70° C. for 4 h. The crude solution was evaporated to remove solvent to provide polymer 23g as a brown powder. $^1$H NMR (600 MHz, D$_2$O) δ 7.50-7.27 (m, 5H), 6.91 (b, 25H), 6.39 (b, 1H), 6.28 (b, 1H), 5.89 (b, 1H), 5.45 (b, 44H), 4.25 (b, 50H), 3.44 (b, 50H), 3.19 (s, 225H), 2.40-2.04 (m, 188H), 1.94 (m, 50H), 1.84 (m, 50H), 1.47 (m, 88H).

(21-5)$_{25}$: (39g) and (40g)

Cyclobutene 21 (0.15 mmol), cyclohexene 5 (0.30 mmol) and 28 (0.006 mmol) were mixed in CD$_2$Cl$_2$ (600 µL) in an NMR tube. The reaction was maintained for 5 h at rt to reach 90% completion. The crude solution was evaporated to remove solvent, and the residue was purified by flash column chromatography (acetone:CH$_2$Cl$_2$/5:95) to provide polymer 39g (16 mg, 39%). $^1$H NMR (600 MHz, CDCl$_3$) δ 6.75 (b, 25H), 5.39 (b, 30H), 4.16 (b, 50H), 3.57 (b, 50H), 2.48-1.98 (164H), 1.85 (b, 100H), 1.49-1.37 (b, 64H). Polymer 39g and trimethylamine aqueous solution (45% wt, 1 mL) were mixed in acetonitrile (2 mL). The solution was heated to 70° C. for 4 h. The crude solution was evaporated to remove solvent to provide polymer 40g as a brown powder. $^1$H NMR (600 MHz, D$_2$O) δ 6.89 (b, 25H), 5.42 (b, 30H), 4.28 (s, 50H), 3.42 (s, 50H), 3.19 (b, 225H), 2.42-1.26 (m, 328H).

(21-15)25: (29g) and (30g)

Cyclobutene 42 (0.095 mmol), cyclohexene 15 (0.19 mmol) and 1 (0.0038 mmol) were mixed in CDCl$_3$ (600 µL) in an NMR tube. The reaction was maintained for 3 h at 50° C. to reach 94% completion. The crude solution was evaporated to remove solvent, and the residue was purified by flash column chromatography (acetone:CH$_2$Cl$_2$/10:90) to provide polymer 52 (22 mg, 81%). $^1$H NMR (600 MHz, CD$_2$Cl$_2$) δ 7.38-7.21 (m, 5H), 6.75 (b, 25H), 6.39 (b, 1H), 6.22 (b, 1H), 5.81 (b, 1H), 5.42 (b, 34H), 4.14 (b, 50H), 3.61 (b, 50H), 2.36-2.01 (m, 172H), 1.84 (m, 100H), 1.57-1.36 (m, 108H). Polymer 52 and trimethylamine aqueous solution (45% wt, 1 mL) were mixed in acetonitrile (2 mL). The solution was heated to 70° C. for 4 h. The crude solution was evaporated to remove solvent to provide polymer 55 as a brown powder. $^1$H NMR (600 MHz, D$_2$O) δ 7.36-7.15 (m, 5H), 6.75 (b, 17H), 5.27 (b, 13H), 4.08 (b, 34H), 3.26 (b, 34H), 3.02 (b, 153H), 2.40-1.97 (m, 124H), 1.76-1.66 (b, 68H), 1.37-1.08 (m, 84H).

(21-26)$_{25}$: (31g) and (32g)

Cyclobutene 21 (0.085 mmol), cyclohexene 26 (0.85 mmol) and 1 (0.0034 mmol) were mixed in CDCl$_3$ (600 µL) in an NMR tube. The reaction was maintained for 3 h at 50° C. to reach 92% completion. The crude solution was evaporated to remove solvent, and the residue was purified by flash column chromatography (acetone:CH$_2$Cl$_2$/10:90) to provide polymer 31g (16 mg, 53%). $^1$H NMR (600 MHz, CD$_2$Cl$_2$) δ 7.43-7.21 (m, 5H), 6.73 (s, 31H), 6.36 (b, 1H), 6.21 (b, 1H), 5.83 (b, 1H), 5.56-5.40 (b, 44H), 4.15 (b, 62H), 3.60 (b, 62H), 3.17 (b, 46H), 2.44-2.08 (m, 216H), 1.85-1.82 (m, 124H), 1.61-1.51 (m, 115H), 0.92 (m, 69H). Polymer 31g and trimethylamine aqueous solution (45% wt, 1 mL) were mixed in acetonitrile (2 mL). The solution was heated to 70° C. for 4 h. The crude solution was evaporated to remove solvent, diluted with water and washed by Et$_2$O to provide polymer 32g as a brown powder. $^1$H NMR (600 MHz, D$_2$O) δ 7.53-7.31 (m, 5H), 6.86 (m, 30H), 5.47 (b, 48H), 4.28 (b, 60H), 3.41 (b, 60H), 3.17 (b, 320H), 2.57-2.18 (m, 220H), 1.93-1.56 (m, 125H), 0.94 (b, 75H).

(21-27)$_{25}$: (33g) and (34g)

Cyclobutene 21 (0.035 mmol), cyclohexene 27 (0.35 mmol) and 1 (0.00138 mmol) were mixed in CDCl$_3$ (600 µL) in an NMR tube. The reaction was maintained for 5 h at 50° C. to reach 96% completion. The crude solution was evaporated to remove solvent, and the residue was purified by flash column chromatography (acetone:CH$_2$Cl$_2$/10:90) to provide polymer 33g (9 mg, 61%). $^1$H NMR (500 MHz, CD$_2$Cl$_2$) δ 7.41-7.23 (m, 5H), 6.76 (b, 22H), 6.42 (b, 1H), 6.23 (b, 1H), 5.94 (b, 1H), 5.41 (b, 38H), 4.17 (b, 44H), 3.61 (b, 44H), 3.22 (40H), 2.53-2.11 (m, 168H), 1.86 (m, 88H), 1.62-1.50 (m, 60H), 1.32 (m, 240H), 0.91 (m, 60H). Polymer 33g and trimethylamine aqueous solution (45% wt, 1 mL) were mixed in acetonitrile (2 mL). The solution was heated to 70° C. for 4 h. The crude solution was evaporated to remove solvent, diluted with water and washed by Et$_2$O to provide polymer 34g as a brown powder. $^1$H NMR (600 MHz, CD$_2$Cl$_2$) δ 7.53-7.31 (m, 5H), 6.89 (b, 25H), 5.49 (b, 48H), 4.34 (b, 50H), 3.46 (b, 50H), 3.17 (b, 275H), 2.61-2.11 (m, 200H), 1.91-1.31 (m, 375H), 0.91 (b, 75H).

(24-5)$_{25}$: (35g) and (36g)

Cyclobutene 24 (0.15 mmol), cyclohexene 5 (0.30 mmol) and 1 (0.006 mmol) were mixed in CDCl$_3$ (600 µL) in an NMR tube. The reaction was maintained for 80 min at 50° C. to reach 97% completion. The crude solution was evaporated to remove solvent, and the residue was purified by flash column chromatography (acetone:CH$_2$Cl$_2$/10:90) to provide polymer 35g (26 mg, 49%). $^1$H NMR (600 MHz, CD$_2$Cl$_2$) δ 7.40-7.20 (m, 5H), 6.75 (b, 25H), 6.36 (m, 1H), 6.22 (b, 1H), 5.79 (b, 1H), 5.39 (b, 38H), 4.67 (b, 25H), 4.12 (b, 50H), 3.13 (b, 50H), 2.44-2.02 (m, 180H), 1.69-1.28 (m, 405H). Polymer 35g and trifluorine acetic acid (TFA) (2 mL) were mixed in CH$_2$Cl$_2$ (2 mL). The solution was stirred at rt for 2 h. The crude solution was purged by Ar gas flow to remove solvent to provide polymer 36g as a brown powder. $^1$H NMR (600 MHz, D$_2$O) δ 7.34-7.06 (m, 5H), 6.70 (b, 18H), 5.24 (b, 22H)), 4.04 (m, 36H), 2.94 (b, 36H), 2.34-1.84 (m, 120H), 1.66-1.09 (m, 282H).

(25-5)$_{25}$: (37g) and (38g)

Cyclobutene 25 (0.15 mmol), cyclohexene 5 (0.30 mmol) and 1 (0.006 mmol) were mixed in CDCl$_3$ (600 µL) in an NMR tube. The reaction was maintained for 80 min at 50° C. to reach 97% completion. The crude solution was evaporated to remove solvent, and the residue was purified by flash column chromatography (acetone:CH$_2$Cl$_2$/10:90) to provide polymer 37g (51 mg, 73%). $^1$H-NMR (600 MHz, CD$_2$Cl$_2$) δ 8.56 (s, 50H), 7.41-7.20 (m, 5H), 6.79 (bs, 25H), 6.36 (m, 1H), 6.22 (b, 1H), 5.79 (b, 1H), 5.40 (bs, 48H), 4.24 (b, 50H), 3.68 (b, 50H), 2.42-1.97 (m, 200H), 2.60-1.20 (m, 550H). Polymer 37g and TFA (2 mL) were mixed in CH$_2$Cl$_2$ (2 mL). The solution was stirred at rt for 2 h. The crude solution was purged by Ar gas flow to remove solvent to provide polymer 38g as a brown powder. $^1$H-NMR (600 MHz, D$_2$O) δ 7.39-7.17 (m, 5H), 6.86 (bs, 25H), 5.36 (bs, 48H), 4.27 (bs, 50H), 3.55 (bs, 50H), 2.60-1.98 (m, 200H), 1.38 (bs, 100H).

(2-42)$_{20}$: (43c)

Cyclobutene 2 (0.12 mmol), 1-methylcyclopentene 42 (0.24 mmol) and 41 (0.006 mmol) were mixed in CDCl$_3$ (600 µl) in an NMR tube. The reaction was maintained at rt for 3 h to reach 50% completion.

Preparative Scale AROMP (2)$_1$: (4a and 4b)

A solution of 2 (40.0 mg, 0.357 mmol) in dry $CH_2Cl_2$ (4 ml) was added to a solution of precatalyst 1 (474 mg, 0.536 mmol) in dry $CH_2Cl_2$ (4 ml) at rt. The solution was stirred at room temperature for 20 h and ethyl vinyl ether (5 ml, 52.2 mmol) was added to the reaction mixture. After 60 min, the solvent was evaporated and the residue was purified by silica column chromatography with $CH_2Cl_2$. The purified fractions were evaporated to afford the products 4a and 4b (42.1 mg, 55%) with E/Z molar ratio 2.3/1. $^1$H-NMR (600 MHz, $CD_2Cl_2$) 1-mer 4a Z-isomer δ 7.36-7.19 (m, 5H), 6.47 (d, J=12.6 Hz, 1H), 6.15 (s, 1H), 5.68 (dt, J=11.4, 7.8 Hz, 1H), 5.60 (s, 1H), 3.72 (s, 3H), 2.50 (m, 2H), 2.43 (m, 2H). 1-mer 4b E-isomer δ 7.36-7.19 (m, 5H), 6.42 (d, J=16.2 Hz, 1H), 6.25 (dt, J=22.8, 6.0 Hz, 1H), 6.17 (s, 1H), 5.60 (s, 1H), 3.75 (s, 3H), 2.50 (m, 2H), 2.43 (m, 2H). $^{13}$C-NMR (100 MHz, $CD_2Cl_2$) 1-mer 4b Z-isomer δ 167.9, 140.6, 138.1, 132.1, 130.8, 130.0, 129.3, 128.6, 127.2, 125.5, 52.2, 32.6, 28.0. 1-mer 4b E-isomer δ 168.0, 140.7, 138.1, 131.0, 130.3, 129.0, 128.7, 127.5, 126.5, 52.2, 32.4, 32.3. LC-MS (APCI): Peak time=2.18 min, m/z calcd for $C_{14}H_{16}O_2$ [M+H]$^+$ 217.12, found 217.21.

(2-5)$_3$: (6a)

Cyclobutene 2 (0.28 mmol, 31 mg) and 1 (0.093 mmol, 82 mg) were mixed in $CH_2Cl_2$ (2 ml) and stirred for 3 h at rt. Then cyclohexene 5 (0.56 mmol, 56 μl) was added the solution, which was stirred for 3 h. Then the reaction was quenched with ethylvinyl ether (500 μl) and was stirred for 1 h. The crude solution was evaporated to remove solvent, and the residue was purified by flash column chromatography (acetone:$CH_2Cl_2$/4:96) to provide polymer 6a as a sticky oil (47 mg, 74%). $^1$H-NMR (125 MHz, $CD_2Cl_2$) δ7.35-7.21 (m, 5H), 6.80 (m, 6H), 6.42 (d, J=16 Hz, 1H), 6.26 (m, 1H), 5.84 (b, 1H), 5.44 (b, 4H), 5.04 (d, J=17 Hz, 1H), 4.97 (d, J=15 Hz, 1H), 3.73 (b, 9H), 2.61-2.04 (b, 24H), 1.54 (b, 12H). $^{13}$C (500 MHz, $CD_2Cl_2$) δ 170.70 (m), 146.00-145.08 (m), 134.30-132.03 (m), 131.10, 130.77, 129.51, 128.53, 127.51, 126.91, 54.00, 36.20-34.11 (m), 32.34-28.48 (m).

(2-5)$_{10}$: (6b)

Cyclobutene 2 (0.23 mmol, 26 mg) and 1 (0.024 mmol, 21 mg) were mixed in $CH_2Cl_2$ (2.3 ml) and stirred for 25 min at rt. Then cyclohexene 5 (0.47 mmol, 47 μl) was added to the solution, which was stirred for 4 h. Then the reaction was quenched with ethylvinyl ether (350 μl), and was stirred for 1 h. The crude solution was evaporated to remove solvent, and the residue was purified by flash column chromatography (acetone:$CH_2Cl_2$/1:99) to provide polymer 6b as a sticky oil (32 mg, 71%). $^1$H-NMR (500 MHz, $CD_2Cl_2$) δ 7.41-7.21 (m, 5H), 6.77 (b, 10H), 6.41 (d, J=15.5 Hz, 1H), 6.26 (d, J=16.0 Hz, 1H), 5.84 (b, 1H), 5.49 (b, 18H), 5.04 (d, J=17.0 Hz, 1H), 4.97 (d, J=10.0 Hz, 1H), 3.72 (s, 30H), 2.56-2.02 (b, m, 80H), 1.46 (b, 40H). The broad signal centered at 7.29 ppm was assigned to the phenyl group. All the internal trisubstituted olefinic protons exhibited a broad signal centered at 6.78 ppm, which confirmed all the internal trisubstituted olefin bonds carried the E-configuration. And all the internal disubstituted olefinic protons also showed a broad signal centered at 5.39 ppm. The peaks at 5.87 ppm and 5.02 ppm correspond to the terminal vinyl protons, while the peaks at 6.42 ppm and 6.30 ppm could be assigned to the two styrenyl olefinic protons with E-configuration. The relative intensities of all these signals were (5:11:18:1:1:2:1) (7.29, 6.78, 5.39, 6.42, 6.30, 5.02, 5.89 ppm), which clearly indicated that polymer 6b contained nearly equal amounts of repeating units A and B generated from monomers 2 and 5, respectively.

(2-5)$_{20}$: (6c)

Cyclobutene 2 (0.47 mmol, 53 mg) and 1 (0.024 mmol, 21 mg) were mixed in $CH_2Cl_2$ (2 ml) and stirred for 25 min at rt. Then cyclohexene 5 (0.94 mmol, 95 μl) was add to the solution, which was stirred for 5 h thereafter. Then the reaction was quenched with ethylvinyl ether (350 μl), and was stirred for 1 h. The crude solution was evaporated to remove solvent, and was purified by flash column chromatography (acetone:$CH_2Cl_2$/4:96) to provide polymer 6c as a sticky oil (67 mg, 74%). Polymer 6c was characterized by $^1$H NMR, $^{13}$C NMR, gHMQC, $^1$H—$^1$H gCOSY and $^{13}$C-APT spectroscopy (Table 3).

To assess antimicrobial activity, polymers of the invention are added in various concentrations to growing bacterial cultures. For example, a bacterial stock solution of *Escherichia coli* is diluted into fresh medium and grown overnight at 37° C. Samples of the overnight culture are grown for 3 h, the $OD_{600}$ is measured, and solutions having 0.001 $OD_{600}$ (about $10^5$ cells/ml) are prepared. Various concentrations of a test compound are added to individual cultures and the lowest concentration which provides a desired endpoint (e.g., no growth, 90% inhibition of cell growth, 75% inhibition of cell growth) is determined.

Hemolytic activity can also be determined, for example by incubation of a 0.35% (v/v) suspension of fresh human erythrocytes in a 10 mM TRIS buffer containing 150 mM NaCl at pH 7.0 with various amounts of polymer. After incubation for 30 min at 37° C., the suspensions are concentrated at 1000× "g" for 5 min. An aliquot of the supernatant is diluted with buffer and the $OD_{414}$ of the solution is measured to quantify released hemoglobin.

TABLE 3

$^{1H}$-NMR, $^{13}$C-NMR, $^1$H-$^1$H gCOSY, $^{13}$C-APT, and $^1$H-$^{13}$C gHMQC data for compound 6c (500, 100, 500, 100 and 500/125 MHz, $CD_2Cl_2$).$^a$

| No. | $δ_H$ (J in Hz) | $δ_C$ | $^1$H-$^1$H gCOSY | $^{13}$C-APT |
|---|---|---|---|---|
| 1 | 4.97 d (15) | | | |
|  | 5.04 d (17) | | | |
| 2 | 5.79 b | 129.5-132.5 | | CH |
| 3 | 2.04-2.50 b | 26.7-32.5 | | $CH_2$ |
| 4 | 1.42 b | 29.2-29.9 | | $CH_2$ |
| 5 | 1.42 b | 29.2-29.9 | | $CH_2$ |
| 6 | 2.04-2.50 b | 26.7-32.5 | | $CH_2$ |
| 7 | 6.74 b | 142.7-143.7 | | CH |
| 8 | | 131.8 | | q |
| *9* | *2.04-2.50 b* | *26.7-32.5* | | *$CH_2$* |
| *10* | *2.04-2.50 b* | *26.7-32.5* | *11* | *$CH_2$* |
| *11* | *5.40 m* | *129.5-131.1* | *10* | *CH* |
| *12* | *5.40 m* | *129.9-131.0* | *13* | *CH* |
| *13* | *2.04-2.50 b* | *26.7-32.5* | *12, 14, 16* | *$CH_2$* |
| *14* | *1.42 b* | *29.2-29.9* | *13, 15* | *$CH_2$* |
| *15* | *1.42 b* | *29.2-29.9* | *14, 16* | *$CH_2$* |
| *16* | *2.04-2.50 b* | *26.7-32.5* | *13, 15, 17* | *$CH_2$* |
| *17* | *6.74 b* | *142.7-143.7* | *16* | *CH* |
| *18* | | *131.8* | | *q* |
| 19 | 2.04-2.50 b | 26.7-32.5 | | $CH_2$ |
| 20 | 2.04-2.50 b | 26.7-32.5 | | $CH_2$ |
| 21 | 6.24 b | 129.7 | | CH |
| 22 | 6.39 d (16) | 129.7 | | CH |
| 23 | | 131.9 | | q |
| 24-28 | 7.19-7.33 m | 128.3-129.7 | | CH |
| 29 | | 168.2 | | q |
| 30 | 3.70 s | 51.8 | | $CH_3$ |

$^a$Rows in italic correspond to the atoms in the repeating polymer unit.

REFERENCES

1. Love, J. A.; Morgan, J. P.; Trnka, T. M.; Grubbs, R. H., *Angew Chem Int Edit* 2002, 41, 4035-4037.

2. Campbell, A.; Rydon, H. N., *J. Chem. Soc.* 1953, 3002-3008.
3. Lee, J. C.; Parker, K. A.; Sampson, N. S., *J. Am. Chem. Soc.* 2006, 128, 4578-4579.
4. Griffin, R. J.; Arris, C. E.; Bleasdale, C.; Boyle, F. T.; Calvert, A. H.; Curtin, N. J.; Dalby, C.; Kanugula, S.; Lembicz, N. K.; Newell, D. R.; Pegg, A. E.; Golding, B. T., *J. Med. Chem.* 2000, 43, 4071-4083.
5. Mathias, L. J., *Synthesis-Stuttgart.* 1979, 561-576.
6. Wohl, R. A., *Synthesis* 1974, 38-40.
7. Hashiyama, T.; Morikawa, K.; Sharpless, K. B., *J. Org. Chem.* 1992, 57, 5067-5068.
8. Marcune, B. F.; Karady, S.; Reider, P. J.; Miller, R. A.; Biba, M.; DiMichele, L.; Reamer, R. A., *J. Org. Chem.* 2003, 68, 8088-8091.

We claim:

1. A method for producing a polymer comprising the repeating unit (Ia) or (Ib):

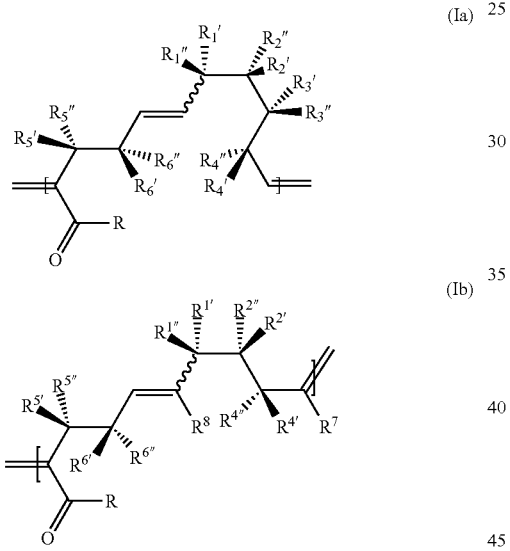

which comprises contacting an olefin of structure (IIa) or (IIb) with a cyclobutene of structure (III)

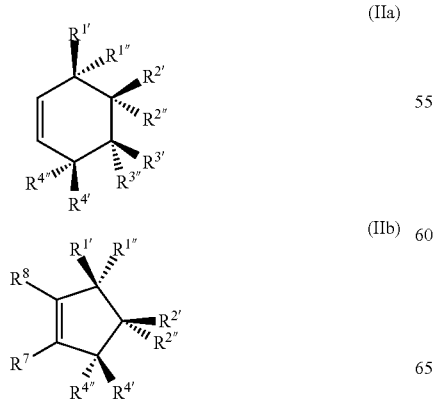

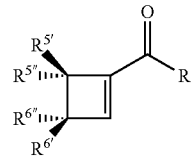

in the presence of an olefin metathesis catalyst, wherein

R is selected form the group consisting of H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkylthio, $C_2$-$C_{20}$ alkenyloxy, $C_2$-$C_{20}$ alkenylthio, $C_3$-$C_6$ cycloalkyloxy, $C_3$-$C_6$ cycloalkylthio, aryloxy, arylthio, heterocyclyloxy, or heterocyclylthio;

$R^{1'}$ and $R^{1''}$ through $R^{6'}$ and $R^{6''}$ are independently selected from the group consisting of H, $C_1$-$C_{20}$ alkyl, $C_2$-$C_{20}$ alkenyl, $C_3$-$C_6$ cycloalkyl, $C_1$-$C_{20}$ hetero-substituted alkyl, aryl, heterocyclyl, aralkyl, $C_1$-$C_{20}$ alkoxy, $C_2$-$C_{20}$ alkenyloxy, $C_3$-$C_6$ cycloalkyloxy, aryloxy, heterocyclyloxy, and halogen; or one or more or pairs of substituents selected from the group consisting of $R^{1'}$—$R^{2'}$, $R^{2'}$—$R^{3'}$, $R^{3'}$—$R^{4'}$, and $R^{5'}$—$R^{6'}$, together with the carbons to which they are attached, form a carbocyclic or pairs of substituents selected from the group consisting of $R^{1'}$-$R^{2'}$, $R^{2'}$-$R^{3'}$, $R^{3'}$-$R^{4'}$, and $R^{5'}$-$R^{6'}$, together with the carbons $R^7$ and $R^8$ are independently selected from the group consisting of H, $C_1$-$C_{20}$ alkyl, $C_1$-$C_{20}$ hetero-substituted alkyl, $C_3$-$C_6$ cycloalkyl, aryl, heterocyclyl, $C_1$-$C_{20}$ alkoxy, $C_1$-$C_{20}$ acyloxy, $C_1$-$C_{20}$ substituted-amino, $C_1$-$C_{20}$ protected-amino, $C_3$-$C_6$ cycloalkyloxy, aryloxy, heterocyclyloxy, and halogen;

with the proviso that any carbon-carbon double bonds in R or in $R^{1'}$ and $R^{1''}$ through $R^{6'}$ and $R^{6''}$ are essentially unreactive toward metathesis reactions with the catalyst.

2. The method of claim 1, further comprising combining a polymer block comprising repeating units (Ia) or (Ib) into a block copolymer.

3. The method of claim 1, wherein the catalyst is an alkylidene ruthenium complex of formula (L)(L')$X_2$Ru=CHR' or (L)$_2$(L')$X_2$Ru=CHR', wherein R' is selected from the group consisting of H, $C_1$-$C_{10}$ alkyl, $C_2$-$C_{10}$ alkenyl, $C_3$-$C_6$ cycloalkyl, and aryl;

L is a ligand selected from the group consisting of trialkyl phosphines, triarylphosphines, tri(cycloalkyl)phosphines, pyridine and substituted pyridine;

L' is a ligand selected from the group consisting of trialkyl phosphines, triarylphosphines, tri(cycloalkyl)phosphines, pyridine, substituted pyridine, and imidazolin-2-ylidine carbenes of formula

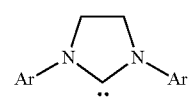

wherein Ar is an ortho-substituted aryl or an aryl; and
X is F, Cl, or Br.

4. The method of claim 3, wherein L is pyridine or substituted pyridine.

5. The method of claim 4, wherein L is 3-bromopyridyl, 3-chloropyridyl or pyridine.

6. The method of claim 2, wherein the catalyst is an alkylidene ruthenium complex of formula (L)(L')X$_2$Ru=CHR' or (L)$_2$(L')X$_2$Ru=CHR',
wherein R' is selected from the group consisting of H, C$_1$-C$_{10}$ alkyl, C$_2$-C$_{10}$ alkenyl, C$_3$-C$_6$ cycloalkyl, and aryl;

L is a ligand selected from the group consisting of trialkyl phosphines, triarylphosphines, tri(cycloalkyl)phosphines, pyridine and substituted pyridine;

L' is a ligand selected from the group consisting of trialkyl phosphines, triarylphosphines, tri(cycloalkyl)phosphines, pyridine, substituted pyridine, and imidazoline-2-ylidine carbenes of formula

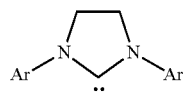

wherein Ar is an ortho-substituted aryl or an alkyl; and X is F, Cl, or Br.

7. The method of claim 3, claim 4 or claim 5, or claim 6 wherein L' is an imidazolin-2-ylidine carbene and Ar is selected from the group consisting of phenyl, mesityl, 2-methylphenyl, 2-ethylphenyl, 2-isopropylphenyl, 2,3-diisopropylphenyl, 2,6-difluorophenyl, and 3,5-di-t-butylphenyl.

8. The method of claim 1 or claim 2, wherein the catalyst is a molybdenum or tungsten metathesis catalyst.

9. A polymer comprising the repeating unit (Ia) or (Ib):

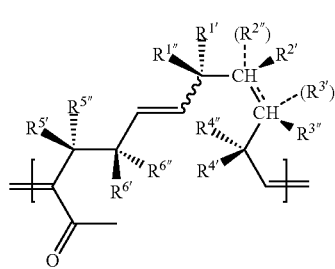

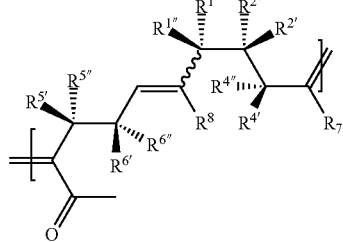

wherein R is selected form the group consisting of H, C$_1$-C$_{20}$ alkyl, C$_2$-C$_{20}$ alkenyl, C$_3$-C$_8$ cycloalkyl, heterocyclyl, aryl, aralkyl, C$_1$-C$_{20}$ alkoxy, C$_1$-C$_{20}$ alkylthio, C$_2$-C$_{20}$ alkenyloxy, C$_2$-C$_{20}$ alkenylthio, C$_3$-C$_6$ cycloalkyloxy, C$_3$-C$_6$ cycloalkylthio, aryloxy, arylthio, heterocyclyloxy, or heterocyclylthio;

R$^{1'}$ and R$^{1''}$ through R$^{6'}$ and R$^{6''}$ are independently selected from the group consisting of H, C$_1$-C$_{20}$ alkyl, C$_2$-C$_{20}$ alkenyl, C$_3$-C$_6$ cycloalkyl, C$_1$-C$_{20}$ hetero-substituted alkyl, aryl, heterocyclyl, aralkyl, C$_1$-C$_{20}$ alkoxy, C$_2$-C$_{20}$ alkenyloxy, C$_3$-C$_6$ cycloalkyloxy, aryloxy, heterocyclyloxy, and halogen; or one or pairs of substituents selected from the group consisting of R$^{1'}$—R$^{2'}$, R$^{2'}$—R$^{3'}$, R$^{3'}$—R$^{4'}$, and R$^{5'}$—R$^{6'}$, together with the carbons to which they are attached, form a carbocyclic or heterocyclic ring;

R$^7$ and R$^8$ are independently selected from the group consisting of H, C$_1$-C$_{20}$ alkyl, C$_1$-C$_{20}$ hetero-substituted alkyl, C$_3$-C$_6$ cycloalkyl, aryl, heterocyclyl, C$_1$-C$_{20}$ alkoxy, C$_1$-C$_{20}$ acyloxy, C$_1$-C$_{20}$ substituted-amino, C$_1$-C$_{20}$ protected-amino, C$_3$-C$_6$ cycloalkyloxy, aryloxy, heterocyclyloxy, and halogen.

10. The polymer of claim 9, wherein the polymer comprising the repeating unit (Ia) or (Ib) is a cyclic polymer.

11. The polymer of claim 9, wherein polymer comprising the repeating unit (Ia) or (Ib) is a block in a block copolymer.

12. A method of inhibiting microbial growth or inhibiting biofilm formation on a surface comprising the step of contacting one or more microbes with a polymer of claim 9.

13. A method of preparing a therapeutic agent for delivery to a subject comprising combining the therapeutic agent with a polymer of claim 9.

14. The method of claim 13, wherein the therapeutic agent is conjugated to the polymer.

15. The method of claim 13, wherein the therapeutic agent is contained in a micelle comprising the polymer.

* * * * *